US006960656B1

(12) United States Patent
Korenberg

(10) Patent No.: US 6,960,656 B1
(45) Date of Patent: Nov. 1, 2005

(54) NUCLEIC ACID ENCODING DS-CAM PROTEINS AND PRODUCTS RELATED THERETO

(75) Inventor: Julie R. Korenberg, Los Angeles, CA (US)

(73) Assignee: Cedars Sinai Medical Center, Los Angeles, CA (US)

( * ) Notice: Subject to any disclaimer, the term of this patent is extended or adjusted under 35 U.S.C. 154(b) by 0 days.

(21) Appl. No.: 08/956,991

(22) Filed: Oct. 23, 1997

Related U.S. Application Data

(60) Provisional application No. 60/029,322, filed on Oct. 25, 1996.

(51) Int. Cl.$^7$ ............................................... C07H 21/04

(52) U.S. Cl. .................. 536/23.1; 536/24.1; 536/24.33; 435/320.1; 435/252.3

(58) Field of Search .............................. 536/23.1, 24.1, 536/24.33, 23.5, 24.31; 435/320.1, 252.3, 6, 69.1, 91.1, 810; 514/44

(56) References Cited

U.S. PATENT DOCUMENTS

| | | | |
|---|---|---|---|
| 5,235,049 A | | 8/1993 | McClelland et al. |
| 5,264,554 A | | 11/1993 | Newman |
| 5,272,263 A | | 12/1993 | Hession et al. |
| 5,318,890 A | | 6/1994 | Rosen et al. |
| 5,389,520 A | | 2/1995 | Tedder et al. |
| 5,494,818 A | * | 2/1996 | Baker et al. ................. 435/219 |
| 5,519,008 A | | 5/1996 | Rao et al. |
| 5,525,487 A | | 6/1996 | Gallatin et al. |
| 5,952,171 A | * | 9/1999 | McCarthy et al. ............. 435/6 |

FOREIGN PATENT DOCUMENTS

WO     WO 90/13300     11/1990

OTHER PUBLICATIONS

Attwood Science 2000; 290:471–473.*
Skolnick et al. Trends in Biotech. 2000; 18(1):34–39.*
Metzler et al. Nature Structural Biol. 1997; 4:527–531.*
Genexpress, GenBank Accession No. F13426, Mar. 5, 1995.*
Blechschmidt, et al., GenBank Accession No. AF042091, Mar. 21, 1998.*
EMBL Database, EMEST9 Entry Hsczwh041, Accession No. Z45894 "The Genexpress cDNA program", Nov. 6, 1994.
EMBL Database, EMEST5 Entry Hs326306, Accession No. N80326 "The WashU–Merck EST Project", Apr. 4, 1996.
EMBL Database, EMEST9 Entry Hsczwh042, Accession No. Z41519 "The Genexpress cDNA program", Nov. 5, 1994.
EMBL Database, EMHUM1 Entry Hsmc18b12, Accession No. X88325 "Cloning of trapped exons from human chromosome. 21", Jul. 18, 1996.

Murphy et al., 1993, "Overexpression of LFA–1 and ICAM–1 in Down Syndrome thymus" vol. 150, pp. 5696–5703.
Cho et al., "The DCC Gene: Structural Analysis and Mutations in Colorectal Carcinomas" *Genomics* 19:525–531 (1994).
Cunningham et al., "Neural Cell Adhesion Molecule: Structure, Immunoglobulin–Like Domains, Cell Surface Modulation, and Alternative RNA Splicing" *Science* 236:799–806 (1987).
Davis et al., "Genetic Dissection of Structural and Functional Components of Synaptic Plasticity. III. CREB Is Necessary for Presynaptic Functional Plasticity", *Neuron* 17:669–679 (1996).
Edelman and Crossin, "Cell Adhesion Molecules: Implications for a Molecular Histology" *Annul. Rev. Biochem.* 60:155–190 (1991).
Evans et al., "Cloning of a Delta Opioid Receptor by Functional Expression" *Science* 258:1952–1955 (1992).
Fearon et al., "Identification of a Chromosome 18q Gene That Is Altered in Colorectal Cancers" *Science* 247:49–56 (1990).
Figarella–Branger et al., Expression of Various NCAM Isoforms in Human Embryonic Muscles: Correlation with Myosin Heavy Chain Phenotypes *Journal of Neuropathology and Experienced Neurology* 51(1):12–23 (1992).
Gardiner et al., "YAC Analysis and Minimal Tiling Path Construction for Chromosome 21q" *Somatic Cell and Molecular Genetics* 21(6):399–414 (1995).
Hara et al., "Mutation analysis of a Sandhoff disease patient in the Maronite community in Cyprus" *Hum Genet* 94:136–140 (1994).
Hubert et al., "BAC and PAC Contigs Covering 3.5 Mb of he Down Syndrome Congenital Heart Disease Region between D21S55 and MX1 on Chromosome 21" *Genomics* 41:218–226 (1997).
Ioannou et al., "A new bacteriophage P1–derived vector for the propagation of large human DNA fragments" *Nature Genetics* 6:84–89 (1994).
Jouet et al., "X–linked spastic paraplegia (SPG1), MASA syndrome and X–linked hydrocephalus result from mutations in the L1 gene" *Nature Genetics* 7:402–407 (1994).
Jackson, Ian J., "A reappraisal of non–consensus mRNA splice sites" *Nucleic Acids Research* 19 (14):3795–3798 (1991).

(Continued)

*Primary Examiner*—Juliet C. Switzer
(74) *Attorney, Agent, or Firm*—Michael J. Wise; Perkins Coie LLP

(57) ABSTRACT

In accordance with the present invention, there are provided Down Syndrome-Cell Adhesion Molecule (DS-CAM) proteins. Nucleic acid sequences encoding such proteins and assays employing same are also disclosed. The invention DS-CAM proteins can be employed in a variety of ways, for example, for the production of anti-DS-CAM antibodies thereto, in therapeutic compositions and methods employing such proteins and/or antibodies. DS-CAM proteins are also useful in bioassays to identify agonists and antagonists thereto.

9 Claims, 5 Drawing Sheets

OTHER PUBLICATIONS

Kakizuka et al., "A mouse cdc25 homolog is differentially and developmentally expressed" *Genes & Development* 6:578–590 (1992).

Keino–Masu et al., "Deleted in Colorectal Cancer (DCC) Encodes a Netrin Receptor" *Cell* 87:175–185 (1996).

Korenberg et al., "Down Syndrome: Molecular Mapping of the Congenital Heart Disease and Duodenal Stenosis"*Am. J. Hum. Genet.* 50:294–302 (1992).

Korenberg et al., "Down syndrome phenotypes: The consequences of chromosomal imbalance" *Proc. Natl. Acad. Sci. USA* 91:4997–5001 (1994).

Korenberg and Chen, "Human cDNA mapping using a high–resolution R–banding technique and fluorescence in situ hybridization" *Cytogenet Cell Genet* 69:196–200 (1995).

Korenberg et al., "A High–fidelity Physical Map of Human Chromosome 21q in Yeast Artificial Chromosomes" *Genome Research*, 5:427–443 (1995).

Lane et al., "Characterization of a Highly Conserved Human Homolog to the Chicken Neural Cell Surface Protein Bravo/Nr–CAM That Maps to Chromosome Band 7q31" *Genomics* 35:456–465 (1996).

Mauro et al., "Homophilic and Heterophilic Binding Activities of Nr–CAM, a Nervous System Cell Adhesion Molecule" *The Journal of Cell Biology*, 119(1):191–202 (1992).

Milev et al., "TAG–1/Axonin–1 Is a High–affinity Ligand of Neurocan, Phosphacan/Protein–tyrosine Phosphatase–$\zeta/\beta$, and N–CAM" *J. Biol. Chem.* 271(26):15716–15723 (1996).

Moos et al., "Nueral adhesion molecule L1 as a member of the immunoglobulin superfamily with binding domains similar to fibronectin" *Nature* 334:701–703 (1988).

O'Neill et al., "Functional domain analysis of glass, a zinc–finger–containing transcription factor in Drosophila" *Proc. Natl. Acad. Sci. USA* 92:6557–6561 (1995).

Ranscht, B., "Sequence of Contactin, a 130–kD Glycoprotein Concentrated in Areas of Interneuronal Contact, Defines a New Member of the Immunoglobulin Supergene Family in the Nervous System" *J. Cell Biol.* 107:1561–1573 (1988).

Rosenthal et al., "Aberrant splicing of neural cell adhesion molecule L1 mRNA in a family with X–linked hydrocephalus" *Nature Genetics* 2:107–112 (1992).

Schuster et al., "Genetic Dissection of Structural and Functional Components of Synaptic Plasticity. II. Fasciclin II Controls Presynaptic Structural Plasticity" *Neuron* 17:655–667 (1996).

Taira et al., "Molecular Cloning and Functional Expression of Gicerin, a Novel Cell Adhesion Molecule That Binds to Neurite Outgrowth Factor" *Neuron* 12:861–872 (1994).

Tessier–Lavigne and Goodman, "The Molecular Biology of Axon Guidance" *Science* 274:1123–1133 (1996).

Walsh and Doherty, "Factors regulating the expression and function of calcium–independent cell adhesion molecules" *Current Opinion in Cell Biology* 5:791–796 (1993).

Yamakawa et al., "Isolation and characterization of a candidate gene for progressive myoclonus epilepsy on 21q22.3" *Human Molecular Genetics* 4(4):709–716 (1995).

Yamakawa et al., "A periodic tryptophan protein 2 gene homologue (PWP2H) in the candidate region of progressive myoclonus epilepsy on 21q22.3" *Cytogenet Cell Genet* 74:140–145 (1996).

Yoshihara et al., "BIG–1: A New TAG–1/F3–Related Member of the Immunoglobulin Superfamily with Neurite Outgrowth–Promoting Activity" *Neuron* 13:415–426 (1994).

Zisch et al., "Neuronal Cell Adhesion Molecule Contactin/F11 Binds to Tenascin Via Its Immunoglobulin–like Domains" *J. Cell Biol.* 119(1):203–213 (1992).

* cited by examiner

SEQUENCE LISTING

<160> NUMBER OF SEQ ID NOS: 11

<210> SEQ ID NO 1
<211> LENGTH: 6604
<212> TYPE: DNA
<213> ORGANISM: HUMAN
<220> FEATURE:
<221> NAME/KEY: CDS
<222> LOCATION: (453)..(6182)

<400> SEQUENCE: 1

```
tgactgaggc cggagcacgg caaagatgag cctgcccgcc cgcctgctgc ctggatgcgg      60
agggtgaggg ctggcgcacg ggaggccgct ggctgcgcat tctgggcgcc gagtgcccgg     120
gatgagctca cgcccgcgtc tgcggctctc tccacctgcc gacctgccgg gggcccactg     180
agctgacggc gcacctgggc tccggccgca gcgtggggcg cggcgcccgg gagcaggtgt     240
gcaggagcgc agcgcgcggc gagcgcagcc ctcgctccgg agcccggccg cgccgcgtgc     300
ccgggcggct aggcagcggc ggcggcgcg gcgggcggcg gcgggcggc ggcccccggg       360 caggtgccga gcggcgagcg gagccgggcc gggcggagcg cgggggggcga ggccggcgcg     420 tcgctcgcgg gaggccgggg agcggcaggg gc atg tgg ata ctg gct ctc tcc     473
                                  Met Trp Ile Leu Ala Leu Ser
                                    1               5 ttg ttc cag agc ttc gcg aat gtt ttc agt gaa gac cta cac tcc agc     521
Leu Phe Gln Ser Phe Ala Asn Val Phe Ser Glu Asp Leu His Ser Ser
        10                  15                  20 ctc tac ttt gtc aat gca tct ctg caa gag gta gtg ttt gcc agc acc     569
Leu Tyr Phe Val Asn Ala Ser Leu Gln Glu Val Val Phe Ala Ser Thr
    25                  30                  35 acg ggg act ctg gtg ccc tgc ccc gca gca ggc atc cct cct gtg act     617
Thr Gly Thr Leu Val Pro Cys Pro Ala Ala Gly Ile Pro Pro Val Thr
40                  45                  50                  55 ctc aga tgg tac cta gcc acg ggc gag gag atc tac gat gtc ccc ggg     665
Leu Arg Trp Tyr Leu Ala Thr Gly Glu Glu Ile Tyr Asp Val Pro Gly
                60                  65                  70 atc cgc cac gtc cac ccc aac ggc act ctc caa att ttc ccc ttc cct     713
Ile Arg His Val His Pro Asn Gly Thr Leu Gln Ile Phe Pro Phe Pro
            75                  80                  85 cct tca agc ttc agt acc tta atc cat gat aat act tat tat tgc aca     761
Pro Ser Ser Phe Ser Thr Leu Ile His Asp Asn Thr Tyr Tyr Cys Thr
        90                  95                 100 gct gaa aat cct tca ggg aaa att aga agt cag gat gtc cac atc aag     809
Ala Glu Asn Pro Ser Gly Lys Ile Arg Ser Gln Asp Val His Ile Lys
    105                 110                 115 gct gtt tta cgg gag ccc tat aca gtc cgt gtg gag gac cag aaa acc     857
```

|  |  |
|---|---|
| Ala Val Leu Arg Glu Pro Tyr Thr Val Arg Val Glu Asp Gln Lys Thr<br>120               125                        130                       135 |  |
| atg aga ggc aat gtt gcg gtc ttc aag tgc att atc ccc tcc tcg gtg<br>Met Arg Gly Asn Val Ala Val Phe Lys Cys Ile Ile Pro Ser Ser Val<br>                    140                        145                     150 | 905 |
| gag gcg tac atc act gtc gtc tca tgg gag aaa gac act gtt tca ctt<br>Glu Ala Tyr Ile Thr Val Val Ser Trp Glu Lys Asp Thr Val Ser Leu<br>                155                        160                     165 | 953 |
| gtc tca gga tct aga ttt ctc atc aca tcc acg gga gcc ttg tat att<br>Val Ser Gly Ser Arg Phe Leu Ile Thr Ser Thr Gly Ala Leu Tyr Ile<br>         170                       175                     180 | 1001 |
| aaa gat gta cag aat gaa gat gga ttg tat aac tac cgc tgc atc acg<br>Lys Asp Val Gln Asn Glu Asp Gly Leu Tyr Asn Tyr Arg Cys Ile Thr<br>185                        190                        195 | 1049 |
| cgg cat cga tac acc gga gag acg agg cag agc aac agc gcc aga ctt<br>Arg His Arg Tyr Thr Gly Glu Thr Arg Gln Ser Asn Ser Ala Arg Leu<br>200                        205                      210                     215 | 1097 |
| ttt gta tca gac cca gcg aac tca gcc cca tcc ata ctg gat ggg ttt<br>Phe Val Ser Asp Pro Ala Asn Ser Ala Pro Ser Ile Leu Asp Gly Phe<br>                    220                        225                     230 | 1145 |
| gac cat cgc aaa gcc atg gct ggg cag cgt gtg gag ctg cct tgc aaa<br>Asp His Arg Lys Ala Met Ala Gly Gln Arg Val Glu Leu Pro Cys Lys<br>               235                       240                     245 | 1193 |
| gcg ctc ggg cac cct gag cca gat tac cgc tgg ctg aag gac aac atg<br>Ala Leu Gly His Pro Glu Pro Asp Tyr Arg Trp Leu Lys Asp Asn Met<br>         250                       255                     260 | 1241 |
| ccc ctg gaa ctt tca ggg agg ttc cag aag acc gtg acg ggg ctg ctc<br>Pro Leu Glu Leu Ser Gly Arg Phe Gln Lys Thr Val Thr Gly Leu Leu<br>265                        270                      275 | 1289 |
| att gag aac att cgc ccc tcg gac tca ggc agc tat gtt tgt gaa gtg<br>Ile Glu Asn Ile Arg Pro Ser Asp Ser Gly Ser Tyr Val Cys Glu Val<br>280                        285                      290                     295 | 1337 |
| tcc aac aga tac gga act gct aag gtg ata ggc cgc ctg tac gtg aaa<br>Ser Asn Arg Tyr Gly Thr Ala Lys Val Ile Gly Arg Leu Tyr Val Lys<br>               300                       305                     310 | 1385 |
| cag cca ctg aaa gcc acc atc agt ccc agg aag gtt aaa agc agc gtg<br>Gln Pro Leu Lys Ala Thr Ile Ser Pro Arg Lys Val Lys Ser Ser Val<br>               315                       320                     325 | 1433 |
| ggt agc caa gtt tcc ttg tcc tgc agc gtg aca gga act gag gac cag<br>Gly Ser Gln Val Ser Leu Ser Cys Ser Val Thr Gly Thr Glu Asp Gln<br>         330                       335                     340 | 1481 |
| gaa ctc tcc tgg tac cgc aat ggt gaa atc ctc aac cct gga aaa aat<br>Glu Leu Ser Trp Tyr Arg Asn Gly Glu Ile Leu Asn Pro Gly Lys Asn<br>345                        350                      355 | 1529 |
| gtg agg atc aca ggg atc aac cac gaa aac ctt ata atg gat cac atg<br>Val Arg Ile Thr Gly Ile Asn His Glu Asn Leu Ile Met Asp His Met<br>360                        365                      370                     375 | 1577 |
| gtc aaa agt gac ggg ggc gca tac cag tgc ttt gtg cgc aag gac aag<br>Val Lys Ser Asp Gly Gly Ala Tyr Gln Cys Phe Val Arg Lys Asp Lys<br>                    380                        385                     390 | 1625 |
| ctg tcc gct caa gac tat gtg cag gtg gtc ctt gaa gat gga act ccc<br>Leu Ser Ala Gln Asp Tyr Val Gln Val Val Leu Glu Asp Gly Thr Pro<br>               395                       400                     405 | 1673 |
| aaa att att tct gcc ttt agt gaa aag gtg gtg agt cca gca gag ccg<br>Lys Ile Ile Ser Ala Phe Ser Glu Lys Val Val Ser Pro Ala Glu Pro<br>               410                       415                     420 | 1721 |
| gtt tcc ctt atg tgc aac gtg aag gga aca cct ttg ccc acg atc acg<br>Val Ser Leu Met Cys Asn Val Lys Gly Thr Pro Leu Pro Thr Ile Thr<br>425                        430                      435 | 1769 |

```
tgg acc ctg gac gat gac ccg att ctc aag ggt ggc agt cac cgc atc    1817
Trp Thr Leu Asp Asp Asp Pro Ile Leu Lys Gly Gly Ser His Arg Ile
440                 445                 450                 455 agc cag atg atc acg tcg gag ggg aac gtg gtc agc tac ctg aac atc    1865
Ser Gln Met Ile Thr Ser Glu Gly Asn Val Val Ser Tyr Leu Asn Ile
                    460                 465                 470 tcc agc tcc cag gtc cgg gac ggg gga gtc tac cgc tgc act gcc aac    1913
Ser Ser Ser Gln Val Arg Asp Gly Gly Val Tyr Arg Cys Thr Ala Asn
                475                 480                 485 aac tcg gcg gga gtc gtc ctg tac cag gct cga ata aac gta aga ggg    1961
Asn Ser Ala Gly Val Val Leu Tyr Gln Ala Arg Ile Asn Val Arg Gly
            490                 495                 500 cct gca agc att cga cca atg aaa aac atc aca gca ata gca gga cgg    2009
Pro Ala Ser Ile Arg Pro Met Lys Asn Ile Thr Ala Ile Ala Gly Arg
        505                 510                 515 gac aca tac att cac tgt cgt gtg att ggc tat ccg tat tac tcc att    2057
Asp Thr Tyr Ile His Cys Arg Val Ile Gly Tyr Pro Tyr Tyr Ser Ile
520                 525                 530                 535 aaa tgg tac aag aac tct aac ctg ctt cct ttc aac cac cgc caa gtg    2105
Lys Trp Tyr Lys Asn Ser Asn Leu Leu Pro Phe Asn His Arg Gln Val
                    540                 545                 550 gca ttt gag aac aat gga act ctt aaa ctt tca gat gtg caa aag gaa    2153
Ala Phe Glu Asn Asn Gly Thr Leu Lys Leu Ser Asp Val Gln Lys Glu
                555                 560                 565 gtg gac gag ggg gag tac acg tgc aac gtg ttg gtt caa cca caa ctc    2201
Val Asp Glu Gly Glu Tyr Thr Cys Asn Val Leu Val Gln Pro Gln Leu
            570                 575                 580 tcc acc agc cag agc gtc cac gtg acc gtg aaa gtt ccg cct ttc ata    2249
Ser Thr Ser Gln Ser Val His Val Thr Val Lys Val Pro Pro Phe Ile
        585                 590                 595 caa ccc ttt gag ttt cca aga ttc tcc att ggg cag cgg gtc ttc atc    2297
Gln Pro Phe Glu Phe Pro Arg Phe Ser Ile Gly Gln Arg Val Phe Ile
600                 605                 610                 615 ccc tgt gtt gtg gtc tca ggg gac tta ccc atc acg atc acc tgg cag    2345
Pro Cys Val Val Val Ser Gly Asp Leu Pro Ile Thr Ile Thr Trp Gln
                    620                 625                 630 aag gat ggc cgg cca atc cct ggg agc ctt ggg gtg acc att gac aat    2393
Lys Asp Gly Arg Pro Ile Pro Gly Ser Leu Gly Val Thr Ile Asp Asn
                635                 640                 645 att gac ttc acg agc tcc ttg agg att tcc aat ctc tcg ctc atg cac    2441
Ile Asp Phe Thr Ser Ser Leu Arg Ile Ser Asn Leu Ser Leu Met His
            650                 655                 660 aat ggg aat tac acc tgc ata gcc cgg aat gag gcc gcc gct gtg gag    2489
Asn Gly Asn Tyr Thr Cys Ile Ala Arg Asn Glu Ala Ala Ala Val Glu
        665                 670                 675 cac caa agc cag ttg att gtc aga gtt cct ccc aag ttt gtg gtt cag    2537
His Gln Ser Gln Leu Ile Val Arg Val Pro Pro Lys Phe Val Val Gln
680                 685                 690                 695 cca cgg gac cag gac ggg att tat ggc aaa gca gtc atc ctc aat tgt    2585
Pro Arg Asp Gln Asp Gly Ile Tyr Gly Lys Ala Val Ile Leu Asn Cys
                    700                 705                 710 tct gct gag ggt tac cct gta cct acc atc gtg tgg aaa ttc tct aaa    2633
Ser Ala Glu Gly Tyr Pro Val Pro Thr Ile Val Trp Lys Phe Ser Lys
                715                 720                 725 ggt gct ggg gtt ccc cag ttc cag cca att gcc cta aat ggc cga atc    2681
Gly Ala Gly Val Pro Gln Phe Gln Pro Ile Ala Leu Asn Gly Arg Ile
            730                 735                 740 caa gtt ctc agc aat ggg tcg ttg ctg atc aag cat gtc gtg gag gaa    2729
Gln Val Leu Ser Asn Gly Ser Leu Leu Ile Lys His Val Val Glu Glu
        745                 750                 755
```

-continued

| | |
|---|---|
| gac agt ggc tac tac ctc tgc aag gtc agc aac gat gtg ggc gca gac<br>Asp Ser Gly Tyr Tyr Leu Cys Lys Val Ser Asn Asp Val Gly Ala Asp<br>760                       765                   770                   775 | 2777 |
| gtc agc aag tcc atg tac ctc acg gtt aaa att cct gcg atg ata aca<br>Val Ser Lys Ser Met Tyr Leu Thr Val Lys Ile Pro Ala Met Ile Thr<br>                  780                   785                   790 | 2825 |
| tcc tat cca aat act acc ctg gcc acg cag ggg cag aaa aag gag atg<br>Ser Tyr Pro Asn Thr Thr Leu Ala Thr Gln Gly Gln Lys Lys Glu Met<br>          795                   800                   805 | 2873 |
| agc tgc acg gcg cat ggt gag aag ccc att ata gtc cgc tgg gag aag<br>Ser Cys Thr Ala His Gly Glu Lys Pro Ile Ile Val Arg Trp Glu Lys<br>810                       815                   820 | 2921 |
| gag gac cga atc att aac cct gag atg gcc cgt tat ctt gtg tcc acc<br>Glu Asp Arg Ile Ile Asn Pro Glu Met Ala Arg Tyr Leu Val Ser Thr<br>825                       830                   835 | 2969 |
| aag gag gtg gga gaa gag gtg att tct act ctg cag att ttg cca act<br>Lys Glu Val Gly Glu Glu Val Ile Ser Thr Leu Gln Ile Leu Pro Thr<br>840                       845                   850                   855 | 3017 |
| gtg aga gaa gat tct ggt ttc ttt tcc tgc cat gct att aat tct tat<br>Val Arg Glu Asp Ser Gly Phe Phe Ser Cys His Ala Ile Asn Ser Tyr<br>                  860                   865                   870 | 3065 |
| ggg gag gac cgt gga ata att cag ctc aca gtg caa gag ccc cca gac<br>Gly Glu Asp Arg Gly Ile Ile Gln Leu Thr Val Gln Glu Pro Pro Asp<br>          875                   880                   885 | 3113 |
| cct ccc gaa att gag atc aaa gat gtc aaa gca cgc aca att acg ctc<br>Pro Pro Glu Ile Glu Ile Lys Asp Val Lys Ala Arg Thr Ile Thr Leu<br>                  890                   895                   900 | 3161 |
| agg tgg acc atg ggg ttt gat gga aac agt ccc atc aca ggc tac gat<br>Arg Trp Thr Met Gly Phe Asp Gly Asn Ser Pro Ile Thr Gly Tyr Asp<br>905                       910                   915 | 3209 |
| att gaa tgc aaa aat aaa tca gac tcc tgg gat tct gct cag aga acc<br>Ile Glu Cys Lys Asn Lys Ser Asp Ser Trp Asp Ser Ala Gln Arg Thr<br>920                       925                   930                   935 | 3257 |
| aaa gat gtt tcc cct cag ctg aac tcg gcc acc atc att gat atc cac<br>Lys Asp Val Ser Pro Gln Leu Asn Ser Ala Thr Ile Ile Asp Ile His<br>                  940                   945                   950 | 3305 |
| cct tcc tcc acc tac agc atc cgc atg tac gcc aag aac cgg att ggc<br>Pro Ser Ser Thr Tyr Ser Ile Arg Met Tyr Ala Lys Asn Arg Ile Gly<br>          955                   960                   965 | 3353 |
| aag agc gag ccc agc aac gag ctc acc atc acg gcg gac gag gca gct<br>Lys Ser Glu Pro Ser Asn Glu Leu Thr Ile Thr Ala Asp Glu Ala Ala<br>970                       975                   980 | 3401 |
| cct gat ggt cca cct cag gaa gtt cac ctg gag cct ata tca tct cag<br>Pro Asp Gly Pro Pro Gln Glu Val His Leu Glu Pro Ile Ser Ser Gln<br>985                       990                   995 | 3449 |
| agc atc agg gtc aca tgg aag gct ccc aag aaa cat ttg caa aat ggg<br>Ser Ile Arg Val Thr Trp Lys Ala Pro Lys Lys His Leu Gln Asn Gly<br>1000                   1005                1010                1015 | 3497 |
| att atc cgt ggc tac caa ata ggt tac cga gag tac agc act ggg ggt<br>Ile Ile Arg Gly Tyr Gln Ile Gly Tyr Arg Glu Tyr Ser Thr Gly Gly<br>                  1020                1025               1030 | 3545 |
| aac ttc caa ttc aac att atc agt gtc gac acc agc ggg gac agt gag<br>Asn Phe Gln Phe Asn Ile Ile Ser Val Asp Thr Ser Gly Asp Ser Glu<br>          1035                1040                1045 | 3593 |
| gtt tac acc ctg gac aac ctg aat aag ttc act cag tac ggc ctg gtg<br>Val Tyr Thr Leu Asp Asn Leu Asn Lys Phe Thr Gln Tyr Gly Leu Val<br>1050                   1055                1060 | 3641 |
| gtg cag gcc tgt aac cgg gcc ggc acg ggg cct tct tct cag gaa atc<br>Val Gln Ala Cys Asn Arg Ala Gly Thr Gly Pro Ser Ser Gln Glu Ile | 3689 |

```
                 1065                1070                 1075
atc acc acc act ctc gag gat gtg ccc agt tac ccc ccc gaa aat gtc    3737
Ile Thr Thr Thr Leu Glu Asp Val Pro Ser Tyr Pro Pro Glu Asn Val
1080                1085                 1090                1095 caa gcc ata gca aca tca cca gaa agc ata tca ata tcc tgg tcc aca    3785
Gln Ala Ile Ala Thr Ser Pro Glu Ser Ile Ser Ile Ser Trp Ser Thr
                1100                1105                 1110 ctt tcc aag gaa gcc ttg aat gga att ctc cag ggg ttc aga gtc att    3833
Leu Ser Lys Glu Ala Leu Asn Gly Ile Leu Gln Gly Phe Arg Val Ile
         1115                1120                 1125 tac tgg gcc aac ctc atg gac gga gag ctg ggt gag att aaa aac atc    3881
Tyr Trp Ala Asn Leu Met Asp Gly Glu Leu Gly Glu Ile Lys Asn Ile
    1130                1135                 1140 acc acc aca cag cct tca ctg gag ctg gac ggg ctg gaa aag tac acc    3929
Thr Thr Thr Gln Pro Ser Leu Glu Leu Asp Gly Leu Glu Lys Tyr Thr
1145                1150                 1155 aac tac agc atc cag gtg ctg gcc ttc acc cgc gca gga gac ggg gtc    3977
Asn Tyr Ser Ile Gln Val Leu Ala Phe Thr Arg Ala Gly Asp Gly Val
1160                1165                 1170                1175 agg agt gag cag atc ttc acc cgg acc aaa gag gat gtt cca ggt cct    4025
Arg Ser Glu Gln Ile Phe Thr Arg Thr Lys Glu Asp Val Pro Gly Pro
                1180                1185                 1190 ccc gcg ggt gtg aag gca gcg gcg gcc tca gcc tcc atg gtc ttt gtg    4073
Pro Ala Gly Val Lys Ala Ala Ala Ala Ser Ala Ser Met Val Phe Val
         1195                1200                 1205 tcc tgg ctt ccc cct ctc aag ctg aac ggc atc atc cga aag tac act    4121
Ser Trp Leu Pro Pro Leu Lys Leu Asn Gly Ile Ile Arg Lys Tyr Thr
    1210                1215                 1220 gta ttc tgc tcc cac ccc tat ccc aca gtg atc agc gag ttt gag gcc    4169
Val Phe Cys Ser His Pro Tyr Pro Thr Val Ile Ser Glu Phe Glu Ala
1225                1230                 1235 tct ccc gac tcg ttt tcc tac aga att ccc aac ctg agt agg aat cgt    4217
Ser Pro Asp Ser Phe Ser Tyr Arg Ile Pro Asn Leu Ser Arg Asn Arg
1240                1245                 1250                1255 cag tac agc gtc tgg gtg gtg gct gtt act tca gcc gga aga ggc aac    4265
Gln Tyr Ser Val Trp Val Val Ala Val Thr Ser Ala Gly Arg Gly Asn
                1260                1265                 1270 agc agt gaa atc atc aca gtc gag cca cta gca aaa gct cct gca cga    4313
Ser Ser Glu Ile Ile Thr Val Glu Pro Leu Ala Lys Ala Pro Ala Arg
         1275                1280                 1285 atc ctg acc ttc agt ggg aca gtg act act cca tgg atg aaa gac att    4361
Ile Leu Thr Phe Ser Gly Thr Val Thr Thr Pro Trp Met Lys Asp Ile
    1290                1295                 1300 gtc ttg cct tgt aag gct gtt ggg gac cct tct cct gca gtc aaa tgg    4409
Val Leu Pro Cys Lys Ala Val Gly Asp Pro Ser Pro Ala Val Lys Trp
1305                1310                 1315 atg aaa gac agt aac ggg aca ccc agt cta gta acg att gat ggg cgg    4457
Met Lys Asp Ser Asn Gly Thr Pro Ser Leu Val Thr Ile Asp Gly Arg
1320                1325                 1330                1335 agg agc atc ttt agc aac gga agc ttc att att cgc acg gtg aaa gca    4505
Arg Ser Ile Phe Ser Asn Gly Ser Phe Ile Ile Arg Thr Val Lys Ala
                1340                1345                 1350 gaa gac tcc ggc tat tac agc tgc att gcc aat aac aac tgg gga tct    4553
Glu Asp Ser Gly Tyr Tyr Ser Cys Ile Ala Asn Asn Asn Trp Gly Ser
         1355                1360                 1365 gat gaa att att tta aac tta caa gta caa gtt cca cca gat cag cct    4601
Asp Glu Ile Ile Leu Asn Leu Gln Val Gln Val Pro Pro Asp Gln Pro
    1370                1375                 1380 cgg ctt aca gtc tcc aag acc acg tct tcc tcc atc acc ctt tct tgg    4649
```

```
                                                     -continued

Arg Leu Thr Val Ser Lys Thr Thr Ser Ser Ser Ile Thr Leu Ser Trp
    1385                1390                1395 ctc cct gga gac aac ggg ggc agc tct atc aga gga tac ata ctg cag              4697
Leu Pro Gly Asp Asn Gly Gly Ser Ser Ile Arg Gly Tyr Ile Leu Gln
1400                1405                1410                1415 tac tcc gag gac aat agt gag cag tgg ggg agt ttt cca atc agc ccc              4745
Tyr Ser Glu Asp Asn Ser Glu Gln Trp Gly Ser Phe Pro Ile Ser Pro
                1420                1425                1430 agc gaa cgt tcc tat cgc ttg gaa aat ctc aaa tgt ggg act tgg tat              4793
Ser Glu Arg Ser Tyr Arg Leu Glu Asn Leu Lys Cys Gly Thr Trp Tyr
            1435                1440                1445 aag ttc aca ctg aca gcc caa aat gga gtg ggc cca ggg cgc ata agt              4841
Lys Phe Thr Leu Thr Ala Gln Asn Gly Val Gly Pro Gly Arg Ile Ser
        1450                1455                1460 gaa atc ata gaa gca aag acc tta gga aaa gag ccc cag ttc tca aag              4889
Glu Ile Ile Glu Ala Lys Thr Leu Gly Lys Glu Pro Gln Phe Ser Lys
1465                1470                1475 gag cag gag ctg ttt gcc agc atc aac acc aca cgc gtg agg ctg aac              4937
Glu Gln Glu Leu Phe Ala Ser Ile Asn Thr Thr Arg Val Arg Leu Asn
1480                1485                1490                1495 ctc att ggc tgg aat gat ggc ggc tgc ccc atc acc tcc ttc aca cta              4985
Leu Ile Gly Trp Asn Asp Gly Gly Cys Pro Ile Thr Ser Phe Thr Leu
                1500                1505                1510 gag tac agg ccc ttt ggg acc aca gtt tgg acc aca gct cag agg acc              5033
Glu Tyr Arg Pro Phe Gly Thr Thr Val Trp Thr Thr Ala Gln Arg Thr
            1515                1520                1525 tct ctc tcc aag tcc tac atc ctg tat gac ctg cag gaa gcc acc tgg              5081
Ser Leu Ser Lys Ser Tyr Ile Leu Tyr Asp Leu Gln Glu Ala Thr Trp
        1530                1535                1540 tat gag ctg cag atg cgg gtg tgc aac agt gcg ggc tgc gcg gag aag              5129
Tyr Glu Leu Gln Met Arg Val Cys Asn Ser Ala Gly Cys Ala Glu Lys
    1545                1550                1555 cag gcc aac ttc gct acg ctg aac tac gat ggc agt aca att cct cca              5177
Gln Ala Asn Phe Ala Thr Leu Asn Tyr Asp Gly Ser Thr Ile Pro Pro
1560                1565                1570                1575 ctc att aag tca gtt gtc caa aac gaa gaa ggg ctg acg acc aac gag              5225
Leu Ile Lys Ser Val Val Gln Asn Glu Glu Gly Leu Thr Thr Asn Glu
                1580                1585                1590 ggg ctc aag atg ctg gtg acc atc tcc tgt atc ctg gtg ggg gtc ttg              5273
Gly Leu Lys Met Leu Val Thr Ile Ser Cys Ile Leu Val Gly Val Leu
            1595                1600                1605 ctg ctg ttt gtg ctc ctg ctg gtt gtg cgg agg agg cgg cgg gag cag              5321
Leu Leu Phe Val Leu Leu Leu Val Val Arg Arg Arg Arg Arg Glu Gln
        1610                1615                1620 agg cta aag agg ctg cga gat gca aag agt tta gct gaa atg ctc atg              5369
Arg Leu Lys Arg Leu Arg Asp Ala Lys Ser Leu Ala Glu Met Leu Met
    1625                1630                1635 agt aag aat acc cgg act tca gat acg tta agc aag caa cag cag acc              5417
Ser Lys Asn Thr Arg Thr Ser Asp Thr Leu Ser Lys Gln Gln Gln Thr
1640                1645                1650                1655 ctg cga atg cac atc gac ata ccc agg gct cag ctt ttg att gaa gag              5465
Leu Arg Met His Ile Asp Ile Pro Arg Ala Gln Leu Leu Ile Glu Glu
                1660                1665                1670 aga gac acg atg gag acc att gat gat cgc tcc acg gtt ctg ttg acg              5513
Arg Asp Thr Met Glu Thr Ile Asp Asp Arg Ser Thr Val Leu Leu Thr
            1675                1680                1685 gat gct gac ttt gga gag gca gct aag cag aag tcc ctg acg gtc act              5561
Asp Ala Asp Phe Gly Glu Ala Ala Lys Gln Lys Ser Leu Thr Val Thr
        1690                1695                1700
```

-continued

| | |
|---|---|
| cac acg gtc cat tac caa tcg gtg tct cag gcc act ggg ccc tta gtg<br>His Thr Val His Tyr Gln Ser Val Ser Gln Ala Thr Gly Pro Leu Val<br>    1705                          1710                    1715 | 5609 |
| gat gtt tca gac gct cgg ccg gga acg aat ccc acc acc agg agg aat<br>Asp Val Ser Asp Ala Arg Pro Gly Thr Asn Pro Thr Thr Arg Arg Asn<br>1720                     1725                    1730                    1735 | 5657 |
| gcc aag gct ggg ccc aca gcg aga aac cgc tat gcc agc cag tgg acc<br>Ala Lys Ala Gly Pro Thr Ala Arg Asn Arg Tyr Ala Ser Gln Trp Thr<br>    1740                          1745                    1750 | 5705 |
| ctc aac cga ccc cac ccc acc atc tca gca cac acc ctc acc aca gac<br>Leu Asn Arg Pro His Pro Thr Ile Ser Ala His Thr Leu Thr Thr Asp<br>        1755                        1760                  1765 | 5753 |
| tgg agg ctg cca aca ccc agg gct gca gga tca gta gac aaa gag agc<br>Trp Arg Leu Pro Thr Pro Arg Ala Ala Gly Ser Val Asp Lys Glu Ser<br>           1770                      1775                  1780 | 5801 |
| gac agt tac agc gtc agc ccc tcg caa gac aca gat cga gca aga agc<br>Asp Ser Tyr Ser Val Ser Pro Ser Gln Asp Thr Asp Arg Ala Arg Ser<br>               1785                    1790                  1795 | 5849 |
| agc atg gtc tcc aca gaa agt gcc tcc tcc act tac gaa gaa ctg gcc<br>Ser Met Val Ser Thr Glu Ser Ala Ser Ser Thr Tyr Glu Glu Leu Ala<br>1800                     1805                    1810                    1815 | 5897 |
| agg gcc tac gaa cac gcc aag atg gaa gag caa ctg agg cac gcc aag<br>Arg Ala Tyr Glu His Ala Lys Met Glu Glu Gln Leu Arg His Ala Lys<br>    1820                          1825                    1830 | 5945 |
| ttc acc atc acg gag tgc ttc ata tca gac acg tca tcg gag cag ttg<br>Phe Thr Ile Thr Glu Cys Phe Ile Ser Asp Thr Ser Ser Glu Gln Leu<br>        1835                        1840                  1845 | 5993 |
| acg gca ggg aca aat gag tac acg gac agt ctg acc tcc agc acc cct<br>Thr Ala Gly Thr Asn Glu Tyr Thr Asp Ser Leu Thr Ser Ser Thr Pro<br>           1850                      1855                  1860 | 6041 |
| tcc gaa tcg gga atc tgc agg ttc act gca tct ccc ccc aaa cct cag<br>Ser Glu Ser Gly Ile Cys Arg Phe Thr Ala Ser Pro Pro Lys Pro Gln<br>               1865                    1870                    1875 | 6089 |
| gat gga gga aga gta atg aat atg gca gtt cca aag gca atc ggc cag<br>Asp Gly Gly Arg Val Met Asn Met Ala Val Pro Lys Ala Ile Gly Gln<br>1880                     1885                    1890                    1895 | 6137 |
| gtg acc tca tac att tgc ctc cat acc tta gaa tgg act ttt tgt<br>Val Thr Ser Tyr Ile Cys Leu His Thr Leu Glu Trp Thr Phe Cys<br>    1900                          1905                    1910 | 6182 |
| taaaccgagg tggtccaggc accagcaggg acctgagctt aggacaagca tgcttggaac | 6242 |
| ctcagaaaag ccggaccctg aagcgcccca cggtcctgga gcccatcccg atggaagccg | 6302 |
| cctcctccgc ctcctccacg agagaaggac agtcgtggca gccgggggcc gtggccacat | 6362 |
| tacctcagcg ggagggagca gagctgggac aggcagctaa aatgagcagc tcccaagaat | 6422 |
| cactgctcga ctcccggggc catttgaaag gaaacaatcc ttacgcaaaa tcttacaccc | 6482 |
| tggtataaca gacagcatga ctggacagcg gttgtaaata caattcaaac aattcaatca | 6542 |
| aagctacctt ttttttacgg aattccaata tttataatta aagaaaattg ccaaaatata | 6602 |
| tt | 6604 |

<210> SEQ ID NO 2
<211> LENGTH: 1910
<212> TYPE: PRT
<213> ORGANISM: HUMAN

<400> SEQUENCE: 2

Met Trp Ile Leu Ala Leu Ser Leu Phe Gln Ser Phe Ala Asn Val Phe
1               5                   10                 15

-continued

```
Ser Glu Asp Leu His Ser Ser Leu Tyr Phe Val Asn Ala Ser Leu Gln
         20                  25                  30

Glu Val Val Phe Ala Ser Thr Gly Thr Leu Val Pro Cys Pro Ala
         35                  40                  45

Ala Gly Ile Pro Pro Val Thr Leu Arg Trp Tyr Leu Ala Thr Gly Glu
         50                  55                  60

Glu Ile Tyr Asp Val Pro Gly Ile Arg His Val His Pro Asn Gly Thr
 65                  70                  75                  80

Leu Gln Ile Phe Pro Phe Pro Pro Ser Ser Phe Ser Thr Leu Ile His
                 85                  90                  95

Asp Asn Thr Tyr Tyr Cys Thr Ala Glu Asn Pro Ser Gly Lys Ile Arg
                 100                 105                 110

Ser Gln Asp Val His Ile Lys Ala Val Leu Arg Glu Pro Tyr Thr Val
         115                 120                 125

Arg Val Glu Asp Gln Lys Thr Met Arg Gly Asn Val Ala Val Phe Lys
         130                 135                 140

Cys Ile Ile Pro Ser Ser Val Glu Ala Tyr Ile Thr Val Val Ser Trp
145                 150                 155                 160

Glu Lys Asp Thr Val Ser Leu Val Ser Gly Ser Arg Phe Leu Ile Thr
                 165                 170                 175

Ser Thr Gly Ala Leu Tyr Ile Lys Asp Val Gln Asn Glu Asp Gly Leu
                 180                 185                 190

Tyr Asn Tyr Arg Cys Ile Thr Arg His Arg Tyr Thr Gly Glu Thr Arg
             195                 200                 205

Gln Ser Asn Ser Ala Arg Leu Phe Val Ser Asp Pro Ala Asn Ser Ala
         210                 215                 220

Pro Ser Ile Leu Asp Gly Phe Asp His Arg Lys Ala Met Ala Gly Gln
225                 230                 235                 240

Arg Val Glu Leu Pro Cys Lys Ala Leu Gly His Pro Glu Pro Asp Tyr
                 245                 250                 255

Arg Trp Leu Lys Asp Asn Met Pro Leu Glu Leu Ser Gly Arg Phe Gln
                 260                 265                 270

Lys Thr Val Thr Gly Leu Leu Ile Glu Asn Ile Arg Pro Ser Asp Ser
                 275                 280                 285

Gly Ser Tyr Val Cys Glu Val Ser Asn Arg Tyr Gly Thr Ala Lys Val
         290                 295                 300

Ile Gly Arg Leu Tyr Val Lys Gln Pro Leu Lys Ala Thr Ile Ser Pro
305                 310                 315                 320

Arg Lys Val Lys Ser Ser Val Gly Ser Gln Val Ser Leu Ser Cys Ser
                 325                 330                 335

Val Thr Gly Thr Glu Asp Gln Glu Leu Ser Trp Tyr Arg Asn Gly Glu
                 340                 345                 350

Ile Leu Asn Pro Gly Lys Asn Val Arg Ile Thr Gly Ile Asn His Glu
                 355                 360                 365

Asn Leu Ile Met Asp His Met Val Lys Ser Asp Gly Gly Ala Tyr Gln
         370                 375                 380

Cys Phe Val Arg Lys Asp Lys Leu Ser Ala Gln Asp Tyr Val Gln Val
385                 390                 395                 400

Val Leu Glu Asp Gly Thr Pro Lys Ile Ile Ser Ala Phe Ser Glu Lys
                 405                 410                 415

Val Val Ser Pro Ala Glu Pro Val Ser Leu Met Cys Asn Val Lys Gly
                 420                 425                 430

Thr Pro Leu Pro Thr Ile Thr Trp Thr Leu Asp Asp Asp Pro Ile Leu
```

-continued

```
            435                 440                 445
Lys Gly Gly Ser His Arg Ile Ser Gln Met Ile Thr Ser Glu Gly Asn
        450                 455                 460
Val Val Ser Tyr Leu Asn Ile Ser Ser Gln Val Arg Asp Gly Gly
465                 470                 475                 480
Val Tyr Arg Cys Thr Ala Asn Asn Ser Ala Gly Val Val Leu Tyr Gln
                485                 490                 495
Ala Arg Ile Asn Val Arg Gly Pro Ala Ser Ile Arg Pro Met Lys Asn
            500                 505                 510
Ile Thr Ala Ile Ala Gly Arg Asp Thr Tyr Ile His Cys Arg Val Ile
            515                 520                 525
Gly Tyr Pro Tyr Tyr Ser Ile Lys Trp Tyr Lys Asn Ser Asn Leu Leu
            530                 535                 540
Pro Phe Asn His Arg Gln Val Ala Phe Glu Asn Asn Gly Thr Leu Lys
545                 550                 555                 560
Leu Ser Asp Val Gln Lys Glu Val Asp Glu Gly Tyr Thr Cys Asn
                565                 570                 575
Val Leu Val Gln Pro Gln Leu Ser Thr Ser Gln Ser Val His Val Thr
                580                 585                 590
Val Lys Val Pro Pro Phe Ile Gln Pro Phe Glu Phe Pro Arg Phe Ser
            595                 600                 605
Ile Gly Gln Arg Val Phe Ile Pro Cys Val Val Ser Gly Asp Leu
            610                 615                 620
Pro Ile Thr Ile Thr Trp Gln Lys Asp Gly Arg Pro Ile Pro Gly Ser
625                 630                 635                 640
Leu Gly Val Thr Ile Asp Asn Ile Asp Phe Thr Ser Ser Leu Arg Ile
                645                 650                 655
Ser Asn Leu Ser Leu Met His Asn Gly Asn Tyr Thr Cys Ile Ala Arg
                660                 665                 670
Asn Glu Ala Ala Val Glu His Gln Ser Gln Leu Ile Val Arg Val
            675                 680                 685
Pro Pro Lys Phe Val Val Gln Pro Arg Asp Gln Asp Gly Ile Tyr Gly
            690                 695                 700
Lys Ala Val Ile Leu Asn Cys Ser Ala Glu Gly Tyr Pro Val Pro Thr
705                 710                 715                 720
Ile Val Trp Lys Phe Ser Lys Gly Ala Gly Val Pro Gln Phe Gln Pro
                725                 730                 735
Ile Ala Leu Asn Gly Arg Ile Gln Val Leu Ser Asn Gly Ser Leu Leu
            740                 745                 750
Ile Lys His Val Val Glu Glu Asp Ser Gly Tyr Tyr Leu Cys Lys Val
            755                 760                 765
Ser Asn Asp Val Gly Ala Asp Val Ser Lys Ser Met Tyr Leu Thr Val
770                 775                 780
Lys Ile Pro Ala Met Ile Thr Ser Tyr Pro Asn Thr Thr Leu Ala Thr
785                 790                 795                 800
Gln Gly Gln Lys Lys Glu Met Ser Cys Thr Ala His Gly Glu Lys Pro
                805                 810                 815
Ile Ile Val Arg Trp Glu Lys Glu Asp Arg Ile Ile Asn Pro Glu Met
                820                 825                 830
Ala Arg Tyr Leu Val Ser Thr Lys Glu Val Gly Glu Val Ile Ser
            835                 840                 845
Thr Leu Gln Ile Leu Pro Thr Val Arg Glu Asp Ser Gly Phe Phe Ser
            850                 855                 860
```

-continued

```
Cys His Ala Ile Asn Ser Tyr Gly Glu Asp Arg Gly Ile Ile Gln Leu
865                 870                 875                 880

Thr Val Gln Glu Pro Pro Asp Pro Glu Ile Glu Ile Lys Asp Val
            885                 890                 895

Lys Ala Arg Thr Ile Thr Leu Arg Trp Thr Met Gly Phe Asp Gly Asn
            900                 905                 910

Ser Pro Ile Thr Gly Tyr Asp Ile Glu Cys Lys Asn Lys Ser Asp Ser
            915                 920                 925

Trp Asp Ser Ala Gln Arg Thr Lys Asp Val Ser Pro Gln Leu Asn Ser
    930                 935                 940

Ala Thr Ile Ile Asp Ile His Pro Ser Ser Thr Tyr Ser Ile Arg Met
945                 950                 955                 960

Tyr Ala Lys Asn Arg Ile Gly Lys Ser Glu Pro Ser Asn Glu Leu Thr
                965                 970                 975

Ile Thr Ala Asp Glu Ala Ala Pro Asp Gly Pro Pro Gln Glu Val His
            980                 985                 990

Leu Glu Pro Ile Ser Ser Gln Ser Ile Arg Val Thr Trp Lys Ala Pro
            995                 1000                1005

Lys Lys His Leu Gln Asn Gly Ile Ile Arg Gly Tyr Gln Ile Gly Tyr
    1010                1015                1020

Arg Glu Tyr Ser Thr Gly Gly Asn Phe Gln Phe Asn Ile Ile Ser Val
025                 1030                1035                1040

Asp Thr Ser Gly Asp Ser Glu Val Tyr Thr Leu Asp Asn Leu Asn Lys
            1045                1050                1055

Phe Thr Gln Tyr Gly Leu Val Val Gln Ala Cys Asn Arg Ala Gly Thr
            1060                1065                1070

Gly Pro Ser Ser Gln Glu Ile Ile Thr Thr Thr Leu Glu Asp Val Pro
    1075                1080                1085

Ser Tyr Pro Pro Glu Asn Val Gln Ala Ile Ala Thr Ser Pro Glu Ser
    1090                1095                1100

Ile Ser Ile Ser Trp Ser Thr Leu Ser Lys Glu Ala Leu Asn Gly Ile
105                 1110                1115                1120

Leu Gln Gly Phe Arg Val Ile Tyr Trp Ala Asn Leu Met Asp Gly Glu
            1125                1130                1135

Leu Gly Glu Ile Lys Asn Ile Thr Thr Thr Gln Pro Ser Leu Glu Leu
            1140                1145                1150

Asp Gly Leu Glu Lys Tyr Thr Asn Tyr Ser Ile Gln Val Leu Ala Phe
    1155                1160                1165

Thr Arg Ala Gly Asp Gly Val Arg Ser Glu Gln Ile Phe Thr Arg Thr
1170                1175                1180

Lys Glu Asp Val Pro Gly Pro Pro Ala Gly Val Lys Ala Ala Ala Ala
185                 1190                1195                1200

Ser Ala Ser Met Val Phe Val Ser Trp Leu Pro Pro Leu Lys Leu Asn
            1205                1210                1215

Gly Ile Ile Arg Lys Tyr Thr Val Phe Cys Ser His Pro Tyr Pro Thr
            1220                1225                1230

Val Ile Ser Glu Phe Glu Ala Ser Pro Asp Ser Phe Ser Tyr Arg Ile
    1235                1240                1245

Pro Asn Leu Ser Arg Asn Arg Gln Tyr Ser Val Trp Val Val Ala Val
    1250                1255                1260

Thr Ser Ala Gly Arg Gly Asn Ser Ser Glu Ile Ile Thr Val Glu Pro
265                 1270                1275                1280
```

```
Leu Ala Lys Ala Pro Ala Arg Ile Leu Thr Phe Ser Gly Thr Val Thr
            1285                1290                1295

Thr Pro Trp Met Lys Asp Ile Val Leu Pro Cys Lys Ala Val Gly Asp
        1300                1305                1310

Pro Ser Pro Ala Val Lys Trp Met Lys Asp Ser Asn Gly Thr Pro Ser
    1315                1320                1325

Leu Val Thr Ile Asp Gly Arg Arg Ser Ile Phe Ser Asn Gly Ser Phe
1330                1335                1340

Ile Ile Arg Thr Val Lys Ala Glu Asp Ser Gly Tyr Tyr Ser Cys Ile
345                 1350                1355                1360

Ala Asn Asn Asn Trp Gly Ser Asp Glu Ile Ile Leu Asn Leu Gln Val
            1365                1370                1375

Gln Val Pro Pro Asp Gln Pro Arg Leu Thr Val Ser Lys Thr Thr Ser
        1380                1385                1390

Ser Ser Ile Thr Leu Ser Trp Leu Pro Gly Asp Asn Gly Gly Ser Ser
    1395                1400                1405

Ile Arg Gly Tyr Ile Leu Gln Tyr Ser Glu Asp Asn Ser Glu Gln Trp
1410                1415                1420

Gly Ser Phe Pro Ile Ser Pro Ser Glu Arg Ser Tyr Arg Leu Glu Asn
425                 1430                1435                1440

Leu Lys Cys Gly Thr Trp Tyr Lys Phe Thr Leu Thr Ala Gln Asn Gly
            1445                1450                1455

Val Gly Pro Gly Arg Ile Ser Glu Ile Ile Glu Ala Lys Thr Leu Gly
        1460                1465                1470

Lys Glu Pro Gln Phe Ser Lys Glu Gln Glu Leu Phe Ala Ser Ile Asn
    1475                1480                1485

Thr Thr Arg Val Arg Leu Asn Leu Ile Gly Trp Asn Asp Gly Gly Cys
1490                1495                1500

Pro Ile Thr Ser Phe Thr Leu Glu Tyr Arg Pro Phe Gly Thr Thr Val
505                 1510                1515                1520

Trp Thr Thr Ala Gln Arg Thr Ser Leu Ser Lys Ser Tyr Ile Leu Tyr
            1525                1530                1535

Asp Leu Gln Glu Ala Thr Trp Tyr Glu Leu Gln Met Arg Val Cys Asn
        1540                1545                1550

Ser Ala Gly Cys Ala Glu Lys Gln Ala Asn Phe Ala Thr Leu Asn Tyr
    1555                1560                1565

Asp Gly Ser Thr Ile Pro Pro Leu Ile Lys Ser Val Val Gln Asn Glu
1570                1575                1580

Glu Gly Leu Thr Thr Asn Glu Gly Leu Lys Met Leu Val Thr Ile Ser
585                 1590                1595                1600

Cys Ile Leu Val Gly Val Leu Leu Phe Val Leu Leu Leu Val Val
            1605                1610                1615

Arg Arg Arg Arg Arg Glu Gln Arg Leu Lys Arg Leu Arg Asp Ala Lys
        1620                1625                1630

Ser Leu Ala Glu Met Leu Met Ser Lys Asn Thr Arg Thr Ser Asp Thr
    1635                1640                1645

Leu Ser Lys Gln Gln Gln Thr Leu Arg Met His Ile Asp Ile Pro Arg
1650                1655                1660

Ala Gln Leu Leu Ile Glu Glu Arg Asp Thr Met Glu Thr Ile Asp Asp
665                 1670                1675                1680

Arg Ser Thr Val Leu Leu Thr Asp Ala Asp Phe Gly Glu Ala Ala Lys
            1685                1690                1695

Gln Lys Ser Leu Thr Val Thr His Thr Val His Tyr Gln Ser Val Ser
```

```
                    1700           1705           1710
Gln Ala Thr Gly Pro Leu Val Asp Val Ser Asp Ala Arg Pro Gly Thr
        1715           1720           1725
Asn Pro Thr Thr Arg Arg Asn Ala Lys Ala Gly Pro Thr Ala Arg Asn
    1730           1735           1740
Arg Tyr Ala Ser Gln Trp Thr Leu Asn Arg Pro His Pro Thr Ile Ser
745           1750           1755           1760
Ala His Thr Leu Thr Thr Asp Trp Arg Leu Pro Thr Pro Arg Ala Ala
            1765           1770           1775
Gly Ser Val Asp Lys Glu Ser Asp Ser Tyr Ser Val Ser Pro Ser Gln
            1780           1785           1790
Asp Thr Asp Arg Ala Arg Ser Ser Met Val Ser Thr Glu Ser Ala Ser
        1795           1800           1805
Ser Thr Tyr Glu Glu Leu Ala Arg Ala Tyr Glu His Ala Lys Met Glu
    1810           1815           1820
Glu Gln Leu Arg His Ala Lys Phe Thr Ile Thr Glu Cys Phe Ile Ser
825           1830           1835           1840
Asp Thr Ser Ser Glu Gln Leu Thr Ala Gly Thr Asn Glu Tyr Thr Asp
            1845           1850           1855
Ser Leu Thr Ser Ser Thr Pro Ser Glu Ser Gly Ile Cys Arg Phe Thr
            1860           1865           1870
Ala Ser Pro Pro Lys Pro Gln Asp Gly Gly Arg Val Met Asn Met Ala
        1875           1880           1885
Val Pro Lys Ala Ile Gly Gln Val Thr Ser Tyr Ile Cys Leu His Thr
    1890           1895           1900
Leu Glu Trp Thr Phe Cys
905               1910

<210> SEQ ID NO 3
<211> LENGTH: 388
<212> TYPE: DNA
<213> ORGANISM: Artificial Sequence
<220> FEATURE:
<223> OTHER INFORMATION: Description of Artificial Sequence:cDNA probe

<400> SEQUENCE: 3
ccgggtattc ttactcatga gcatttcagc taaactcttt gcatctcgca gcctctttag      60
cctctgctcc cgccgcctcc tccgcacaac cagcaggagc acaaacagca gcaagacccc     120
caccaggata caggagatgg tcaccagcat cttgagcccc tcgttggtcg tcagcccttc     180
ttcgttttgg acaactgact taatgagtgg aggaattgta ctgccatcgt agttcagcgt     240
agcgaagttg gcctgcttct ccgcgcagcc cgcactgttg cacacccgca tctgcagctc     300
ataccaggtg gcttcctgca ggtcatacag gatgtaggac ttggagagag aggtcctctg     360
agctgtggtc caaactgtgg tcccaaag                                       388

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:MboI linker
      sequence

<400> SEQUENCE: 4
cctgatgctc gagtgaattc                                                 20
```

```
<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 5
ccagttctca aaggagcagg                                                    20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 6
cctgtatgac ctgcaggaag                                                    20

<210> SEQ ID NO 7
<211> LENGTH: 842
<212> TYPE: DNA
<213> ORGANISM: MOUSE

<400> SEQUENCE: 7
ccgggccggg cgcggcggag cgcagcgcaa cgcgggggc gaggccggcg cgtggctcgc          60
tcgctggctc gctggctcgc gggaggccgg gcagcagcag gggcatgtgg atactggctc        120
tctccttgtt ccagagcttc gcgaatgttt tcagtgaaga gccccactcc agcctctact        180
ttgtcaatgc atcgctgcaa gaggtagtgt ttgcaagcac atcggggacg ctggtgccct        240
gcccggctgc aggcatccct cctgtgactc tcagatggta cctagcaacg ggcgaggaga        300
tctacgatgt ccccgggatc cgccacgtcc atcccaatgg cactctccaa attttccct         360 ttcctccttc aagcttcagc accttaatcc atgataatac ttactattgc acagctgaaa        420
acccttcagg gaaaattaga agtcaggatg tccacatcaa ggctgtttta cgggagccct        480
atacagtccg tgtggaggac cagaaaacca tgagaggcaa tgtcgcggtg ttcaagtgca        540
ttatcccctc ctcggtggag gcgtacgtct ctgtcgtctc atgggagaaa gacacggttt        600
cacttgtctc aggatctaga tttctcatca catccacggg agccttgtat attaaagatg        660
ttcagaacga agatgggctg tacaactacc gctgcatcgc gcggcacaga ttcgcggggg        720
agacgagaca gagcaactgc gcgagactgt tcgtgtcaga accagcaaac tcagcccatc        780
catcctggaa gggtttgacc accgccaaac catggccggg cacgcgtgga gctgccttgc        840
ca                                                                       842

<210> SEQ ID NO 8
<211> LENGTH: 898
<212> TYPE: DNA
<213> ORGANISM: MOUSE

<400> SEQUENCE: 8
tgccggccgg ttgcaagcct gtactacagg ccatactgcg tgaattatca ggttgtccag         60
ggtgtacact tcgctgtccc ggtggtgtca atactgatga tgttgaactg gaagttaccc        120
cgtgctgtac tccggtagcc tattggtagc cgcgaatgat cccgtcttgt atagtgttct        180
tgggagcctc tccaggtaac cctgatactc tgagatgagg tgggttccaa gtgaacttcc        240
tgaggtggac atcacgagct gcctcatccg ccgtgatggt gatctcgttg ctgggctcac        300
```

-continued

| | |
|---|---|
| tcttgccaat ccggttcttg gcgtacatgc ggatgctgta ggtggaggaa gggtggatat | 360 |
| caatgatggt ggccgagttc agctgagggg aaacatcttt ggttctctga gcagaatccc | 420 |
| acgagtctga tttatttttg cattcacact gtcatagcct gtgatggggc tgttgccatc | 480 |
| aaaccccatg gtccacctga gcgtgatggt gcgagctttg acatctcttg atctcaatct | 540 |
| cgggaggatc tggggttct tgcactgtga gttgaattat tccacggtcc tccccgtatg | 600 |
| aattgatagc atggcaggag aagaaaccgg aatcttctct cactgttggc aaaatctgca | 660 |
| gcgtagatat cacttcctct cccacctcct tggtggatac agtacgggcc acttcaggg | 720 |
| ttaatgatcc tgtctctctt ctccagcgga caatgatggg ctctcccatg ggctgtgcag | 780 |
| ctcattcctt cctttgaccc tgatggccag gtggtgtggg tataagttat atcatggccg | 840 |
| gaatttccct gtgagtccat ggacttgctg aacgttctgc gcccacatcg ttcgctga | 898 |

<210> SEQ ID NO 9
<211> LENGTH: 2173
<212> TYPE: DNA
<213> ORGANISM: MOUSE

<400> SEQUENCE: 9

| | |
|---|---|
| accaccattc acacacccag acatggcggg ttcgcggcaa ccttcagttc ctggccttcc | 60 |
| tgtagggtaa agggctgctg cgggtttata gaccggcaca tgcccatcct ggcatacggt | 120 |
| ggccagtggc tttccatctg gattccaggc caagctaaaa atctgttcct gatggccctg | 180 |
| cagtttcagc cgttcagctc cagtctgaag ttcccagatg cgaacggtta gatcatagga | 240 |
| actggaagcc agtacatcgg cagccagggg gtggaagcgc agagagtaga tcttttctgt | 300 |
| gtggcctgtg agcacagtct caggtgtggt gagaacattc tcgagccagc gagcgttcat | 360 |
| accgcttgga aaacctaaag tgtgggactt ggtataagtt cacccttact gcccaaaatg | 420 |
| gagtaggtcc cgggcgcata agtgaaatca tagaagccaa acccctgggg aaagaacccc | 480 |
| agttctccaa ggagcaggag cttttcgcca gcatcaatac cacccgagtg aggctgaatc | 540 |
| tgattggctg gaatgacggc ggctgtccaa tcacctcatt cactcttgaa tacagaccct | 600 |
| ttgggaccac ggtctggacc acagctcagc ggacctccct ttccaagtcc taacattctg | 660 |
| tatgacctgc aagaagccac gtggtatgaa ctgcagatga gagtgtgcaa cagcgccggc | 720 |
| tgtgcggata agcaagccaa cttcgccacg ctgaactacg atggcagtac aatccctcca | 780 |
| ctcattaagt cagttgtcca caaagcgaag aagggctgac aaccaacgaa gggctcaaga | 840 |
| tcctcgtgac catctcctgc atcctggtcg gggttctact gctctttgtg cttctgctgg | 900 |
| ttgtgcggag gagacggcga gagcagaggc tgaagaggct gagagatgca aagagtttag | 960 |
| ctgaaatgct catgagcaaa aacacacgga cttcagatac cttaagcaaa cagcagcaga | 1020 |
| cttttgagaat gcacattgat atacccaggg ctcagctttt gattgaagag agagacacaa | 1080 |
| tggagaccat agatgaccgc tccacagtcc tgttgacgga tgctgacttc ggggaggcag | 1140 |
| ccaaacagaa gtcactgaca gtgactcaca cggtgcatta ccaatcggtg tctcaggcca | 1200 |
| ccgggcccct cgtggatgtc tccgatgctc ggccaggaac gaatcccacc accaggagga | 1260 |
| atgcaaaggc tggacccaca gcgagaaacc ggtacgccag ccagtggacg ctcaacagac | 1320 |
| cccatcctac catctctgca cacaccctca ccacagaatg agactgctac accaggctac | 1380 |
| aggatccgtg acaggagagc gacagtacag cgtcagccca ttcacaagac acagacgagc | 1440 |
| aagaagcagc atgttctcca cagaaagtgc ttccttctac cacgaagact gccaggccta | 1500 |
| tgaacacgcc aagatggaag agcagctgag gcatgccaag ttcaccatca cagagtgctt | 1560 |

-continued

```
catatccgat acgtcctccg agcagttgac ggcaggacaa atgagtacac ggacagtctg    1620
actccagtac cccttcagaa tcgggatctg cagattcatg catctccccc caacctcagg    1680
atggaggacg agtgtgaaca tggcggttcc aaaggcccat cggccaggcg actcatacac    1740
ctgctccata cctacgatgg attcttgtta accgggcgc accaggcacc agcaggactg     1800
agtttaggac aagcgtgctt ggaaccccag aaagtcggac cctgaaacgc ccacgggtcg    1860
ttgagcccac ccctatggag gcctcctcct ccacttcttc cacgcgagaa ggacagcagt    1920
cgtggcaaca aggggctgtg gccaccttac ctcagcgaga gggtgcagag ctggacaggc    1980
agctaaaatg agcagctccc aagagtcact gctggactcc cgggccattg aaaggaacaa    2040
tccctacgca aatcttacac cttggtataa cacatggcac tgatggacag cggttgtaat    2100
acaattaacg agccaatcaa gctactttt tatgaattcc gatatttata attaagaatt     2160
gccaaatata tta                                                       2173

<210> SEQ ID NO 10
<211> LENGTH: 6413
<212> TYPE: DNA
<213> ORGANISM: HUMAN
<220> FEATURE:
<221> NAME/KEY: CDS
<222> LOCATION: (453)..(5165)

<400> SEQUENCE: 10
tgactgaggc cggagcacgg caaagatgag cctgcccgcc cgcctgctgc ctggatgcgg    60
agggtgaggg ctggcgcacg ggaggccgct ggctgcgcat tctgggcgcc gagtgcccgg    120
gatgagctca cgcccgcgtc tgcggctctc tccacctgcc gacctgccgg ggcccactg     180 agctgacggc gcacctgggc tccggccgca gcgtggggcg cggcgcccgg agcaggtgt     240 gcaggagcgc agcgcgcggc gagcgcagcc ctcgctccgg agcccggccg cgccgcgtgc    300
ccgggcggct aggcagcggc ggcggcggcg gcgggcggcg ggcgggcggc ggccccgggg    360
caggtgccga gcggcgagcg gagccggcc gggcggagcg cggggggcga ggccggcgcg     420
tcgctcgcgg gaggccgggg agcggcaggg gc atg tgg ata ctg gct ctc tcc    473
                                   Met Trp Ile Leu Ala Leu Ser
                                     1               5 ttg ttc cag agc ttc gcg aat gtt ttc agt gaa gac cta cac tcc agc    521
Leu Phe Gln Ser Phe Ala Asn Val Phe Ser Glu Asp Leu His Ser Ser
         10                  15                  20 ctc tac ttt gtc aat gca tct ctg caa gag gta gtg ttt gcc agc acc    569
Leu Tyr Phe Val Asn Ala Ser Leu Gln Glu Val Val Phe Ala Ser Thr
     25                  30                  35 acg ggg act ctg gtg ccc tgc ccc gca gca ggc atc cct cct gtg act    617
Thr Gly Thr Leu Val Pro Cys Pro Ala Ala Gly Ile Pro Pro Val Thr
 40                  45                  50                  55 ctc aga tgg tac cta gcc acg ggc gag gag atc tac gat gtc ccc ggg    665
Leu Arg Trp Tyr Leu Ala Thr Gly Glu Glu Ile Tyr Asp Val Pro Gly
                 60                  65                  70 atc cgc cac gtc cac ccc aac ggc act ctc caa att ttc ccc ttc cct    713
Ile Arg His Val His Pro Asn Gly Thr Leu Gln Ile Phe Pro Phe Pro
             75                  80                  85 cct tca agc ttc agt acc tta atc cat gat aat act tat tat tgc aca    761
Pro Ser Ser Phe Ser Thr Leu Ile His Asp Asn Thr Tyr Tyr Cys Thr
         90                  95                 100 gct gaa aat cct tca ggg aaa att aga agt cag gat gtc cac atc aag    809
Ala Glu Asn Pro Ser Gly Lys Ile Arg Ser Gln Asp Val His Ile Lys
    105                 110                 115
```

-continued

| | |
|---|---|
| gct gtt tta cgg gag ccc tat aca gtc cgt gtg gag gac cag aaa acc<br>Ala Val Leu Arg Glu Pro Tyr Thr Val Arg Val Glu Asp Gln Lys Thr<br>120                       125                    130                  135 | 857 |
| atg aga ggc aat gtt gcg gtc ttc aag tgc att atc ccc tcc tcg gtg<br>Met Arg Gly Asn Val Ala Val Phe Lys Cys Ile Ile Pro Ser Ser Val<br>                140                    145                    150 | 905 |
| gag gcg tac atc act gtc gtc tca tgg gag aaa gac act gtt tca ctt<br>Glu Ala Tyr Ile Thr Val Val Ser Trp Glu Lys Asp Thr Val Ser Leu<br>155                       160                    165 | 953 |
| gtc tca gga tct aga ttt ctc atc aca tcc acg gga gcc ttg tat att<br>Val Ser Gly Ser Arg Phe Leu Ile Thr Ser Thr Gly Ala Leu Tyr Ile<br>170                       175                    180 | 1001 |
| aaa gat gta cag aat gaa gat gga ttg tat aac tac cgc tgc atc acg<br>Lys Asp Val Gln Asn Glu Asp Gly Leu Tyr Asn Tyr Arg Cys Ile Thr<br>185                       190                    195 | 1049 |
| cgg cat cga tac acc gga gag acg agg cag agc aac agc gcc aga ctt<br>Arg His Arg Tyr Thr Gly Glu Thr Arg Gln Ser Asn Ser Ala Arg Leu<br>200                       205                    210                  215 | 1097 |
| ttt gta tca gac cca gcg aac tca gcc cca tcc ata ctg gat ggg ttt<br>Phe Val Ser Asp Pro Ala Asn Ser Ala Pro Ser Ile Leu Asp Gly Phe<br>                220                    225                    230 | 1145 |
| gac cat cgc aaa gcc atg gct ggg cag cgt gtg gag ctg cct tgc aaa<br>Asp His Arg Lys Ala Met Ala Gly Gln Arg Val Glu Leu Pro Cys Lys<br>235                       240                    245 | 1193 |
| gcg ctc ggg cac cct gag cca gat tac cgc tgg ctg aag gac aac atg<br>Ala Leu Gly His Pro Glu Pro Asp Tyr Arg Trp Leu Lys Asp Asn Met<br>250                       255                    260 | 1241 |
| ccc ctg gaa ctt tca ggg agg ttc cag aag acc gtg acg ggg ctg ctc<br>Pro Leu Glu Leu Ser Gly Arg Phe Gln Lys Thr Val Thr Gly Leu Leu<br>265                       270                    275 | 1289 |
| att gag aac att cgc ccc tcg gac tca ggc agc tat gtt tgt gaa gtg<br>Ile Glu Asn Ile Arg Pro Ser Asp Ser Gly Ser Tyr Val Cys Glu Val<br>280                       285                    290                  295 | 1337 |
| tcc aac aga tac gga act gct aag gtg ata ggc cgc ctg tac gtg aaa<br>Ser Asn Arg Tyr Gly Thr Ala Lys Val Ile Gly Arg Leu Tyr Val Lys<br>                300                    305                    310 | 1385 |
| cag cca ctg aaa gcc acc atc agt ccc agg aag gtt aaa agc agc gtg<br>Gln Pro Leu Lys Ala Thr Ile Ser Pro Arg Lys Val Lys Ser Ser Val<br>                315                    320                    325 | 1433 |
| ggt agc caa gtt tcc ttg tcc tgc agc gtg aca gga act gag gac cag<br>Gly Ser Gln Val Ser Leu Ser Cys Ser Val Thr Gly Thr Glu Asp Gln<br>330                       335                    340 | 1481 |
| gaa ctc tcc tgg tac cgc aat ggt gaa atc ctc aac cct gga aaa aat<br>Glu Leu Ser Trp Tyr Arg Asn Gly Glu Ile Leu Asn Pro Gly Lys Asn<br>345                       350                    355 | 1529 |
| gtg agg atc aca ggg atc aac cac gaa aac ctt ata atg gat cac atg<br>Val Arg Ile Thr Gly Ile Asn His Glu Asn Leu Ile Met Asp His Met<br>360                       365                    370                  375 | 1577 |
| gtc aaa agt gac ggg ggc gca tac cag tgc ttt gtg cgc aag gac aag<br>Val Lys Ser Asp Gly Gly Ala Tyr Gln Cys Phe Val Arg Lys Asp Lys<br>                380                    385                    390 | 1625 |
| ctg tcc gct caa gac tat gtg cag gtg gtc ctt gaa gat gga act ccc<br>Leu Ser Ala Gln Asp Tyr Val Gln Val Val Leu Glu Asp Gly Thr Pro<br>                395                    400                    405 | 1673 |
| aaa att att tct gcc ttt agt gaa aag gtg gtg agt cca gca gag ccg<br>Lys Ile Ile Ser Ala Phe Ser Glu Lys Val Val Ser Pro Ala Glu Pro<br>410                       415                    420 | 1721 |
| gtt tcc ctt atg tgc aac gtg aag gga aca cct ttg ccc acg atc acg<br>Val Ser Leu Met Cys Asn Val Lys Gly Thr Pro Leu Pro Thr Ile Thr | 1769 |

```
                425                 430                 435
tgg acc ctg gac gat gac ccg att ctc aag ggt ggc agt cac cgc atc       1817
Trp Thr Leu Asp Asp Asp Pro Ile Leu Lys Gly Gly Ser His Arg Ile
440                 445                 450                 455 agc cag atg atc acg tcg gag ggg aac gtg gtc agc tac ctg aac atc       1865
Ser Gln Met Ile Thr Ser Glu Gly Asn Val Val Ser Tyr Leu Asn Ile
                460                 465                 470 tcc agc tcc cag gtc cgg gac ggg gga gtc tac cgc tgc act gcc aac       1913
Ser Ser Ser Gln Val Arg Asp Gly Gly Val Tyr Arg Cys Thr Ala Asn
            475                 480                 485 aac tcg gcg gga gtc gtc ctg tac cag gct cga ata aac gta aga ggg       1961
Asn Ser Ala Gly Val Val Leu Tyr Gln Ala Arg Ile Asn Val Arg Gly
        490                 495                 500 cct gca agc att cga cca atg aaa aac atc aca gca ata gca gga cgg       2009
Pro Ala Ser Ile Arg Pro Met Lys Asn Ile Thr Ala Ile Ala Gly Arg
    505                 510                 515 gac aca tac att cac tgt cgt gtg att ggc tat ccg tat tac tcc att       2057
Asp Thr Tyr Ile His Cys Arg Val Ile Gly Tyr Pro Tyr Tyr Ser Ile
520                 525                 530                 535 aaa tgg tac aag aac tct aac ctg ctt cct ttc aac cac cgc caa gtg       2105
Lys Trp Tyr Lys Asn Ser Asn Leu Leu Pro Phe Asn His Arg Gln Val
                540                 545                 550 gca ttt gag aac aat gga act ctt aaa ctt tca gat gtg caa aag gaa       2153
Ala Phe Glu Asn Asn Gly Thr Leu Lys Leu Ser Asp Val Gln Lys Glu
            555                 560                 565 gtg gac gag ggg gag tac acg tgc aac gtg ttg gtt caa cca caa ctc       2201
Val Asp Glu Gly Glu Tyr Thr Cys Asn Val Leu Val Gln Pro Gln Leu
        570                 575                 580 tcc acc agc cag agc gtc cac gtg acc gtg aaa gtt ccg cct ttc ata       2249
Ser Thr Ser Gln Ser Val His Val Thr Val Lys Val Pro Pro Phe Ile
    585                 590                 595 caa ccc ttt gag ttt cca aga ttc tcc att ggg cag cgg gtc ttc atc       2297
Gln Pro Phe Glu Phe Pro Arg Phe Ser Ile Gly Gln Arg Val Phe Ile
600                 605                 610                 615 ccc tgt gtt gtg gtc tca ggg gac tta ccc atc acg atc acc tgg cag       2345
Pro Cys Val Val Val Ser Gly Asp Leu Pro Ile Thr Ile Thr Trp Gln
                620                 625                 630 aag gat ggc cgg cca atc cct ggg agc ctt ggg gtg acc att gac aat       2393
Lys Asp Gly Arg Pro Ile Pro Gly Ser Leu Gly Val Thr Ile Asp Asn
            635                 640                 645 att gac ttc acg agc tcc ttg agg att tcc aat ctc tcg ctc atg cac       2441
Ile Asp Phe Thr Ser Ser Leu Arg Ile Ser Asn Leu Ser Leu Met His
        650                 655                 660 aat ggg aat tac acc tgc ata gcc cgg aat gag gcc gct gtg gag       2489
Asn Gly Asn Tyr Thr Cys Ile Ala Arg Asn Glu Ala Ala Val Glu
    665                 670                 675 cac caa agc cag ttg att gtc aga gtt cct ccc aag ttt gtg gtt cag       2537
His Gln Ser Gln Leu Ile Val Arg Val Pro Pro Lys Phe Val Val Gln
680                 685                 690                 695 cca cgg gac cag gac ggg att tat ggc aaa gca gtc atc ctc aat tgt       2585
Pro Arg Asp Gln Asp Gly Ile Tyr Gly Lys Ala Val Ile Leu Asn Cys
                700                 705                 710 tct gct gag ggt tac cct gta cct acc atc gtg tgg aaa ttc tct aaa       2633
Ser Ala Glu Gly Tyr Pro Val Pro Thr Ile Val Trp Lys Phe Ser Lys
            715                 720                 725 ggt gct ggg gtt ccc cag ttc cag cca att gcc cta aat ggc cga atc       2681
Gly Ala Gly Val Pro Gln Phe Gln Pro Ile Ala Leu Asn Gly Arg Ile
        730                 735                 740 caa gtt ctc agc aat ggg tcg ttg ctg atc aag cat gtc gtg gag gaa       2729
```

```
Gln Val Leu Ser Asn Gly Ser Leu Leu Ile Lys His Val Glu Glu
    745                 750                 755 gac agt ggc tac tac ctc tgc aag gtc agc aac gat gtg ggc gca gac       2777
Asp Ser Gly Tyr Tyr Leu Cys Lys Val Ser Asn Asp Val Gly Ala Asp
760                 765                 770                 775 gtc agc aag tcc atg tac ctc acg gtt aaa att cct gcg atg ata aca       2825
Val Ser Lys Ser Met Tyr Leu Thr Val Lys Ile Pro Ala Met Ile Thr
                780                 785                 790 tcc tat cca aat act acc ctg gcc acg cag ggg cag aaa aag gag atg       2873
Ser Tyr Pro Asn Thr Thr Leu Ala Thr Gln Gly Gln Lys Lys Glu Met
            795                 800                 805 agc tgc acg gcg cat ggt gag aag ccc att ata gtc cgc tgg gag aag       2921
Ser Cys Thr Ala His Gly Glu Lys Pro Ile Ile Val Arg Trp Glu Lys
        810                 815                 820 gag gac cga atc att aac cct gag atg gcc cgt tat ctt gtg tcc acc       2969
Glu Asp Arg Ile Ile Asn Pro Glu Met Ala Arg Tyr Leu Val Ser Thr
    825                 830                 835 aag gag gtg gga gaa gag gtg att tct act ctg cag att ttg cca act       3017
Lys Glu Val Gly Glu Glu Val Ile Ser Thr Leu Gln Ile Leu Pro Thr
840                 845                 850                 855 gtg aga gaa gat tct ggt ttc ttt tcc tgc cat gct att aat tct tat       3065
Val Arg Glu Asp Ser Gly Phe Phe Ser Cys His Ala Ile Asn Ser Tyr
                860                 865                 870 ggg gag gac cgt gga ata att cag ctc aca gtg caa gag ccc cca gac       3113
Gly Glu Asp Arg Gly Ile Ile Gln Leu Thr Val Gln Glu Pro Pro Asp
            875                 880                 885 cct ccc gaa att gag atc aaa gat gtc aaa gca cgc aca att acg ctc       3161
Pro Pro Glu Ile Glu Ile Lys Asp Val Lys Ala Arg Thr Ile Thr Leu
        890                 895                 900 agg tgg acc atg ggg ttt gat gga aac agt ccc atc aca ggc tac gat       3209
Arg Trp Thr Met Gly Phe Asp Gly Asn Ser Pro Ile Thr Gly Tyr Asp
    905                 910                 915 att gaa tgc aaa aat aaa tca gac tcc tgg gat tct gct cag aga acc       3257
Ile Glu Cys Lys Asn Lys Ser Asp Ser Trp Asp Ser Ala Gln Arg Thr
920                 925                 930                 935 aaa gat gtt tcc cct cag ctg aac tcg gcc acc atc att gat atc cac       3305
Lys Asp Val Ser Pro Gln Leu Asn Ser Ala Thr Ile Ile Asp Ile His
                940                 945                 950 cct tcc tcc acc tac agc atc cgc atg tac gcc aag aac cgg att ggc       3353
Pro Ser Ser Thr Tyr Ser Ile Arg Met Tyr Ala Lys Asn Arg Ile Gly
            955                 960                 965 aag agc gag ccc agc aac gag ctc acc atc acg gcg gac gag gca gct       3401
Lys Ser Glu Pro Ser Asn Glu Leu Thr Ile Thr Ala Asp Glu Ala Ala
        970                 975                 980 cct gat ggt cca cct cag gaa gtt cac ctg gag cct ata tca tct cag       3449
Pro Asp Gly Pro Pro Gln Glu Val His Leu Glu Pro Ile Ser Ser Gln
    985                 990                 995 agc atc agg gtc aca tgg aag gct ccc aag aaa cat ttg caa aat ggg       3497
Ser Ile Arg Val Thr Trp Lys Ala Pro Lys Lys His Leu Gln Asn Gly
1000                1005                1010                1015 att atc cgt ggc tac caa ata ggt tac cga gag tac agc act ggg ggt       3545
Ile Ile Arg Gly Tyr Gln Ile Gly Tyr Arg Glu Tyr Ser Thr Gly Gly
                1020                1025                1030 aac ttc caa ttc aac att atc agt gtc gac acc agc ggg gac agt gag       3593
Asn Phe Gln Phe Asn Ile Ile Ser Val Asp Thr Ser Gly Asp Ser Glu
            1035                1040                1045 gtt tac acc ctg gac aac ctg aat aag ttc act cag tac ggc ctg gtg       3641
Val Tyr Thr Leu Asp Asn Leu Asn Lys Phe Thr Gln Tyr Gly Leu Val
        1050                1055                1060
```

```
gtg cag gcc tgt aac cgg gcc ggc acg ggg cct tct tct cag gaa atc       3689
Val Gln Ala Cys Asn Arg Ala Gly Thr Gly Pro Ser Ser Gln Glu Ile
    1065                1070                1075 atc acc acc act ctc gag gat gtg ccc agt tac ccc ccc gaa aat gtc       3737
Ile Thr Thr Thr Leu Glu Asp Val Pro Ser Tyr Pro Pro Glu Asn Val
1080                1085                1090                1095 caa gcc ata gca aca tca cca gaa agc ata tca ata tcc tgg tcc aca       3785
Gln Ala Ile Ala Thr Ser Pro Glu Ser Ile Ser Ile Ser Trp Ser Thr
                1100                1105                1110 ctt tcc aag gaa gcc ttg aat gga att ctc cag ggg ttc aga gtc att       3833
Leu Ser Lys Glu Ala Leu Asn Gly Ile Leu Gln Gly Phe Arg Val Ile
            1115                1120                1125 tac tgg gcc aac ctc atg gac gga gag ctg ggt gag att aaa aac atc       3881
Tyr Trp Ala Asn Leu Met Asp Gly Glu Leu Gly Glu Ile Lys Asn Ile
        1130                1135                1140 acc acc aca cag cct tca ctg gag ctg gac ggg ctg gaa aag tac acc       3929
Thr Thr Thr Gln Pro Ser Leu Glu Leu Asp Gly Leu Glu Lys Tyr Thr
    1145                1150                1155 aac tac agc atc cag gtg ctg gcc ttc acc cgc gca gga gac ggg gtc       3977
Asn Tyr Ser Ile Gln Val Leu Ala Phe Thr Arg Ala Gly Asp Gly Val
1160                1165                1170                1175 agg agt gag cag atc ttc acc cgg acc aaa gag gat gtt cca ggt cct       4025
Arg Ser Glu Gln Ile Phe Thr Arg Thr Lys Glu Asp Val Pro Gly Pro
                1180                1185                1190 ccc gcg ggt gtg aag gca gcg gcg gcc tca gcc tcc atg gtc ttt gtg       4073
Pro Ala Gly Val Lys Ala Ala Ala Ala Ser Ala Ser Met Val Phe Val
            1195                1200                1205 tcc tgg ctt ccc cct ctc aag ctg aac ggc atc atc cga aag tac act       4121
Ser Trp Leu Pro Pro Leu Lys Leu Asn Gly Ile Ile Arg Lys Tyr Thr
        1210                1215                1220 gta ttc tgc tcc cac ccc tat ccc aca gtg atc agc gag ttt gag gcc       4169
Val Phe Cys Ser His Pro Tyr Pro Thr Val Ile Ser Glu Phe Glu Ala
    1225                1230                1235 tct ccc gac tcg ttt tcc tac aga att ccc aac ctg agt agg aat cgt       4217
Ser Pro Asp Ser Phe Ser Tyr Arg Ile Pro Asn Leu Ser Arg Asn Arg
1240                1245                1250                1255 cag tac agc gtc tgg gtg gtg gct gtt act tca gcc gga aga ggc aac       4265
Gln Tyr Ser Val Trp Val Val Ala Val Thr Ser Ala Gly Arg Gly Asn
                1260                1265                1270 agc agt gaa atc atc aca gtc gag cca cta gca aaa gct cct gca cga       4313
Ser Ser Glu Ile Ile Thr Val Glu Pro Leu Ala Lys Ala Pro Ala Arg
            1275                1280                1285 atc ctg acc ttc agt ggg aca gtg act act cca tgg atg aaa gac att       4361
Ile Leu Thr Phe Ser Gly Thr Val Thr Thr Pro Trp Met Lys Asp Ile
        1290                1295                1300 gtc ttg cct tgt aag gct gtt ggg gac cct tct cct gca gtc aaa tgg       4409
Val Leu Pro Cys Lys Ala Val Gly Asp Pro Ser Pro Ala Val Lys Trp
    1305                1310                1315 atg aaa gac agt aac ggg aca ccc agt cta gta acg att gat ggg cgg       4457
Met Lys Asp Ser Asn Gly Thr Pro Ser Leu Val Thr Ile Asp Gly Arg
1320                1325                1330                1335 agg agc atc ttt agc aac gga agc ttc att att cgc acg gtg aaa gca       4505
Arg Ser Ile Phe Ser Asn Gly Ser Phe Ile Ile Arg Thr Val Lys Ala
                1340                1345                1350 gaa gac tcc ggc tat tac agc tgc att gcc aat aac aac tgg gga tct       4553
Glu Asp Ser Gly Tyr Tyr Ser Cys Ile Ala Asn Asn Asn Trp Gly Ser
            1355                1360                1365 gat gaa att att tta aac tta caa gta caa gtt cca cca gat cag cct       4601
Asp Glu Ile Ile Leu Asn Leu Gln Val Gln Val Pro Pro Asp Gln Pro
        1370                1375                1380
```

-continued

| | |
|---|---|
| cgg ctt aca gtc tcc aag acc acg tct tcc tcc atc acc ctt tct tgg<br>Arg Leu Thr Val Ser Lys Thr Thr Ser Ser Ser Ile Thr Leu Ser Trp<br>    1385                     1390                     1395 | 4649 |
| ctc cct gga gac aac ggg ggc agc tct atc aga gga tac ata ctg cag<br>Leu Pro Gly Asp Asn Gly Gly Ser Ser Ile Arg Gly Tyr Ile Leu Gln<br>1400                 1405                 1410                 1415 | 4697 |
| tac tcc gag gac aat agt gag cag tgg ggg agt ttt cca atc agc ccc<br>Tyr Ser Glu Asp Asn Ser Glu Gln Trp Gly Ser Phe Pro Ile Ser Pro<br>    1420                     1425                     1430 | 4745 |
| agc gaa cgt tcc tat cgc ttg gaa aat ctc aaa tgt ggg act tgg tat<br>Ser Glu Arg Ser Tyr Arg Leu Glu Asn Leu Lys Cys Gly Thr Trp Tyr<br>         1435                 1440                 1445 | 4793 |
| aag ttc aca ctg aca gcc caa aat gga gtg ggc cca ggg cgc ata agt<br>Lys Phe Thr Leu Thr Ala Gln Asn Gly Val Gly Pro Gly Arg Ile Ser<br>        1450                 1455                 1460 | 4841 |
| gaa atc ata gaa gca aag acc tta gga aaa gag ccc cag ttc tca aag<br>Glu Ile Ile Glu Ala Lys Thr Leu Gly Lys Glu Pro Gln Phe Ser Lys<br>1465                 1470                 1475 | 4889 |
| gag cag gag ctg ttt gcc agc atc aac acc aca cgc gtg agg ctg aac<br>Glu Gln Glu Leu Phe Ala Ser Ile Asn Thr Thr Arg Val Arg Leu Asn<br>1480                 1485                 1490                 1495 | 4937 |
| ctc att ggc tgg aat gat ggc ggc tgc ccc atc acc tcc ttc aca cta<br>Leu Ile Gly Trp Asn Asp Gly Gly Cys Pro Ile Thr Ser Phe Thr Leu<br>                1500                 1505                 1510 | 4985 |
| gag tac agg ccc ttt ggg acc aca gtt tgg acc aca gct cag agg acc<br>Glu Tyr Arg Pro Phe Gly Thr Thr Val Trp Thr Thr Ala Gln Arg Thr<br>    1515                     1520                     1525 | 5033 |
| tct ctc tcc aag tcc tac atc ctg tat gac ctg cag gaa gcc acc tgg<br>Ser Leu Ser Lys Ser Tyr Ile Leu Tyr Asp Leu Gln Glu Ala Thr Trp<br>         1530                 1535                 1540 | 5081 |
| tat gag ctg cag atg cgg gtg tgc aac agt gcg ggc tgc gcg gag aag<br>Tyr Glu Leu Gln Met Arg Val Cys Asn Ser Ala Gly Cys Ala Glu Lys<br>             1545                 1550                 1555 | 5129 |
| cag gct aaa gag gct gcg aga tgc aaa gag ttt agc tgaaatgctc<br>Gln Ala Lys Glu Ala Ala Arg Cys Lys Glu Phe Ser<br>1560                 1565                 1570 | 5175 |
| atgagtaaga ataccccggac ttcagatacg ttaagcaagc aacagcagac cctgcgaatg | 5235 |
| cacatcgaca tacccagggc tcagcttttg attgaagaga gagacacgat ggagaccatt | 5295 |
| gatgatcgct ccacggttct gttgacggat gctgactttg gagaggcagc taagcagaag | 5355 |
| tccctgacgg tcactcacac ggtccattac caatcggtgt ctcaggccac tgggcccttg | 5415 |
| gtggatgttt cagacgctcg gccgggaacg aatcccacca ccaggaggaa tgccaaggct | 5475 |
| gggcccacag cgagaaaccg ctatgccagc cagtggaccc tcaaccgacc caccccacc | 5535 |
| atctcagcac acaccctcac cacagactgg aggctgccaa cacccagggc tgcaggatca | 5595 |
| gtagacaaag agagcgacag ttacagcgtc agccctcgc aagacacaga tcgagcaaga | 5655 |
| agcagcatgg tctccacaga aagtgcctcc tccacttacg aagaactggc cagggcctac | 5715 |
| gaacacgcca agatggaaga gcaactgagg cacgccaagt tcaccatcac ggagtgcttc | 5775 |
| atatcagaca cgtcatcgga gcagttgacg gcagggacaa atgagtacac ggacagtctg | 5835 |
| acctccagca ccccttccga atcgggaatc tgcaggttca ctgcatctcc ccccaaacct | 5895 |
| caggatggag gaagagtaat gaatatggca gttccaaagg caatcggcca ggtgacctca | 5955 |
| tacatttgcc tccataacctt agaatggact ttttgttaaa ccgaggtggt ccaggcacca | 6015 |
| gcagggacct gagcttagga caagcatgct tggaaccctca gaaaagccgg accctgaagc | 6075 |

-continued

```
gccccacggt cctggagccc atcccgatgg aagccgcctc ctccgcctcc tccacgagag      6135
aaggacagtc gtggcagccg ggggccgtgg ccacattacc tcagcgggag ggagcagagc      6195
tgggacaggc agctaaaatg agcagctccc aagaatcact gctcgactcc cggggccatt      6255
tgaaaggaaa caatccttac gcaaaatctt acaccctggt ataacagaca gcatgactgg      6315
acagcggttg taaatacaat tcaaacaatt caatcaaagc tacctttttt ttacggaatt      6375
ccaatattta taattaaaga aaattgccaa aatatatt                              6413
```

<210> SEQ ID NO 11
<211> LENGTH: 1571
<212> TYPE: PRT
<213> ORGANISM: HUMAN

<400> SEQUENCE: 11

```
Met Trp Ile Leu Ala Leu Ser Leu Phe Gln Ser Phe Ala Asn Val Phe
1               5                   10                  15

Ser Glu Asp Leu His Ser Ser Leu Tyr Phe Val Asn Ala Ser Leu Gln
            20                  25                  30

Glu Val Val Phe Ala Ser Thr Thr Gly Thr Leu Val Pro Cys Pro Ala
        35                  40                  45

Ala Gly Ile Pro Pro Val Thr Leu Arg Trp Tyr Leu Ala Thr Gly Glu
    50                  55                  60

Glu Ile Tyr Asp Val Pro Gly Ile Arg His Val His Pro Asn Gly Thr
65                  70                  75                  80

Leu Gln Ile Phe Pro Phe Pro Pro Ser Ser Phe Ser Thr Leu Ile His
                85                  90                  95

Asp Asn Thr Tyr Tyr Cys Thr Ala Glu Asn Pro Ser Gly Lys Ile Arg
            100                 105                 110

Ser Gln Asp Val His Ile Lys Ala Val Leu Arg Glu Pro Tyr Thr Val
        115                 120                 125

Arg Val Glu Asp Gln Lys Thr Met Arg Gly Asn Val Ala Val Phe Lys
    130                 135                 140

Cys Ile Ile Pro Ser Ser Val Glu Ala Tyr Ile Thr Val Val Ser Trp
145                 150                 155                 160

Glu Lys Asp Thr Val Ser Leu Val Ser Gly Ser Arg Phe Leu Ile Thr
                165                 170                 175

Ser Thr Gly Ala Leu Tyr Ile Lys Asp Val Gln Asn Glu Asp Gly Leu
            180                 185                 190

Tyr Asn Tyr Arg Cys Ile Thr Arg His Arg Tyr Thr Gly Glu Thr Arg
        195                 200                 205

Gln Ser Asn Ser Ala Arg Leu Phe Val Ser Asp Pro Ala Asn Ser Ala
    210                 215                 220

Pro Ser Ile Leu Asp Gly Phe Asp His Arg Lys Ala Met Ala Gly Gln
225                 230                 235                 240

Arg Val Glu Leu Pro Cys Lys Ala Leu Gly His Pro Glu Pro Asp Tyr
                245                 250                 255

Arg Trp Leu Lys Asp Asn Met Pro Leu Glu Leu Ser Gly Arg Phe Gln
            260                 265                 270

Lys Thr Val Thr Gly Leu Leu Ile Glu Asn Ile Arg Pro Ser Asp Ser
        275                 280                 285

Gly Ser Tyr Val Cys Glu Val Ser Asn Arg Tyr Gly Thr Ala Lys Val
    290                 295                 300

Ile Gly Arg Leu Tyr Val Lys Gln Pro Leu Lys Ala Thr Ile Ser Pro
305                 310                 315                 320
```

-continued

```
Arg Lys Val Lys Ser Ser Val Gly Ser Gln Val Ser Leu Ser Cys Ser
                325                 330                 335

Val Thr Gly Thr Glu Asp Gln Glu Leu Ser Trp Tyr Arg Asn Gly Glu
            340                 345                 350

Ile Leu Asn Pro Gly Lys Asn Val Arg Ile Thr Gly Ile Asn His Glu
            355                 360                 365

Asn Leu Ile Met Asp His Met Val Lys Ser Asp Gly Ala Tyr Gln
370                 375                 380

Cys Phe Val Arg Lys Asp Lys Leu Ser Ala Gln Asp Tyr Val Gln Val
385                 390                 395                 400

Val Leu Glu Asp Gly Thr Pro Lys Ile Ile Ser Ala Phe Ser Glu Lys
                405                 410                 415

Val Val Ser Pro Ala Glu Pro Val Ser Leu Met Cys Asn Val Lys Gly
                420                 425                 430

Thr Pro Leu Pro Thr Ile Thr Trp Thr Leu Asp Asp Asp Pro Ile Leu
            435                 440                 445

Lys Gly Gly Ser His Arg Ile Ser Gln Met Ile Thr Ser Glu Gly Asn
            450                 455                 460

Val Val Ser Tyr Leu Asn Ile Ser Ser Ser Gln Val Arg Asp Gly Gly
465                 470                 475                 480

Val Tyr Arg Cys Thr Ala Asn Asn Ser Ala Gly Val Val Leu Tyr Gln
                485                 490                 495

Ala Arg Ile Asn Val Arg Gly Pro Ala Ser Ile Arg Pro Met Lys Asn
                500                 505                 510

Ile Thr Ala Ile Ala Gly Arg Asp Thr Tyr Ile His Cys Arg Val Ile
            515                 520                 525

Gly Tyr Pro Tyr Tyr Ser Ile Lys Trp Tyr Lys Asn Ser Asn Leu Leu
            530                 535                 540

Pro Phe Asn His Arg Gln Val Ala Phe Glu Asn Asn Gly Thr Leu Lys
545                 550                 555                 560

Leu Ser Asp Val Gln Lys Glu Val Asp Glu Gly Glu Tyr Thr Cys Asn
                565                 570                 575

Val Leu Val Gln Pro Gln Leu Ser Thr Ser Gln Ser Val His Val Thr
            580                 585                 590

Val Lys Val Pro Pro Phe Ile Gln Pro Phe Glu Phe Pro Arg Phe Ser
            595                 600                 605

Ile Gly Gln Arg Val Phe Ile Pro Cys Val Val Ser Gly Asp Leu
            610                 615                 620

Pro Ile Thr Ile Thr Trp Gln Lys Asp Gly Arg Pro Ile Pro Gly Ser
625                 630                 635                 640

Leu Gly Val Thr Ile Asp Asn Ile Asp Phe Thr Ser Ser Leu Arg Ile
                645                 650                 655

Ser Asn Leu Ser Leu Met His Asn Gly Asn Tyr Thr Cys Ile Ala Arg
                660                 665                 670

Asn Glu Ala Ala Ala Val Glu His Gln Ser Gln Leu Ile Val Arg Val
                675                 680                 685

Pro Pro Lys Phe Val Val Gln Pro Arg Asp Gln Asp Gly Ile Tyr Gly
            690                 695                 700

Lys Ala Val Ile Leu Asn Cys Ser Ala Glu Gly Tyr Pro Val Pro Thr
705                 710                 715                 720

Ile Val Trp Lys Phe Ser Lys Gly Ala Gly Val Pro Gln Phe Gln Pro
                725                 730                 735
```

-continued

Ile Ala Leu Asn Gly Arg Ile Gln Val Leu Ser Asn Gly Ser Leu Leu
                740                 745                 750

Ile Lys His Val Val Glu Glu Asp Ser Gly Tyr Tyr Leu Cys Lys Val
            755                 760                 765

Ser Asn Asp Val Gly Ala Asp Val Ser Lys Ser Met Tyr Leu Thr Val
        770                 775                 780

Lys Ile Pro Ala Met Ile Thr Ser Tyr Pro Asn Thr Thr Leu Ala Thr
785                 790                 795                 800

Gln Gly Gln Lys Lys Glu Met Ser Cys Thr Ala His Gly Glu Lys Pro
                805                 810                 815

Ile Ile Val Arg Trp Glu Lys Glu Asp Arg Ile Ile Asn Pro Glu Met
            820                 825                 830

Ala Arg Tyr Leu Val Ser Thr Lys Glu Val Gly Glu Glu Val Ile Ser
        835                 840                 845

Thr Leu Gln Ile Leu Pro Thr Val Arg Glu Asp Ser Gly Phe Phe Ser
    850                 855                 860

Cys His Ala Ile Asn Ser Tyr Gly Glu Asp Arg Gly Ile Ile Gln Leu
865                 870                 875                 880

Thr Val Gln Glu Pro Pro Asp Pro Pro Glu Ile Glu Ile Lys Asp Val
                885                 890                 895

Lys Ala Arg Thr Ile Thr Leu Arg Trp Thr Met Gly Phe Asp Gly Asn
            900                 905                 910

Ser Pro Ile Thr Gly Tyr Asp Ile Glu Cys Lys Asn Lys Ser Asp Ser
        915                 920                 925

Trp Asp Ser Ala Gln Arg Thr Lys Asp Val Ser Pro Gln Leu Asn Ser
    930                 935                 940

Ala Thr Ile Ile Asp Ile His Pro Ser Ser Thr Tyr Ser Ile Arg Met
945                 950                 955                 960

Tyr Ala Lys Asn Arg Ile Gly Lys Ser Glu Pro Ser Asn Glu Leu Thr
                965                 970                 975

Ile Thr Ala Asp Glu Ala Ala Pro Asp Gly Pro Pro Gln Glu Val His
            980                 985                 990

Leu Glu Pro Ile Ser Ser Gln Ser Ile Arg Val Thr Trp Lys Ala Pro
        995                 1000                1005

Lys Lys His Leu Gln Asn Gly Ile Ile Arg Gly Tyr Gln Ile Gly Tyr
    1010                1015                1020

Arg Glu Tyr Ser Thr Gly Gly Asn Phe Gln Phe Asn Ile Ile Ser Val
025                 1030                1035                1040

Asp Thr Ser Gly Asp Ser Glu Val Tyr Thr Leu Asp Asn Leu Asn Lys
                1045                1050                1055

Phe Thr Gln Tyr Gly Leu Val Val Gln Ala Cys Asn Arg Ala Gly Thr
            1060                1065                1070

Gly Pro Ser Ser Gln Glu Ile Ile Thr Thr Thr Leu Glu Asp Val Pro
        1075                1080                1085

Ser Tyr Pro Pro Glu Asn Val Gln Ala Ile Ala Thr Ser Pro Glu Ser
    1090                1095                1100

Ile Ser Ile Ser Trp Ser Thr Leu Ser Lys Glu Ala Leu Asn Gly Ile
105                 1110                1115                1120

Leu Gln Gly Phe Arg Val Ile Tyr Trp Ala Asn Leu Met Asp Gly Glu
                1125                1130                1135

Leu Gly Glu Ile Lys Asn Ile Thr Thr Thr Gln Pro Ser Leu Glu Leu
            1140                1145                1150

Asp Gly Leu Glu Lys Tyr Thr Asn Tyr Ser Ile Gln Val Leu Ala Phe

-continued

```
                1155                1160                1165
Thr Arg Ala Gly Asp Gly Val Arg Ser Glu Gln Ile Phe Thr Arg Thr
    1170                1175                1180

Lys Glu Asp Val Pro Gly Pro Ala Gly Val Lys Ala Ala Ala Ala
185                 1190                1195                1200

Ser Ala Ser Met Val Phe Val Ser Trp Leu Pro Pro Leu Lys Leu Asn
                1205                1210                1215

Gly Ile Ile Arg Lys Tyr Thr Val Phe Cys Ser His Pro Tyr Pro Thr
                1220                1225                1230

Val Ile Ser Glu Phe Glu Ala Ser Pro Asp Ser Phe Ser Tyr Arg Ile
                1235                1240                1245

Pro Asn Leu Ser Arg Asn Arg Gln Tyr Ser Val Trp Val Val Ala Val
                1250                1255                1260

Thr Ser Ala Gly Arg Gly Asn Ser Ser Glu Ile Ile Thr Val Glu Pro
265                 1270                1275                1280

Leu Ala Lys Ala Pro Ala Arg Ile Leu Thr Phe Ser Gly Thr Val Thr
                1285                1290                1295

Thr Pro Trp Met Lys Asp Ile Val Leu Pro Cys Lys Ala Val Gly Asp
                1300                1305                1310

Pro Ser Pro Ala Val Lys Trp Met Lys Asp Ser Asn Gly Thr Pro Ser
                1315                1320                1325

Leu Val Thr Ile Asp Gly Arg Arg Ser Ile Phe Ser Asn Gly Ser Phe
                1330                1335                1340

Ile Ile Arg Thr Val Lys Ala Glu Asp Ser Gly Tyr Tyr Ser Cys Ile
345                 1350                1355                1360

Ala Asn Asn Asn Trp Gly Ser Asp Glu Ile Ile Leu Asn Leu Gln Val
                1365                1370                1375

Gln Val Pro Pro Asp Gln Pro Arg Leu Thr Val Ser Lys Thr Thr Ser
                1380                1385                1390

Ser Ser Ile Thr Leu Ser Trp Leu Pro Gly Asp Asn Gly Gly Ser Ser
                1395                1400                1405

Ile Arg Gly Tyr Ile Leu Gln Tyr Ser Glu Asp Asn Ser Glu Gln Trp
                1410                1415                1420

Gly Ser Phe Pro Ile Ser Pro Ser Glu Arg Ser Tyr Arg Leu Glu Asn
425                 1430                1435                1440

Leu Lys Cys Gly Thr Trp Tyr Lys Phe Thr Leu Thr Ala Gln Asn Gly
                1445                1450                1455

Val Gly Pro Gly Arg Ile Ser Glu Ile Ile Glu Ala Lys Thr Leu Gly
                1460                1465                1470

Lys Glu Pro Gln Phe Ser Lys Glu Gln Glu Leu Phe Ala Ser Ile Asn
                1475                1480                1485

Thr Thr Arg Val Arg Leu Asn Leu Ile Gly Trp Asn Asp Gly Gly Cys
                1490                1495                1500

Pro Ile Thr Ser Phe Thr Leu Glu Tyr Arg Pro Phe Gly Thr Thr Val
505                 1510                1515                1520

Trp Thr Thr Ala Gln Arg Thr Ser Leu Ser Lys Ser Tyr Ile Leu Tyr
                1525                1530                1535

Asp Leu Gln Glu Ala Thr Trp Tyr Glu Leu Gln Met Arg Val Cys Asn
                1540                1545                1550
```

```
Ser Ala Gly Cys Ala Glu Lys Gln Ala Lys Glu Ala Ala Arg Cys Lys
    1555            1560            1565

Glu Phe Ser
    1570
```

NUCLEIC ACID ENCODING DS-CAM PROTEINS AND PRODUCTS RELATED THERETO

This is a non-provisional application based on, and claims the benefit of, U.S. Provisional Application No. 60/029,322 filed Oct. 25, 1996 the content of which is incorporated herein by reference in its entirety.

ACKNOWLEDGMENT

This invention was made with Government support under Grant Numbers HL50025 and HD17449 awarded by the National Institutes of Health and DE-FG03-92ER61402 awarded by the Department of Energy. The Government has certain rights in this invention.

FIELD OF THE INVENTION

The present invention relates to nucleic acids and proteins encoded thereby. Invention nucleic acids encode a novel N-CAM member of the immunoglobulin superfamily of proteins. The invention also relates to methods for making and using such nucleic acids and proteins.

BACKGROUND OF THE INVENTION

Research spanning the last decade has significantly elucidated the molecular events attending cell-cell interactions in the body, especially those events involved in the movement and activation of cells in the immune system. See generally, Springer et al., Nature 346:425–434, 1990. Cell surface proteins, and especially the so-called cellular Adhesion Molecules ("CAMs") have correspondingly been the subject of pharmaceutical research and development having as its goal intervening in the processes of leukocyte extravasation to sites of inflammation and leukocyte movement to distinct target tissues. The isolation and characterization of cellular adhesion molecules, the cloning and expression of DNA sequences encoding such molecules, and the development of therapeutic and diagnostic agents relevant to inflammatory process, viral infection and cancer metastasis have also been the subject of numerous U.S. and foreign applications for Letters Patent. See Edwards, Current Opinion in Therapeutic Patents 1(11):1617–1630, 1991 and particularly the published "patent literature references" cited therein.

Numerous CAMs have been characterized to date. See, for example, vascular adhesion molecule (VCAM-1) as described in PCT WO 90/13300; platelet endothelial cell adhesion molecule (PECAM-1) described in Newman et al., Science 247:1219–1222, 1990; and PCT WO 91/10683; and the following U.S. Pat. Nos.: 5,525,487; 5,235,049; 5,272, 263; 5,489,233; 5,264,554; 5,318,890; 5,389,520; 5,519, 008; and the like.

There is substantial evidence that N-CAM and its relatives play an important part in neural development (Edelman and Crossin, "CELL ADHESION MOLECULES: Implications for a Molecular Histology", Ann. Rev. Biochem. 60:155–190, 1991; and Walsh and Doherty, Curr. Opinion in Cell Biol. 5:791–796, 1993). For example, antibodies directed against N-CAMs disturbed the normal growth pattern of nerve processes. N-CAM (locus 11q23.1) is expressed in large amounts in cells of the developing neural tube, but when neural crest cells dissociate from the neural tube and migrate away, they lose N-CAM, only to reexpress it later when they reaggregate to form a neural ganglion. In addition, Rosenthal et al., (Nature Genet. 2:107–112, 1992) reported that mutations in CAM-L1 (locus Xq28) cause X-linked hydrocephalus, and Jouet et al., (Nature Genet. 7:402–407, 1994) showed that mutations in CAM L1 gene are responsible for type 1 X-linked spastic paraplegia and MASA syndrome which shows agenesis of the corpus callosum. Therefore, there is a need in the art to identify and isolate novel N-CAM members of the immunoglobulin superfamily so that their role in neural development and neural cell communication can be determined.

Therefore, there continues to be a need in the art for the discovery of additional proteins participating in human cell-cell interactions and especially a need for information serving to specifically identify and characterize such proteins in terms of their amino acid sequence. Moreover, to the extent that such molecules might form the basis for the development of therapeutic and diagnostic agents, it is essential that the DNA encoding them be elucidated. The present invention satisfies this need and provides related advantages as well.

BRIEF DESCRIPTION OF THE INVENTION

In accordance with the present invention, there are provided isolated nucleic acids encoding novel mammalian N-CAM (neural-cell adhesion molecule) members of the immunoglobulin superfamily of proteins, referred to herein as Down Syndrome-Cell Adhesion Molecules (DS-CAMs). Further provided are vectors containing invention nucleic acids, probes that hybridize thereto, host cells transformed therewith, antisense oligonucleotides thereto and related compositions. The nucleic acid molecules described herein can be incorporated into a variety of recombinant expression systems known to those of skill in the art to readily produce isolated DS-CAM proteins. In addition, the nucleic acid molecules of the present invention are useful as probes for assaying for the presence and/or amount of a DS-CAM gene or mRNA transcript in a given sample. The nucleic acid molecules described herein, and oligonucleotide fragments thereof, are also useful as primers and/or templates in a PCR reaction for amplifying genes encoding DS-CAM proteins.

In accordance with the present invention, there are also provided isolated mammalian DS-CAM proteins. These proteins are useful, for example, in neural prosthetic devices used in entubulation methods of repairing (regenerating) damaged or severed peripheral nerves (see, e.g., U.S. Pat. No. 4,955,892, incorporated herein by reference). In addition, these proteins, or fragments thereof, are useful as immunogens for producing anti-DS-CAM antibodies, or in therapeutic compositions containing such proteins and/or antibodies. Invention DS-CAM proteins are also useful in bioassays to identify agonists and antagonists thereto. Also provided are transgenic non-human mammals that express the invention protein.

Antibodies that are immunoreactive with invention DS-CAM proteins are also provided. These antibodies are useful in diagnostic assays to determine levels of DS-CAM proteins present in a given sample, e.g., tissue samples, Western blots, and the like. The antibodies can also be used to purify DS-CAM proteins from crude cell extracts and the like. Moreover, these antibodies are considered therapeutically useful to counteract or supplement the biological effect of DS-CAMs in vivo.

Methods and diagnostic systems for determining the levels of DS-CAM protein in various tissue samples are also provided. These diagnostic methods can be used for monitoring the level of therapeutically administered DS-CAM protein or fragments thereof to facilitate the maintenance of therapeutically effective amounts. These diagnostic methods can also be used to diagnose physiological disorders that result from abnormal levels or abnormal structures of the DS-CAM protein.

Immunoglobulin type C2-domain. FbN: Fibronmection type III domain. The bold Cs in the amino acid sequence indicates Cysteine residues forming disulfide bonds in the Ig-like type-C2 domains. The bold NXS and NXT in the amino acid sequence correspond to potential N-glycosylation sites.

Figure 3:
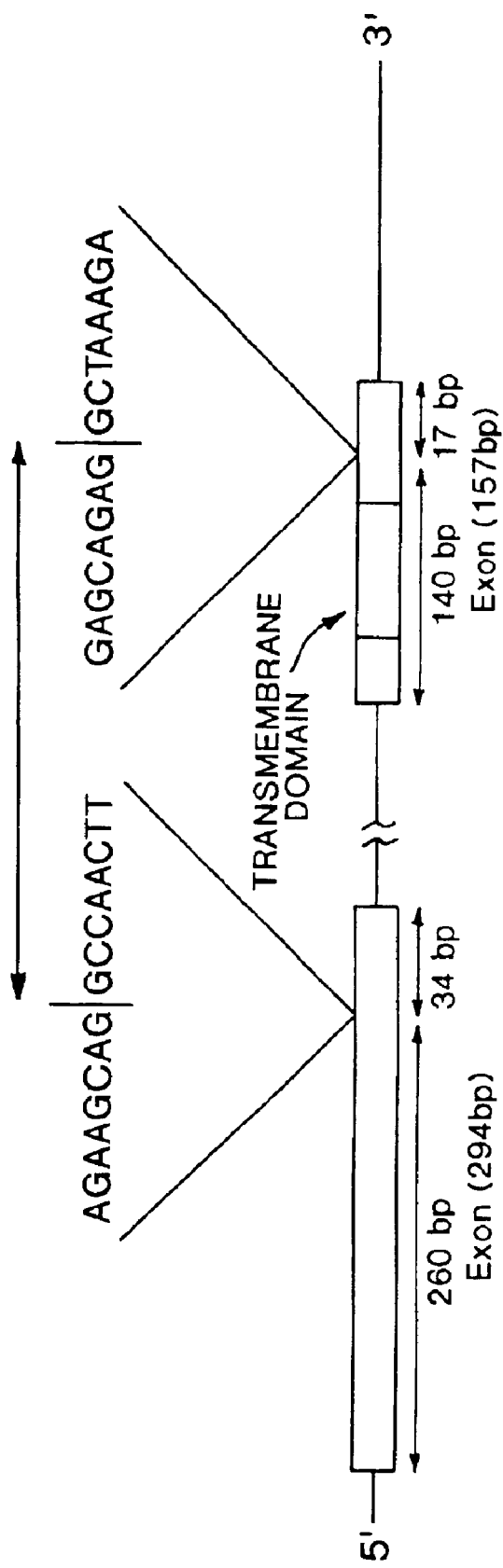

FIG. 3 shows a partial genomic structure of DS-CAM1 and a deletion contained in DS-CAM2 cDNA clones (clones pDS-CAM-18 and pDS-CAM-52). The deletion boundary sequence (GC-AG) suggests an unusual alternative splicing. The horizontal bar represents genomic sequence containing exons of DS-CAM-42. Exons are indicated by open boxes. Exon-intron boundaries are defined by a comparison of the cDNA sequence of pDS-CAM-42 and genomic sequence determined from a BAC clone.

Figure 4:
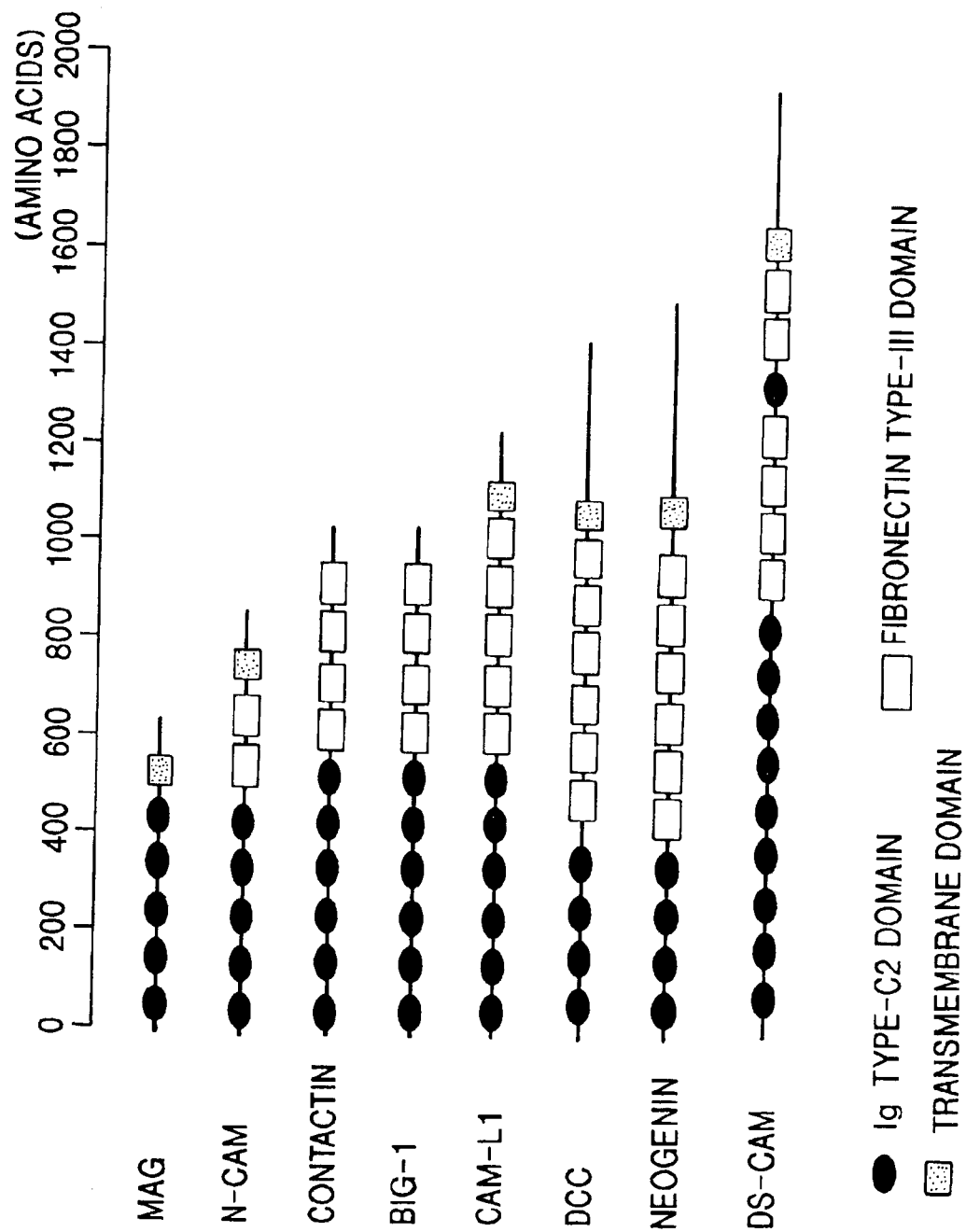

FIG. 4 shows a schematic comparison of neuronal Ig superfamily members. Ig-like type C-2 domains, fibronectin type III domains and transmembrane domains are indicated. MAG: myelin-associated glycoprotein, N-CAM: neural cell adhesion molecule, BIG-1: brain-derived immunoglobulin (Ig) superfamily molecule-1, DCC: deleted in colorectal carcinoma.

DETAILED DESCRIPTION OF THE INVENTION

In accordance with the present invention, there are provided isolated nucleic acids, which encode novel mammalian members of the DS-CAM family of proteins, and fragments thereof. The phrase "DS-CAM" refers to substantially pure native DS-CAM protein, or recombinantly produced proteins, including naturally occurring allelic variants thereof encoded by mRNA generated by alternative splicing of a primary transcript, such as DS-CAM1 (SEQ ID NO:2) and DS-CAM2 (SEQ ID NO:11) disclosed herein, and further including fragments thereof which retain at least one native biological activity, such as immunogenicity. In one aspect, invention DS-CAM proteins, such as DS-CAM1, are cell-surface glycoproteins that are mobile in the plane of the membrane. Invention DS-CAM1 proteins contain extra- and intra-cellular domains that transduce information from the outside of the cell to the cytoplasm and the nucleus, thereby determining cell function. In another aspect, invention DS-CAM proteins, such as DS-CAM2, are non-membrane bound, soluble proteins.

In one aspect of the invention DS-CAM proteins are further characterized as comprising at least 7 Immunoglobulin-like (Ig-like) domains homologous to the immunoglobulin superfamily and 6 type III fibronectin repeats (see, e.g., Edelman and Crossin, "CELL ADHESION MOLECULES: Implications for a Molecular Histology", Ann. Rev. Biochem., 60:155–190, 1991; and Walsh and Doherty, Curr. Opinion in Cell Biol., 5:791–796, 1993; each of which is incorporated herein by reference in its entirety). In another aspect of the invention, DS-CAM proteins are those proteins comprising at least 8, preferably at least 9 Ig-like domains, with at least 10 Ig-like domains being especially preferred.

As used herein, "Ig-like domains", or 115 grammatical variations thereof, refers to the well known repeats that are common among Cell Adhesion Molecules (CAMs)(see, e.g., FIG. 1A at p. 158 of Edelman and Crossin, supra, 1991; and Walsh and Doherty, supra, 1993; each of which is incorporated herein by reference in its entirety).

The phrase "type III fibronectin repeats", "fibronectin repeats," or grammatical variations thereof, refers to the well known repeats that are common among Cell Adhesion Molecules (CAMs)(see, e.g., FIG. 1A at p. 158 of Edelman and Crossin, supra, 1991; and Walsh and Doherty, supra, 1993; each of which is incorporated herein by reference in its entirety).

The invention DS-CAM proteins define a novel sub-class of the Ig (immunoglobulin) superfamily with highest homologies to the neural cell adhesion molecules including BIG-1 (Yoshihara et al., Neuron 13:415–426, 1994), CAM-L1 (Moos et al., Nature 334:701–703, 1988), DCC (Fearon et al., Science 247:49–56, 1990), neogenin (Lane et al., Genomics 35:456–465, 1996), and contactin (Ranscht, J. Cell Bio. 107:1561–1573, 1988) (FIG. 4). It has been found that the structure of invention DS-CAM proteins is unique within the neural immunoglobulin superfamily, and is distinctive due to the number of Ig-like type C2 and fibronectin III domains (10 and 6 respectively) and from the interruption of the fourth and fifth fibronectin domains by a lath C2 domain, the functional significance of which may be of interest. The novel structure of DS-CAM and its expression throughout the nervous system during differentiation suggest interesting roles for the neural CAM in neural development and function. The location of DS-CAM in a region critical for DS neurocognitive phenotypes provides a human model in which to test the significance of these roles for cognitive function.

The neural Ig-superfamily members play critical roles in neural development and function and have been implicated in cell migration and sorting, axon guidance and fasciculation, formation of neural connections, and in synaptic plasticity (Edelman and Crossin, supra, 1991; Walsh and Doherty, supra, 1993; Tessier-Lavigne et al., Science 274:1123–1133, 1996: Shuster et al. Neuron 17:641–654, 1996: Shuster et al. Neuron 17:655–657, 1996). These activities are mediated by the homophilic or heterophilic binding properties of Ig-superfamily members (Mauro et al., J. Cell Bio. 119:191–202, 1992 and Milev et al., J. Biol. Chem. 271:15716–15723, 1996), the binding of Ig-superfamily proteins to extracellular matrix proteins (Grumet et al., Cell Adhesion Comm. 1:177–190, 1993; Taira et al., Neuron 12 :861–872, 1994; and Zisch et al., J. Cell Bio. 119:203–213, 1992), and the binding to smaller diffusible chemorepellents or chemoattractants, for example, DCC and netrin (Keino-Masu et al., Cell 87:175–185, 1996).

The specificity of DS-CAM expression for the central nervous system and the timing of its expression to the period of neurite outgrowth in both the central and peripheral nervous systems, indicates a role for DS-CAM in early development and differentiation (Examples 4 and 5). Early in development when, with the exception of neural crest precursors, expression is clearly absent from regions that contain dividing neuroepithelial precursors such as the ependymal layer of the neural tube and the ventricular zone of the brain (Altman and Bayer, *Atlas of Prenatal Rat Brain Development*, CRC Press, Ann Arbor, Mich., 1995). In the embryo, differentiated neurons express DS-CAM when they have finished migrating to their proper positions within the neuroepithelium, during neurite outgrowth.

Neural crest cells may express DS-CAM while they are migrating. At 15.5 and 16.5 days pc, most of the neural crest derived tissues have some expression, although not all have finished migration. The continued expression of DS-CAM in the myenteric plexus after 15.5–16.5 dpc is due to the neural crest cells that have stopped dividing, although others are in the cell cycle. Approximately 50% of myenteric ganglia neurons arise after birth and DS-CAM may be expressed later in this subset. At later stages, the data suggest that DS-CAM is down regulated in the neural crest derivatives such as the myenteric ganglia and ganglia of the pancreas. The DS-CAM expression in tissues derived from the neural crest is of interest with respect to the high level detected in the umbilical cord. The tissue surrounding the umbilical artery and vein is derived from the neural crest and functions in coordinating the cardiovascular changes occurring at birth. The expression detected in the fetal liver and branchial arches is also derived from neural crest related to the ductus venosus and ultimately the ductus arteriosus and cardiac outflow tracts, respectively.

DS-CAM expression continues post-natally, in the differentiating regions of the newborn brain, such as, the septum and inferior colliculus, and in the adult in regions associated with plasticity, such as, the olfactory bulb and hippocampus. When combined with the evidence for involvement of the Ig superfamily in determining synaptic strength (Mayford et al., *Science* 256:638–644, 1992), the continued expression supports a role for DS-CAM in remodeling, learning and memory. The expression pattern and the role of dendritic connections in cell body maintenance indicate that an increase in DS-CAM expression in DS brain is responsible in part for the abnormalities of dendritic structure and decreased intersections seen at four months post-natal in DS individuals.

Alternatively spliced variants of CAMs have distinct roles in different parts of the brain, as demonstrated for closely related Ig-superfamily members, such as, NCAM (Cunningham et al., *Science* 236:799–806, 1987 and Figarella-Branger et al., *J. Neuropathol. Exp. Neurol.* 51:12–23, 1992). The differential expression of alternatively spliced DS-CAM transcripts encoding DS-CAM1 (SEQ ID NO:2) and DS-CAM2 (SEQ ID NO:11) has likewise been observed in various parts of the human adult brain. For example, it has been found that DS-CAM clones encoding DS-CAM2 contain a small deletion relative to DS-CAM1, which deletion contains the transmembrane domain (Example 3 and FIG. 3) and results in a stop codon 36 bp downstream. The results of RT-PCR (Example 5) indicated that all RNAs tested from various human tissues expressed both the DS-CAM1 and DS-CAM2 transcripts and that the PCR products generated the sequence and size predicted for the appropriate form. The proximal and distal borders of the deletion are located within neighboring exons and reveal variant consensus splice site sequences (Jackson, *Nuc. Acid Res.* 19:3795–3798, 1991) with further surrounding homology to the U1 spliceosome RNA.

From Northern analyses (Example 4) a minimum of three distinct transcripts are recognized by a probe for the transmembrane domain. From cDNA sequence analyses (Example 5) two forms of the DS-CAM protein are deduced, one that generates a transmembrane adhesion molecule and a second that is deleted for the transmembrane domain, thereby generating a molecule that is transported to the extracellular matrix. This mode of generating extracellular and membrane bound forms of CAMs is in surprising contrast to the GPI (glycosylphosphatidylinositol) linkage used by most CAMS, and would provide a way of generating longer range homophilic interactions between cells and the extracellular matrix, which may be significant for cell migration.

Figure 1:
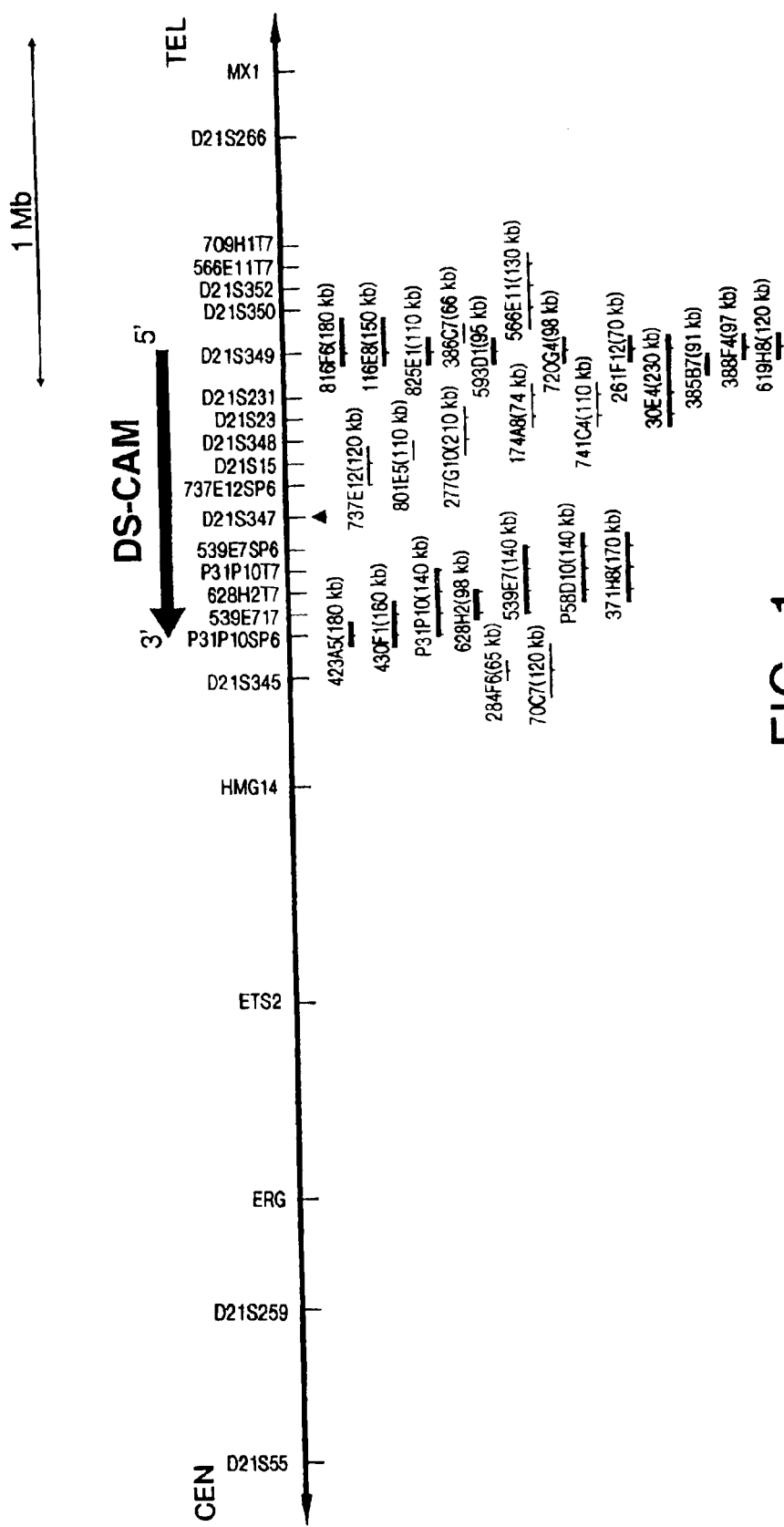
FIG. 1 shows a physical map of the localization of the DS-CAM gene to a region between D21S345 and D21S347 on chromosome 21. The locations of BAC clones (starting with numbers) and PAC clones (starting with "P") are indicated by horizontal bars. An arrow head indicates a gap in the BAC and PAC contig. The location of the DS-CAM gene is indicated by a thick arrow.

The DS-CAM gene was isolated (as described in the Examples hereinafter) by using the BAC contig on 21q22.2–q22.3 covering the region between D21S55 and MX1 (Hubert et al., *Genomics* 41:218–226, 1997). The gene spans a minimum of 900 kb, estimated by summing the size of BACs and PACs that are non-overlapping and covered by the DS-CAM gene (FIG. 1). The DS-CAM gene covers a gap in all physical maps of this region. From hybridization experiments indicating no signal of the complete cDNA to BAC 277G10 covering 210 kb, a 5' intron is at least this size, similar to the first intron of the DCC gene (Cho et al., *Genomics* 19:525–531, 1994). Alternatively, other alternative transcripts can contain exons located in this BAC. The gene spans the boundary of bands 21q22.2 and q22.3, a Giemsa-dark and Giemsa-light band, respectively. The location of the gene for PEP19, a small 634 bp gene with large introns within the same band 21q22.2 (Cabin et al., *Somat. Cell Mol. Genet.* 22:167–175, 1996) suggests a general structure of genes in G-bands having large introns.

The nucleic acid molecules described herein are useful for producing invention DS-CAM proteins, when such nucleic acids are incorporated into a variety of protein expression systems known to those of skill in the art. In addition, such nucleic acid molecules or fragments thereof can be labeled with a readily detectable substituent and used as hybridization probes for assaying for the presence and/or amount of a DS-CAM gene or mRNA transcript in a given sample. The nucleic acid molecules described herein, and fragments thereof, are also useful as primers and/or templates in a PCR reaction for amplifying genes encoding the invention protein described herein.

The term "nucleic acid" (also referred to as polynucleotides) encompasses ribonucleic acid (RNA) or deoxyribonucleic acid (DNA), probes, oligonucleotides, and primers. DNA can be either complementary DNA (cDNA) or genomic DNA, e.g. a gene encoding a DS-CAM protein. One means of isolating a nucleic acid encoding a DS-CAM polypeptide is to probe a mammalian genomic library with a natural or artificially designed DNA probe using methods well known in the art. DNA probes derived from the DS-CAM gene are particularly useful for this purpose. DNA and cDNA molecules that encode DS-CAM polypeptides can be used to obtain complementary genomic DNA, cDNA or RNA from mammalian (e.g., human, mouse, rat, rabbit, pig, and the like), or other animal sources, or to isolate related cDNA or genomic clones by the screening of cDNA or genomic libraries, by methods described in more detail below. Examples of nucleic acids are RNA, cDNA, or isolated genomic DNA encoding a DS-CAM polypeptide. Such nucleic acids may include, but are not limited to, nucleic acids having substantially the same nucleotide sequence as set forth in SEQ ID NO:1, SEQ ID NO:7, SEQ ID NO:8, SEQ ID NO:9, SEQ ID NO:10, or at least nucleotides 453–6185 set forth in SEQ ID NO:1, or nucleotides 453–5168 set forth in SEQ ID NO:10.

Use of the terms "isolated" and/or "purified" in the present specification and claims as a modifier of DNA, RNA, polypeptides or proteins means that the DNA, RNA, polypeptides or proteins so designated have been produced in such form by the hand of man, and thus are separated from their native in vivo cellular environment. As a result of this human intervention, the recombinant DNAs, RNAs, polypeptides and proteins of the invention are useful in ways described herein that the DNAs, RNAs, polypeptides or proteins as they naturally occur are not.

As used herein, "mammalian" refers to the variety of species from which the invention DS-CAM protein is derived, e.g., human, rat, mouse, rabbit, monkey, baboon, bovine, porcine, ovine, canine, feline, and the like. A preferred DS-CAM protein herein, is human DS-CAM.

In one embodiment of the present invention, cDNAs encoding the invention DS-CAM proteins disclosed herein include substantially the same nucleotide sequence as set forth in SEQ ID NO:1, SEQ ID NO:7, SEQ ID NO:8, SEQ ID NO:9, or SEQ ID NO:10. Preferred cDNA molecules encoding the invention proteins include the same nucleotide sequence as nucleotides 453–6185 set forth in SEQ ID NO:1, or nucleotides 453–5168 set forth in SEQ ID NO:10.

As employed herein, the term "substantially the same nucleotide sequence" refers to DNA having sufficient identity to the reference polynucleotide, such that it will hybridize to the reference nucleotide under moderately stringent hybridization conditions. In one embodiment, DNA having substantially the same nucleotide sequence as the reference nucleotide sequence encodes substantially the same amino acid sequence as that set forth in SEQ ID NO:2 or SEQ ID NO:11, or the DS-CAM coding region of SEQ ID NO:7, SEQ ID NO:8 or SEQ ID NO:9, or a larger amino acid sequence including SEQ ID NO:2 or SEQ ID NO:11, or the DS-CAM coding region of SEQ ID NO:7, SEQ ID NO:8 or SEQ ID NO:9. In another embodiment, DNA having "substantially the same nucleotide sequence" as the reference nucleotide sequence has at least 60% identity with respect to the reference nucleotide sequence. DNA having at least 70%, more preferably at least 90%, yet more preferably at least 95%, identity to the reference nucleotide sequence is preferred.

This invention also encompasses nucleic acids which differ from the nucleic acids shown in SEQ ID NO:1, SEQ ID NO:7, SEQ ID NO:8, SEQ ID NO:9, SEQ ID NO:10 but which have the same phenotype. Phenotypically similar nucleic acids are also referred to as "functionally equivalent nucleic acids". As used herein, the phrase "functionally equivalent nucleic acids" encompasses nucleic acids characterized by slight and non-consequential sequence variations that will function in substantially the same manner to produce the same protein product(s) as the nucleic acids disclosed herein. In particular, functionally equivalent nucleic acids encode polypeptides that are the same as those disclosed herein or that have conservative amino acid variations, or that encode larger polypeptides that includes SEQ ID NO:2 or SEQ ID NO:11, or the DS-CAM coding region of SEQ ID NO:7, SEQ ID NO:8 or SEQ ID NO:9. For example, conservative variations include substitution of a non-polar residue with another non-polar residue, or substitution of a charged residue with a similarly charged residue. These variations include those recognized by skilled artisans as those that do not substantially alter the tertiary structure of the protein.

Further provided are nucleic acids encoding DS-CAM polypeptides that, by virtue of the degeneracy of the genetic code, do not necessarily hybridize to the invention nucleic acids under specified hybridization conditions. Preferred nucleic acids encoding the invention polypeptides are comprised of nucleotides that encode substantially the same amino acid sequences set forth in SEQ ID NO:2 or SEQ ID NO:11, or the DS-CAM coding region of SEQ ID NO:7, SEQ ID NO:8 or SEQ ID NO:9.

Thus, an exemplary nucleic acid encoding an invention DS-CAM protein may be selected from:
(a) DNA encoding the amino acid sequence set forth in SEQ ID NO:2 or SEQ ID NO:11, or the DS-CAM coding region of SEQ ID NO:7, SEQ ID NO:8 or SEQ ID NO:9,
(b) DNA that hybridizes to the DNA of (a) under moderately stringent conditions, wherein said DNA encodes biologically active DS-CAM, or
(c) DNA degenerate with respect to either (a) or (b) above, wherein said DNA encodes biologically active DS-CAM.

Hybridization refers to the binding of complementary strands of nucleic acid (i.e., sense:antisense strands or probe:target-DNA) to each other through hydrogen bonds, similar to the bonds that naturally occur in chromosomal DNA. Stringency levels used to hybridize a given probe with target-DNA can be readily varied by those of skill in the art.

The phrase "stringent hybridization" is used herein to refer to conditions under which polynucleic acid hybrids are stable. As known to those of skill in the art, the stability of hybrids is reflected in the melting temperature ($T_m$) of the hybrids. In general, the stability of a hybrid is a function of sodium ion concentration and temperature. Typically, the hybridization reaction is performed under conditions of lower stringency, followed by washes of varying, but higher, stringency. Reference to hybridization stringency relates to such washing conditions.

As used herein, the phrase "moderately stringent hybridization" refers to conditions that permit target-DNA to bind a complementary nucleic acid that has about 60% identity, preferably about 75% identity, more preferably about 85% identity to the target DNA; with greater than about 90% identity to target-DNA being especially preferred. Preferably, moderately stringent conditions are conditions equivalent to hybridization in 50% formamide, 5× Denhardt's solution, 5×SSPE, 0.2% SDS at 42° C., followed by washing in 0.2×SSPE, 0.2% SDS, at 65° C.

The phrase "high stringency hybridization" refers to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). High stringency conditions can be provided, for example, by hybridization in 50% formamide, 5× Denhardt's solution, 5×SSPE, 0.2% SDS at 42° C., followed by washing in 0.1×SSPE, and 0.1% SDS at 65° C.

The phrase "low stringency hybridization" refers to conditions equivalent to hybridization in 10% formamide, 5× Denhardt's solution, 6×SSPE, 0.2% SDS at 42° C., followed by washing in 1×SSPE, 0.2% SDS, at 50° C. Denhardt's solution and SSPE (see, e.g., Sambrook et al., *Molecular Cloning, A Laboratory Manual*, Cold Spring Harbor Laboratory Press, 1989) are well known to those of skill in the art as are other suitable hybridization buffers.

As used herein, the term "degenerate" refers to codons that differ in at least one nucleotide from a reference nucleic acid, e.g., SEQ ID NO:1, but encode the same amino acids as the reference nucleic acid. For example, codons specified by the triplets "UCU", "UCC", "UCA", and "UCG" are degenerate with respect to each other since all four of these codons encode the amino acid serine.

Preferred nucleic acids encoding the invention polypeptide(s) hybridize under moderately stringent, preferably high stringency, conditions to substantially the entire sequence, or in certain embodiments substantial portions (i.e., typically at least 15–30 nucleotides) of the nucleic acid sequence set forth in SEQ ID NO:1, SEQ ID NO:7, SEQ ID NO:8, SEQ ID NO:9 or SEQ ID NO:10.

The invention nucleic acids can be produced by a variety of methods well-known in the art, e.g., the methods described herein, employing PCR amplification using oligonucleotide primers from various regions of SEQ ID NO:1, SEQ ID NO:7, SEQ ID NO:8, SEQ ID NO:9, SEQ ID NO:10, and the like.

In accordance with a further embodiment of the present inventions optionally labeled DS-CAM-encoding cDNAs, or fragments thereof, can be employed to probe library(ies) (e.g., cDNA, genomic, and the like) for additional nucleic acid sequences encoding novel mammalian DS-CAM proteins. As described in Example 3, construction of mammalian cDNA libraries, preferably a human trisomy 21 fetal brain cDNA library, is well-known in the art. Screening of such a cDNA library is initially carried out under low-stringency conditions, which comprise a temperature of less than about 42° C., a formamide concentration of less than about 50%, and a moderate to low salt concentration.

Presently preferred probe-based screening conditions comprise a temperature of about 37° C., a formamide concentration of about 20%, and a salt concentration of about SX standard saline citrate (SSC; 20×SSC contains 3M sodium chloride, 0.3M sodium citrate, pH 7.0). Such conditions will allow the identification of sequences which have a substantial degree of similarity with the probe sequence, without requiring perfect homology. The phrase "substantial similarity" refers to sequences which share at least 50% homology. Preferably, hybridization conditions will be selected which allow the identification of sequences having at least 70% homology with the probe, while discriminating against sequences which have a lower degree of homology with the probe. As a result, nucleic acids having substantially the same nucleotide sequence as nucleotides 453–6185 set forth in SEQ ID NO:1, or nucleotides 453–5168 set forth in SEQ ID NO:10, SEQ ID NO:7, SEQ ID NO:8, or SEQ ID NO:9 are obtained.

As used herein, a nucleic acid "probe" is single-stranded DNA or RNA, or analogs thereof, that has a sequence of nucleotides that includes at least 14, at least 20, at least 50, at least 100, at least 200, at least 300, at least 400, or at least 500 contiguous bases that are the same as (or the complement of) any contiguous bases set forth in any of SEQ ID NO:1, SEQ ID NO:7, SEQ ID NO:8, SEQ ID NO:9 or SEQ ID NO:10. Preferred regions from which to construct probes include 5' and/or 3' coding regions of SEQ ID NO:1, SEQ ID NO:7, SEQ ID NO:8, SEQ ID NO:9 or SEQ ID NO:10. In addition, the entire cDNA encoding region of an invention DS-CAM protein, or the entire sequence corresponding to SEQ ID NO:1, SEQ ID NO:7, SEQ ID NO:8, SEQ ID NO:9 or SEQ ID NO:10, may be used as a probe. Probes may be labeled by methods well-known in the art, as described hereinafter, and used in various diagnostic kits.

As used herein, the terms "label" and "indicating means" in their various grammatical forms refer to single atoms and molecules that are either directly or indirectly involved in the production of a detectable signal. Any label or indicating means can be linked to invention nucleic acid probes, expressed proteins, polypeptide fragments, or antibody molecules. These atoms or molecules can be used alone or in conjunction with additional reagents. Such labels are themselves well-known in clinical diagnostic chemistry.

The labeling means can be a fluorescent labeling agent that chemically binds to antibodies or antigens without denaturation to form a fluorochrome (dye) that is a useful immunofluorescent tracer. A description of immunofluorescent analytic techniques is found in DeLuca, "Immunofluorescence Analysis", in *Antibody As a Tool*, Marchalonis et al., eds., John Wiley & Sons, Ltd., pp. 189–231, 1982, which is incorporated herein by reference.

In one embodiment, the indicating group is an enzyme, such as horseradish peroxidase (HRP), glucose oxidase, and the like. In another embodiment, radioactive elements are employed labeling agents. The linking of a label to a substrate, i.e., labeling of nucleic acid probes, antibodies, polypeptides, and proteins, is well known in the art. For instance, an invention antibody can be labeled by metabolic incorporation of radiolabeled amino acids provided in the culture medium. See, for example, Galfre et al., *Meth. Enzymol.* 73:3–46, 1981. Conventional means of protein conjugation or coupling by activated functional groups are particularly applicable. See, for example, Aurameas et al., *Scand. J. Immunol.* 8(7):7–23, 1978; Rodwell et al., *Biotech.* 3:889–894, 1984; and U.S. Pat. No. 4,493,795.

In accordance with another embodiment of the present invention, there are provided isolated mammalian DS-CAM proteins (preferably human), polypeptides, and fragments thereof encoded by invention nucleic acid.

Preferably, DS-CAM proteins referred to herein, are those polypeptides specifically recognized by an antibody that also specifically recognizes a DS-CAM protein including the sequence set forth in SEQ ID NO:2 or SEQ ID NO:11, or the DS-CAM coding region of SEQ ID NO:7, SEQ ID NO:8 or SEQ ID NO:9. Invention isolated DS-CAM proteins are free of cellular components and/or contaminants normally associated with a native in vivo environment.

The invention DS-CAM proteins are further characterized as being primarily expressed in fetal brain and not expressed in fetal lung or fetal liver. For example, the results of Northern analysis (described in Example 4) using human fetal tissues showed that 8.5 kb and 7.6 kb transcripts are expressed only in fetal brain and not expressed in fetal lung, fetal liver and fetal kidney. Northern blot analyses of adult tissues revealed differential expression of three alternative transcripts of 9.7 kb, 8.5 kb and 7.6 kb in different substructures of the brain. The 9.7 kb transcript is highly expressed in the substantia nigra, moderately expressed in the amygdala and hippocampus, and less expressed in the whole brain. A similar pattern is observed by using a PCR product spanning the 191 bp deletion found in DS-CAM-18 and DS-CAM-52. The placenta shows faint bands, and the sizes are smaller than those in brain. In skeletal muscle, a faint band (6.5 kb) is detected.

The results of RT-PCR (Example 5) demonstrated expression of human DS-CAM mRNA in fetal and adult brain, in fetal kidney, as well as in a breast carcinoma cell line mRNA. Thus, splice variant cDNA transcripts encoding a DS-CAM family of proteins are clearly contemplated by the present invention.

The region of chromosome locus 21q22.2 from which DS-CAM is derived is part of the candidate region for holoprosencephaly type I (HPE1). In addition, some patients with this region hemizygously deleted show abnormalities of the corpus callosum and schizencephaly. Therefore, DS-CAM is contemplated as the gene, which when defective, deleted or present as a duplication, is responsible for holoprosencephaly, agenesis of the corpus callosum and/or structural defects of the brain. In addition, DS-CAM may also be responsible for several phenotypes of Down Syndrome including mental retardation as well as, more specifically, the abnormal dendritic structure observed in Down Syndrome. Additional roles for DS-CAM were further evaluated by database homology searches using BLAST X/N and TIGR database analyses. Results of these searches indicate that DS-CAM shows moderate homology to N-CAM-1 (Cunningham et al., *Science*, 236:799–806, 1987) and to DCC (Fearon et al., *Science*, 247:49–56, 1990).

Presently preferred DS-CAM proteins of the invention include amino acid sequences that are substantially the same as the protein sequence set forth in SEQ ID NO:2 or SEQ ID NO:11, or the DS-CAM coding region of SEQ ID NO:7, SEQ ID NO:8 or SEQ ID NO:9, as well as biologically active, modified forms thereof. Those of skill in the art will recognize that numerous residues of the above-described sequences can be substituted with other, chemically, sterically and/or electronically similar residues without substantially altering the biological activity of the resulting receptor species. In addition, larger or smaller polypeptide sequences containing substantially the same sequence as SEQ ID NO:2 or SEQ ID NO:11, or the DS-CAM coding region of SEQ ID NO:7, SEQ ID NO:8 or SEQ ID NO:9, therein (e.g., splice variants) are contemplated.

As employed herein, the term "substantially the same amino acid sequence" refers to amino acid sequences having at least about 50%, preferably at least about 60%, more preferably at least about 70% identity with respect to the reference amino acid sequence, and retaining comparable functional and biological activity characteristic of the protein defined by the reference amino acid sequence. In another embodiment of the invention, preferred invention proteins having "substantially the same amino acid sequence" will have at least about 80%, more preferably 90% amino acid identity with respect to the reference amino acid sequence; with greater than about 95% amino acid sequence identity being especially preferred. It is recognized, however, that polypeptides (or nucleic acids referred to hereinbefore) containing less than the described levels of sequence identity arising as splice variants or that are modified by conservative amino acid substitutions, or by substitution of degenerate codons are also encompassed within the scope of the present invention.

The term "biologically active" or "functional", when used herein as a modifier of invention DS-CAM protein(s), or polypeptide fragment thereof, refers to a polypeptide that exhibits functional characteristics similar to DS-CAM. For example, one biological activity of DS-CAM is the ability to act as an immunogen for the production of polyclonal and monoclonal antibodies that bind specifically to DS-CAM. Thus, an invention nucleic acid encoding DS-CAM will encode a polypeptide specifically recognized by an antibody that also specifically recognizes the DS-CAM protein including the sequence set forth in SEQ ID NO:2 or SEQ ID NO:11, or the DS-CAM coding region of SEQ ID NO:7, SEQ ID NO:8 or SEQ ID NO:9. Such activity may be assayed by any method known to those of skill in the art. For example, a test-polypeptide encoded by a DS-CAM cDNA can be used to produce antibodies, which are then assayed for their ability to bind to the protein including the sequence set forth in SEQ ID NO:2 or SEQ ID NO:11, or the DS-CAM coding region of SEQ ID NO:7, SEQ ID NO:8 or SEQ ID NO:9. If the antibody binds to the test-polypeptide and the protein including the sequence set forth in SEQ ID NO:2 or SEQ ID NO:11, or the DS-CAM coding region of SEQ ID NO:7, SEQ ID NO:8 or SEQ ID NO:9 with substantially the same affinity, then the polypeptide possesses the requisite biological activity.

The invention DS-CAM proteins can be isolated by a variety of methods well-known in the art, e.g., the methods described herein, the recombinant expression systems described herein, precipitation, gel filtration, ion-exchange, reverse-phase and affinity chromatography, and the like. Other well-known methods are described in Deutscher et al., *Guide to Protein Purification: Methods in Enzymology* 182 (Academic Press, 1990), which is incorporated herein by reference. Alternatively, the isolated polypeptides of the present invention can be obtained using well-known recombinant methods as described, for example, in Sambrook et al., supra., 1989).

An example of the means for preparing the invention polypeptide(s) is to express nucleic acids encoding the DS-CAM in a suitable host cell, such as a bacterial cell, a yeast cell, an amphibian cell (i.e., oocyte), or a mammalian cell, using methods well known in the art, and recovering the expressed polypeptide, again using well-known methods. Invention polypeptides can be isolated directly from cells that have been transformed with expression vectors as described below herein. The invention polypeptide, biologically active fragments, and functional equivalents thereof can also be produced by chemical synthesis. For example, synthetic polypeptides can be produced using Applied Biosystems, Inc. Model 430A or 431A automatic peptide synthesizer (Foster City, Calif.) employing the chemistry provided by the manufacturer.

The present invention also provides compositions containing an acceptable carrier and any of an isolated, purified DS-CAM polypeptide, an active fragment thereof, or a purified, mature protein and active fragments thereof, alone or in combination with each other. These polypeptides or proteins can be recombinantly derived, chemically synthesized or purified from native sources. As used herein, the term "acceptable carrier" encompasses any of the standard pharmaceutical carriers, such as phosphate buffered saline solution, water and emulsions such as an oil/water or water/oil emulsion, and various types of wetting agents.

Also provided are antisense oligonucleotides having a sequence capable of binding specifically with any portion of an mRNA that encodes DS-CAM polypeptides so as to prevent translation of the mRNA. The antisense oligonucleotide may have a sequence capable of binding specifically with any portion of the sequence of the cDNA encoding DS-CAM polypeptides. As used herein, the phrase "binding specifically" encompasses the ability of a nucleic acid sequence to recognize a complementary nucleic acid sequence and to form double-helical segments therewith via the formation of hydrogen bonds between the complementary base pairs. An example of an antisense oligonucleotide is an antisense oligonucleotide comprising chemical analogs of nucleotides.

Compositions comprising an amount of the antisense oligonucleotide, described above, effective to reduce expression of DS-CAM polypeptides by passing through a cell membrane and binding specifically with mRNA encoding DS-CAM polypeptides so as to prevent translation and an acceptable hydrophobic carrier capable of passing through a cell membrane are also provided herein. Suitable hydrophobic carriers are described, for example, in U.S. Pat. Nos. 5,334,761; 4,889,953; 4,897,355, and the like. The acceptable hydrophobic carrier capable of passing through cell membranes may also comprise a structure which binds to a receptor specific for a selected cell type and is thereby taken up by cells of the selected cell type. The structure may be part of a protein known to bind to a cell-type specific receptor.

Antisense oligonucleotide compositions are useful to inhibit translation of mRNA encoding invention polypeptides. Synthetic oligonucleotides, or other antisense chemical structures are designed to bind to mRNA encoding DS-CAM polypeptides and inhibit translation of mRNA and are useful as compositions to inhibit expression of DS-CAM associated genes in a tissue sample or in a subject.

In accordance with another embodiment of the invention, kits for detecting mutations, duplications, deletions, rearrangements and aneuploidies in chromosome 21 at locus q22.2 comprising at least one invention probe or antisense nucleotide.

The present invention provides means to modulate levels of expression of DS-CAM polypeptides by employing synthetic antisense oligonucleotide compositions (hereinafter SAOC) which inhibit translation of mRNA encoding these polypeptides. Synthetic oligonucleotides, or other antisense chemical structures designed to recognize and selectively bind to mRNA, are constructed to be complementary to portions of the DS-CAM coding strand or nucleotide sequences shown in SEQ ID NO:1, SEQ ID NO:7, SEQ ID NO:8, SEQ ID NO:9 or SEQ ID NO:10. The SAOC is designed to be stable in the blood stream for administration to a subject by injection, or in laboratory cell culture conditions. The SAOC is designed to be capable of passing through the cell membrane in order to enter the cytoplasm of the cell by virtue of physical and chemical properties of the SAOC which render it capable of passing through cell membranes, for example, by designing small, hydrophobic SAOC chemical structures, or by virtue of specific transport systems in the cell which recognize and transport the SAOC into the cell. In addition, the SAOC can be designed for administration only to certain selected cell populations by targeting the SAOC to be recognized by specific cellular uptake mechanisms which bind and take up the SAOC only within select cell populations.

For example, the SAOC may be designed to bind to a receptor found only in a certain cell type, as discussed supra. The SAOC is also designed to recognize and selectively bind to target mRNA sequence, which may correspond to a sequence contained within the sequence shown in SEQ ID NO:1, SEQ ID NO:7, SEQ ID NO:8, SEQ ID NO:9 or SEQ ID NO:10. The SAOC is designed to inactivate target mRNA sequence by either binding thereto and inducing degradation of the mRNA by, for example, RNase I digestion, or inhibiting translation of mRNA target sequence by interfering with the binding of translation-regulating factors or ribosomes, or inclusion of other chemical structures, such as ribozyme sequences or reactive chemical groups which either degrade or chemically modify the target mRNA. SAOCs have been shown to be capable of such properties when directed against mRNA targets (see Cohen et al., *TIBS* 10:435, 1989 and Weintraub, *Sci. American January* 1990, pp. 40; both incorporated herein by reference).

In accordance with yet another embodiment of the present invention, there is provided a method for the recombinant production of invention DS-CAM protein(s) by expressing the above-described nucleic acid sequences in suitable host cells. Recombinant DNA expression systems that are suitable to produce DS-CAM proteins described herein are well-known in the art. For example, the above-described nucleotide sequences can be incorporated into vectors for further manipulation. As used herein, vector (or plasmid) refers to discrete elements that are used to introduce heterologous DNA into cells for either expression or replication thereof.

Suitable expression vectors are well-known in the art, and include vectors capable of expressing DNA operatively linked to a regulatory sequence, such as a promoter region that is capable of regulating expression of such DNA. Thus, an expression vector refers to a recombinant DNA or RNA construct, such as a plasmid, a phage, recombinant virus or other vector that, upon introduction into an appropriate host cell, results in expression of the inserted DNA. Appropriate expression vectors are well known to those of skill in the art and include those that are replicable in eukaryotic cells and/or prokaryotic cells and those that remain episomal or those which integrate into the host cell genome.

As used herein, a promoter region refers to a segment of DNA that controls transcription of DNA to which it is operatively linked. The promoter region includes specific sequences that are sufficient for RNA polymerase recognition, binding and transcription initiation. In addition, the promoter region includes sequences that modulate this recognition, binding and transcription initiation activity of RNA polymerase. These sequences may be cis acting or may be responsive to trans acting factors. Promoters, depending upon the nature of the regulation, may be constitutive or regulated. Exemplary promoters contemplated for use in the practice of the present invention include the SV40 early promoter, the cytomegalovirus (CMV) promoter, the mouse mammary tumor virus (MMTV) steroid-inducible promoter, Moloney murine leukemia virus (MMLV) promoter, and the like.

As used herein, the term "operatively linked" refers to the functional relationship of DNA with regulatory and effector nucleotide sequences, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA.

As used herein, expression refers to the process well-known to those of skill in the art by which polynucleic acids are transcribed into mRNA and translated into peptides or proteins and, optionally thereafter, modified post-translationally. If the invention nucleic acid is derived from genomic DNA, expression may, if an appropriate eukaryotic host cell or organism is selected, include splicing of the mRNA.

Prokaryotic transformation vectors are well-known in the art and include pBluescript and phage Lambda ZAP vectors (STRATAGENE, San Diego, Calif.), and the like. Other suitable vectors and promoters are disclosed in detail in U.S. Pat. No. 4,798,885, issued Jan. 17, 1989, the disclosure of which is incorporated herein by reference in its entirety.

Other suitable vectors for transformation of *E. coli* cells include the pET expression vectors (Novagen, see U.S. Pat. No. 4,952,496), e.g., pET11a, which contains the T7 promoter, T7 terminator, the inducible *E. coli* lac operator, and the lac repressor gene; and pET 12a–c, which contain the T7 promoter, T7 terminator, and the *E. coli* ompT secretion signal. Another suitable vector is the pIN-IIIompA2 (see Duffaud et al., *Meth. in Enzymology,* 153:492–507, 1987), which contains the lpp promoter, the lacUV5 promoter operator, the ompA secretion signal, and the lac repressor gene.

Exemplary, eukaryotic transformation vectors, include the cloned bovine papilloma virus genome, the cloned genomes of the murine retroviruses, and eukaryotic cassettes, such as the pSV-2 gpt system (described by Mulligan and Berg,

*Nature* 277:108–114, 1979) the Okayama-Berg cloning system (*Mol. Cell Biol.* 2:161–170, 1982), and the expression cloning vector described by Genetics Institute (*Science* 228:810–815, 1985), are available which provide substantial assurance of at least some expression of the protein of interest in the transformed eukaryotic cell line.

Particularly preferred base vectors which contain regulatory elements that can be linked to the invention DS-CAM-encoding DNAs for transfection of mammalian cells are cytomegalovirus (CMV) promoter-based vectors such as pcDNA1 (Invitrogen, San Diego, Calif.), MMTV promoter-based vectors such as pMAMNeo (Clontech, Palo Alto, Calif.) and PMSG (Pharmacia, Piscataway, N.J.), and SV40 promoter-based vectors such as pSVβ (Clontech, Palo Alto, Calif.).

In accordance with another embodiment of the present invention, there are provided "recombinant cells" containing the nucleic acid molecules (i.e., DNA or mRNA) of the present invention. Methods of transforming suitable host cells, preferably bacterial cells, and more preferably *E. coli* cells, as well as methods applicable for culturing said cells containing a gene encoding a heterologous protein, are generally known in the art. See, for example, Sambrook et al., supra, 1989.

Exemplary methods of transformation include, e.g., transformation employing plasmids, viral, or bacterial phage vectors, transfection, electroporation, lipofection, and the like. The heterologous DNA can optionally include sequences which allow for its extrachromosomal maintenance, or said heterologous DNA can be caused to integrate into the genome of the host (as an alternative means to ensure stable maintenance in the host).

Host organisms contemplated for use in the practice of the present invention include those organisms in which recombinant production of heterologous proteins has been carried out. Exemplary cells for introducing DNA include cells of mammalian origin (e.g., COS cells, mouse L cells, Chinese hamster ovary (CHO) cells, human embryonic kidney (HEK) cells, African green monkey cells and other such cells known to those of skill in the art), amphibian cells (e.g., *Xenopus laevis* oöcytes), yeast cells (e.g., *Saccharomyces cerevisiae, Candida tropicalis, Hansenula polymorpha* and *P. pastoris*; see, e.g., U.S. Pat. Nos. 4,882,279, 4,837,148, 4,929,555 and 4,855,231), bacteria (e.g., *E. coli*), and the like.

In one embodiment, nucleic acids encoding the invention DS-CAM proteins can be delivered into mammalian cells, either in vivo or in vitro using suitable viral vectors well-known in the art. Suitable retroviral vectors, designed specifically for in vivo "gene therapy" methods, are described, for example, in WIPO publications WO 9205266 and WO 9214829, which provide a description of methods for efficiently introducing nucleic acids into human cells in vivo. In addition, where it is desirable to limit or reduce the in vivo expression of the invention DS-CAM, the introduction of the antisense strand of the invention nucleic acid is contemplated.

In accordance with yet another embodiment of the present invention, there are provided anti-DS-CAM antibodies having specific reactivity with DS-CAM polypeptides of the present invention. Active fragments of antibodies are encompassed within the definition of "antibody". Invention antibodies can be produced by methods known in the art using invention polypeptides, proteins or portions thereof as antigens. For example, polyclonal and monoclonal antibodies can be produced by methods well known in the art, as described, for example, in Harlow and Lane, *Antibodies: A Laboratory Manual* (Cold Spring Harbor Laboratory, 1988), which is incorporated herein by reference. Invention polypeptides can be used as immunogens in generating such antibodies. Alternatively, synthetic peptides can be prepared (using commercially available synthesizers) and used as immunogens. Amino acid sequences can be analyzed by methods well known in the art to determine whether they encode hydrophobic or hydrophilic domains of the corresponding polypeptide. Altered antibodies such as chimeric, humanized, CDR-grafted or bifunctional antibodies can also be produced by methods well known in the art. Such antibodies can also be produced by hybridoma, chemical synthesis or recombinant methods described, for example, in Sambrook et al., supra, 1989; and Harlow and Lane, supra, 1988. Both anti-peptide and anti-fusion protein antibodies can be used. (see, for example, Bahouth et al., *Trends Pharmacol. Sci.* 12:338 1991; Ausubel et al., *Current Protocols in Molecular Biology* (John Wiley and Sons, NY 1989) which are incorporated herein by reference).

Antibody so produced can be used, inter alia, in diagnostic methods and systems to detect the level of DS-CAM protein present in a mammalian, preferably human, body sample, such as tissue or vascular fluid. Such antibodies can also be used for the immunoaffinity or affinity chromatography purification of the invention DS-CAM protein. In addition, methods are contemplated herein for detecting the presence of DS-CAM polypeptides on the surface of a cell comprising contacting the cell with an antibody that specifically binds to DS-CAM polypeptides, under conditions permitting binding of the antibody to the polypeptides, detecting the presence of the antibody bound to the cell, and thereby detecting the presence of invention polypeptides on the surface of the cell. With respect to the detection of such polypeptides, the antibodies can be used for in vitro diagnostic or in vivo imaging methods.

Immunological procedures useful for in vitro detection of target DS-CAM polypeptides in a sample include immunoassays that employ a detectable antibody. Such immunoassays include, for example, ELISA, Pandex microfluorimetric assay, agglutination assays, flow cytometry, serum diagnostic assays and immunohistochemical staining procedures which are well known in the art. An antibody can be made detectable by various means well known in the art. For example, a detectable marker can be directly or indirectly attached to the antibody. Useful markers include, for example, radionucleotides, enzymes, fluorogens, chromogens and chemiluminescent labels.

Invention anti-DS-CAM antibodies are contemplated for use herein to modulate the activity of the DS-CAM polypeptide in living animals, in humans, or in biological tissues or fluids isolated therefrom. Accordingly, compositions comprising a carrier and an amount of an antibody having specificity for DS-CAM polypeptides effective to block naturally occurring ligands or other DS-CAM-binding proteins from binding to invention DS-CAM polypeptides are contemplated herein. For example, a monoclonal antibody directed to an epitope of DS-CAM polypeptide molecules present on the surface of a cell and having an amino acid sequence substantially the same as an amino acid sequence for a cell surface epitope of a DS-CAM polypeptide including the amino acid sequence shown in SEQ ID NO:2 or SEQ ID NO:11, or the DS-CAM coding region of SEQ ID NO:7, SEQ ID NO:8 or SEQ ID NO:9, can be useful for this purpose.

The present invention further provides transgenic non-human mammals that are capable of expressing exogenous nucleic acids encoding DS-CAM polypeptides. As employed herein, the phrase "exogenous nucleic acid" refers to nucleic acid sequence which is not native to the host, or which is present in the host in other than its native environment (e.g., as part of a genetically engineered DNA construct).

Also provided are transgenic non-human mammals capable of expressing nucleic acids encoding DS-CAM polypeptides so mutated as to be incapable of normal activity, i.e., do not express native DS-CAM. The present invention also provides transgenic non-human mammals having a genome comprising antisense nucleic acids complementary to nucleic acids encoding DS-CAM polypeptides, placed so as to be transcribed into antisense mRNA complementary to mRNA encoding DS-CAM polypeptides, which hybridizes to the mRNA and, thereby, reduces the translation thereof. The nucleic acid may additionally comprise an inducible promoter and/or tissue specific regulatory elements, so that expression can be induced, or restricted to specific cell types. Examples of nucleic acids are DNA or cDNA having a coding sequence substantially the same as the coding sequence shown in SEQ ID NO:1. An example of a non-human transgenic mammal is a transgenic mouse. Examples of tissue specificity-determining elements are the metallothionein promoter and the L7 promoter.

Animal model systems which elucidate the physiological and behavioral roles of DS-CAM polypeptides are also provided, and are produced by creating transgenic animals in which the expression of the DS-CAM polypeptide is altered using a variety of techniques. Examples of such techniques include the insertion of normal or mutant versions of nucleic acids encoding a DS-CAM polypeptide by microinjection, retroviral infection or other means well known to those skilled in the art, into appropriate fertilized embryos to produce a transgenic animal. See, for example, Hogan et al., *Manipulating the Mouse Embryo: A Laboratory Manual* (Cold Spring Harbor Laboratory, 1986).

Also contemplated herein, is the use of homologous recombination of mutant or normal versions of DS-CAM genes with the native gene locus in transgenic animals, to alter the regulation of expression or the structure of DS-CAM polypeptides (see, Capecchi et al., *Science* 244:1288, 1989; Zimmer et al., *Nature* 338:150, 1989; which are incorporated herein by reference). Homologous recombination techniques are well known in the art. Homologous recombination replaces the native (endogenous) gene with a recombinant or mutated gene to produce an animal that cannot express native (endogenous) protein but can express, for example, a mutated protein which results in altered expression of DS-CAM polypeptides.

In contrast to homologous recombination, microinjection adds genes to the host genome, without removing host genes. Microinjection can produce a transgenic animal that is capable of expressing both endogenous and exogenous DS-CAM protein. Inducible promoters can be linked to the coding region of nucleic acids to provide a means to regulate expression of the transgene. Tissue specific regulatory elements can be linked to the coding region to permit tissue-specific expression of the transgene. Transgenic animal model systems are useful for in vivo screening of compounds for identification of specific ligands, i.e., agonists and antagonists, which activate or inhibit protein responses.

Invention nucleic acids, oligonucleotides (including antisense), vectors containing same, transformed host cells, polypeptides and combinations thereof, as well as antibodies of the present invention, can be used to screen compounds in vitro to determine whether a compound functions as a potential agonist or antagonist to invention polypeptides. These in vitro screening assays provide information regarding the function and activity of invention polypeptides, which can lead to the identification and design of compounds that are capable of specific interaction with one or more types of polypeptides, peptides or proteins.

In accordance with still another embodiment of the present invention, there is provided a method for identifying compounds which bind to DS-CAM polypeptides. The invention proteins may be employed in a competitive binding assay. Such an assay can accommodate the rapid screening of a large number of compounds to determine which compounds, if any, are capable of binding to DS-CAM proteins. Subsequently, more detailed assays can be carried out with those compounds found to bind, to further determine whether such compounds act as modulators, agonists or antagonists of invention proteins.

Another application of the binding assay of the invention is the assay of test samples (e.g., biological fluids) for the presence or absence of DS-CAM. Thus, for example, serum from a patient displaying symptoms thought to be related to over- or under-production of DS-CAM can be assayed to determine if the observed symptoms are indeed caused by over- or under-production of DS-CAM.

In another embodiment of the invention, there is provided a bioassay for identifying compounds which modulate the activity of invention DS-CAM polypeptides. According to this method, invention polypeptides are contacted with an "unknown" or test substance (in the presence of a reporter gene construct when antagonist activity is tested), the activity of the polypeptide is monitored subsequent to the contact with the "unknown" or test substance, and those substances which cause the reporter gene construct to be expressed are identified as functional ligands for DS-CAM polypeptides.

In accordance with another embodiment of the present invention, transformed host cells that recombinantly express invention polypeptides can be contacted with a test compound, and the modulating effect(s) thereof can then be evaluated by comparing the DS-CAM-mediated response (e.g., via reporter gene expression) in the presence and absence of test compound, or by comparing the response of test cells or control cells (i.e., cells that do not express DS-CAM polypeptides), to the presence of the compound.

As used herein, a compound or a signal that "modulates the activity" of invention polypeptides refers to a compound or a signal that alters the activity of DS-CAM polypeptides so that the activity of the invention polypeptide is different in the presence of the compound or signal than in the absence of the compound or signal. In particular, such compounds or signals include agonists and antagonists. An agonist encompasses a compound or a signal that activates DS-CAM protein expression. Alternatively, an antagonist includes a compound or signal that interferes with DS-CAM protein expression. Typically, the effect of an antagonist is observed as a blocking of agonist-induced protein activation. Antagonists include competitive and non-competitive antagonists. A competitive antagonist (or competitive blocker) interacts with or near the site specific for agonist binding. A non-competitive antagonist or blocker inactivates the function of the polypeptide by interacting with a site other than the agonist interaction site.

As understood by those of skill in the art, assay methods for identifying compounds that modulate DS-CAM activity generally require comparison to a control. One type of a "control" is a cell or culture that is treated substantially the same as the test cell or test culture exposed to the compound, with the distinction that the "control" cell or culture is not exposed to the compound. For example, in methods that use voltage clamp electrophysiological procedures, the same cell can be tested in the presence or absence of compound, by merely changing the external solution bathing the cell. Another type of "control" cell or culture may be a cell or culture that is identical to the transfected cells, with the exception that the "control" cell or culture do not express native proteins. Accordingly, the response of the transfected cell to compound is compared to the response (or lack thereof) of the "control" cell or culture to the same compound under the same reaction conditions.

Since it is well-known that CAMs interact with extracellular ligands, it is contemplated that invention DS-CAM proteins interact with extracellular ligands. In another embodiment of the present invention, it is contemplated that invention DS-CAM proteins act specifically in concert or in competition with other CAMs. Thus, the present invention contemplates various bioassays for identifying ligands for invention DS-CAM proteins. In addition, the present invention contemplates an assay measuring the effect of co-expressing during development either normal or defective invention DS-CAMs with other CAMs known in the art to assess the resulting phenotype.

In one embodiment of the present invention, there is provided a bioassay for evaluating whether test compounds are capable of acting as agonists comprises:

(a) culturing cells containing:
   DNA which expresses DS-CAM protein(s) or functional modified forms thereof, and
   DNA encoding a reporter protein, wherein said DNA is operatively linked to a DS-CAM responsive transcription element;
   wherein said culturing is carried out in the presence of at least one compound whose ability to induce signal transduction activity of DS-CAM protein is sought to be determined, and thereafter
(b) monitoring said cells for expression of said reporter protein.

In another embodiment of the present invention, the bioassay for evaluating whether test compounds are capable of acting as antagonists for DS-CAM protein(s) of the invention, or functional modified forms of said DS-CAM protein(s), comprises:

(a) culturing cells containing:
   DNA which expresses DS-CAM protein(s), or functional modified forms thereof, and
   DNA encoding a reporter protein, wherein said DNA is operatively linked to a DS-CAM responsive transcription element
   wherein said culturing is carried out in the presence of:
   increasing concentrations of at least one compound whose ability to inhibit signal transduction activity of DS-CAM protein(s) is sought to be determined, and
   a fixed concentration of at least one agonist for DS-CAM protein(s), or functional modified forms thereof; and thereafter
(b) monitoring in said cells the level of expression of said reporter protein as a function of the concentration of said compound, thereby indicating the ability of said compound to inhibit signal transduction activity.

In step (a) of the above-described antagonist bioassay, culturing may also be carried out in the presence of:
fixed concentrations of at least one compound whose ability to inhibit signal transduction activity of DS-CAM protein(s) is sought to be determined, and
an increasing concentration of at least one agonist for DS-CAM protein(s), or functional modified forms thereof.

In yet another embodiment of the present invention, it is contemplated that invention DS-CAM proteins mediate signal transduction through the modulation of adenylate cyclase. For example, when a DS-CAM ligand binds to DS-CAM, adenylate cyclase causes an elevation in the level of intracellular cAMP. Accordingly, in one embodiment of the present invention, the bioassay for evaluating whether test compounds are capable of acting as agonists or antagonists comprises:

(a) culturing cells containing:
   DNA which expresses DS-CAM protein(s) or functional modified forms thereof,
   wherein said culturing is carried out in the presence of at least one compound whose ability to modulate signal transduction activity of DS-CAM protein is sought to be determined, and thereafter
(b) monitoring said cells for either an increase or decrease in the level of intracellular cAMP.

Methods well-known in the art that measure intracellular levels of cAMP, or measure cyclase activity, can be employed in binding assays described herein to identify agonists and antagonists of the DS-CAM. For example, because activation of some CAMs results in decreases or increases in cAMP, assays that measure intracellular cAMP levels can be used to evaluate recombinant DS-CAMs expressed in mammalian host cells.

As used herein, "ability to modulate signal transduction activity of DS-CAM protein" refers to a compound that has the ability to either induce (agonist) or inhibit (antagonist) signal transduction activity of the DS-CAM protein.

Each of the invention bioassays (e.g., those described herein, and the like), can be conducted as competitive assays by co-expressing one or more members of the CAM immunoglobulin superfamily of proteins known in the art, such as N-CAMs, along with invention DS-CAMs. In addition, one or more members of the CAM immunoglobulin superfamily of proteins known in the art can be co-expressed with invention DS-CAMs to evaluate the agonistic or antagonistic effect on signal transduction of the non-DS-CAM members acting in concert with invention DS-CAMS.

In yet another embodiment of the present invention, the activation of DS-CAM polypeptides can be modulated by contacting the polypeptides with an effective amount of at least one compound identified by the above-described bioassays.

Members of the N-CAM superfamily of immunoglobulins have previously been implicated in disease. For example, various alterations of N-CAM levels have been seen in degenerative disease, developmental defects, and toxic conditions. Increases in the levels of N-CAM in the cerebrospinal fluid of patients with multiple sclerosis have been observed to parallel their clinical improvement (Massaro et al., *Ital. J. Neurol. Sci. Suppl.* 6:85–88, 1987). Levels of N-CAM were reported to be elevated in the amniotic fluid of mothers carrying fetuses with neural tube defects (Ibsen et al., *J. Neurochem.* 41:363–366, 1983). Since many such defects are likely to be due to mechanical aberrations rather than genetic defects, confirmation of these results would provide a new diagnostic component for prenatal testing. Another provocative finding relates to observations on the stimulation of Golgi sialyltransferases by lead (Breen and Regan, *Development* 104:147–154, 1988; and Cookman et al., *J. Neurochem.* 49:399–403, 1987). Exposure to lead chloride markedly stimulated sialyltransferase activity from postnatal days 16 to 30 in rate. This time is coincident with the period when N-CAM normally becomes less sialylated. Thus exposure to lead at critical developmental periods would presumably lead to more highly sialylated, less adhesive, forms of N-CAM: this prevention of E-A conversion could have significant effects on neural development. E-A conversion itself has been found to be delayed in the mouse mutant staggerer (Edelman and Chuong, *Proc. Natl. Acad. Sci. USA,* 79:7036–7042, 1982) in conjunction with the connectivity changes associated with the mutation.

The location and expression of DS-CAM in the Down Syndrome (DS) phenotype is supported by the studies of patients with partial trisomy 21. A subset of the DS features, including the typical facial appearance and mental retardation, were suggested by duplication of band 21q22 only (Niebuhr, *Humangenetik* 21:99–101, 1974). Other studies mapped those features and congenital heart disease to the region 21q22.2–q22.3 and between D21S267 and MX1/MX2 (Korenberg et al., *Am. J. Hum. Genet.* 50:294–302, 1992 and Korenberg et al., *Proc. Natl. Acad. Sci. USA* 91:4997–5001, 1994), a region of about 4 Mb that contains DS-CAM. The Ts65Dn mouse model of DS contains the region of MMU16 (Pgk1-ps1 to MX1/2) that includes DS-CAM and reveals some of the neurobehaviourial features of DS (Reeves et al., *Nature Genet.* 11:177–183, 1995 and Holtzman et al., *Proc. Natl. Acad. Sci. USA* 93:13333–13338, 1996).

Close to 6% of DS individuals have Hirschsprung's disease (HSCR)(Garver et al., *Clin. Genet.* 28:503–5–8, 1985) and more than 10% of all HSCR is associated with DS (Passarge, *New Eng. J. Med.* 276:138–143, 1967). A modifier region of HSCR on chromosome 21q22 (D21S259–D21S156) has been reported in non-DS HSCR (Puffenberger et al., *Hum. Mol. Genet.* 3:1217–1225, 1994). The DS-CAM gene maps within this small region. The expression of DS-CAM in the neural crest derived enteric plexus of the gut was detected by mouse tissue in situ hybridization (Example 7). The function of the DS-CAM protein as a neural cell adhesion molecule and the association of this region of chromosome 21 with HSCR, indicate that DS-CAM can play a role in the migration of the cranial neural crest that populate this region. Thus, DS-CAM overexpression is responsible for the chromosome 21 association in non-DS HSCR and for the HSCR seen in DS.

Mutations in the molecule CAM-L1, a molecule more similar to DS-CAM than to N-CAM (FIG. 4), have established roles in human disease. The result in X-linked hydrocephalus (Rosenthal et al., *Nature Genet.* 2:107–112, 1992), type 1 X-linked spastic paraplegia and the MASA syndrome (including mental retardation, aphasia, shuffling gait, adducted thumb and agenesis of the corpus callosum) (Jouet et al., *Nature Genet.* 7:402–407, 1994). The perturbation of development by the aneuploid expression of CAM-L1 supports a role for the aneuploid expression of DS-CAM in the causation of developmental and neurological abnormalities.

In accordance with another embodiment of the present invention, there are provided methods for diagnosing DS-CAM associated disease, such as mental retardation, holoprosencephaly, agenesis of the corpus callosum, or schizencephaly, said method comprising:

detecting, in said subject, a genomic or transcribed mRNA sequence including SEQ ID NO:1 or SEQ ID NO:10, or fragments thereof.

Preferably, the DS-CAM nucleic acids detected in accordance with the invention diagnostic methods are either mutated in one form or another (such as point mutations, deletions, and the like), or are overexpressed relative to levels of DS-CAM expression in healthy non-diseased individuals.

In accordance with another embodiment of the present invention, there are provided diagnostic systems, preferably in kit form, comprising at least one invention nucleic acid in a suitable packaging material. The diagnostic nucleic acids are derived from the DS-CAM-encoding nucleic acids described herein. In one embodiment, for example, the diagnostic nucleic acids are derived from SEQ ID NO:1, SEQ ID NO:7, SEQ ID NO:8, SEQ ID NO:9 or SEQ ID NO:10. Invention diagnostic systems are useful for assaying for the presence or absence of nucleic acid encoding DS-CAM in either genomic DNA or in transcribed nucleic acid (such as mRNA or cDNA) encoding DS-CAM.

A suitable diagnostic system includes at least one invention nucleic acid, preferably two or more invention nucleic acids, as a separately packaged chemical reagent(s) in an amount sufficient for at least one assay. Instructions for use of the packaged reagent are also typically included. Those of skill in the art can readily incorporate invention nucleic probes and/or primers into kit form in combination with appropriate buffers and solutions for the practice of the invention methods as described herein.

As employed herein, the phrase "packaging material" refers to one or more physical structures used to house the contents of the kit, such as invention nucleic acid probes or primers, and the like. The packaging material is constructed by well known methods, preferably to provide a sterile, contaminant-free environment. The packaging material has a label which indicates that the invention nucleic acids can be used for detecting a particular sequence encoding DS-CAM including the nucleotide sequence set forth in SEQ ID NO:1, SEQ ID NO:7, SEQ ID NO:8, SEQ ID NO:9 or SEQ ID NO:10, thereby diagnosing the presence of, or a predisposition for, holoprosencephaly, agenesis of the corpus callosum, or for several phenotypes of Down Syndrome including mental retardation, and the like. In addition, the packaging material contains instructions indicating how the materials within the kit are employed both to detect a particular sequence and diagnose the presence of, or a predisposition for, holoprosencephaly, agenesis of the corpus callosum, or for several phenotypes of Down syndrome including mental retardation, and the like.

The packaging materials employed herein in relation to diagnostic systems are those customarily utilized in nucleic acid-based diagnostic systems. As used herein, the term "package" refers to a solid matrix or material such as glass, plastic, paper, foil, and the like, capable of holding within fixed limits an isolated nucleic acid, oligonucleotide, or primer of the present invention. Thus, for example, a package can be a glass vial used to contain milligram quantities of a contemplated nucleic acid, oligonucleotide or primer, or it can be a microtiter plate well to which microgram quantities of a contemplated nucleic acid probe have been operatively affixed.

"Instructions for use" typically include a tangible expression describing the reagent concentration or at least one assay method parameter, such as the relative amounts of reagent and sample to be admixed, maintenance time periods for reagent/sample admixtures, temperature, buffer conditions, and the like.

All U.S. patents and all publications mentioned herein are incorporated in their entirety by reference thereto. The invention will now be described in greater detail by reference to the following non-limiting examples.

Materials and Methods

Unless otherwise stated, the present invention was performed using standard procedures, as described, for example in Maniatis et al., *Molecular Cloning: A Laboratory Manual*, Cold Spring Harbor Laboratory Press, Cold Spring Harbor, N.Y., USA, 1982; Sambrook et al., supra, 1989; Davis et al., *Basic Methods in Molecular Biology*, Elsevier Science Publishing, Inc., New York, USA, 1986; or *Methods in Enzymology: Guide to Molecular Cloning Techniques* Vol. 152, S. L. Berger and A. R. Kimmerl Eds., Academic Press Inc., San Diego, USA, 1987.

Libraries.

Construction of Bacterial Artificial Chromosome (BAC) library. BAC library construction of total human genomic DNA was performed as described in Shizuya et al., *Proc. Natl. Acad. Sci. USA* 89:8794–8797, 1992; and Hubert et al., *Genomics* 41:218–226, 1997. Yeast artificial chromosome (YAC) clones were obtained from the CEPH mega-YAC library and grown under standard conditions (Cohen et al., *Nature* 366:689–701 1993).

P1 artificial chromosome (PAC) library construction. A 3×human PAC library, designated RPCI-1 (Ioannou et al., *Hum. Genet.* 219–220, 1994) was constructed as described (Ioannou et al., *Nat. Genet.* 6:84–89, 1994). The library was arrayed in 384 well dishes. Subsequently, STSs generated by sequencing of clones using vector primers were used as hybridization probes to gridded colony filters of the PAC library.

YAC DNA preparation. YAC clones were grown in selective media, pelleted and resuspended in 3 ml 0.9 M sorbitol, 0.1M EDTA pH 7.5, then incubated with 100 U of lytocase (Sigma, St. Louis, Mo.) at 37° C. for 1 hour. After centrifugation for 5 minutes at 5,000 rpm pellets were resuspended in 3 ml 50 mM Tris pH 7.45, 20 mM EDTA 0.3 ml 10% SDS was added and the mixture was incubated at 65° C. for 30 minutes. One ml of 5 M potassium acetate was added and tubes were left on ice for 1 hour, then centrifuged at 10,000 rpm for 10 minutes. Supernatant was precipitated in 2 volumes of ethanol and pelleted at 6,000 rpm for 15 minutes. Pellets were resuspended in TE, treated with RNase and reextracted with phenol-chloroform.

Analysis by fluorescence in situ hybridization (FISH). PAC or BAC clones were biotinylated by nicktranslation in the presence of biotin-14-dATP using the BioNick Labeling Kit (Gibco-BRL). FISH was performed essentially as described (Korenberg et al., *Cytogenet. Cell Genet.* 69:196–200, 1995). Briefly, 400 ng of probe DNA was mixed with 8 ng of human Cot 1 DNA (Gibco-BRL) and 2 µg of sonicated salmon sperm DNA in order to suppress possible background produced from repetitive human sequences as well as yeast sequences in the probe. The probes were denatured at 75° C., preannealed at 37° C. for one hour, and applied to denatured chromosome slides prepared from normal male lymphocytes (Korenberg et al., supra, 1995). Post-hybridization washes were performed at 40° C. in 2×SSC/50% formamide followed by washes in 1×SSC at 50° C. Hybridized DNAs were detected with avidin-conjugated fluorescent isothiocyanate (Vector Laboratories). One amplification was performed by using biotinylated anti-avidin. For distinguishing chromosome subbands precisely, a reverse banding technique was used, which was achieved by chromomycin A3 and distamycin A double staining (Korenberg et al., supra, 1995). The color images were captured by using a Photometrics Cooled-CCD camera and BDS image analysis software (Oncor Imaging, Inc.).

Southern blot analysis. Gel electrophoresis of DNA was carried out on 0.8% agarose gels in 1×TBE. Transfer of nucleic acids to HYBOND® nylon membrane (Amersham) was performed according to the manufacturer's instruction. Probes were labeled using RadPrime Labeling System (BRL). Hybridization was carried out at 42° C. for 16 hours in 50% formamide, 5×SSPE, 5× Denhardt's 0.1% SDS, 100 mg/ml denatured salmon sperm DNA. The filters were washed once in 1×SSC, 0.1% SDS at room temperature for 20 minutes, and twice in 0.1×SSC, 0.1% SDS for 20 minutes at 65° C. The blots were exposed onto X-ray film (Kodak, X-OMAT-AR).

Sequencing of PAC and BAC endclones. PAC clones were inoculated into 500 ml of LB/kanamycin and grown overnight. BAC clones were inoculated into 500 ml of LB/chloramphenicol and grown overnight. DNAs were isolated using QIAGEN columns according to the vendors protocol with one additional phenol/chloroform/isoamylalcohol extraction followed by one additional chloroform/isoamylalcohol extraction. Clones were sequenced using the Gibco-BRL cycle sequencing kit with standard T7 and SP6 primers.

EXAMPLE 1

Construction of BAC Contig

To provide stable clones for gene isolation and sequencing initiatives in the D21S55 to MX1 region, contigs were constructed using Bacterial Artificial Chromosomes (BACs) and P1 Artificial Chromosomes (PACs). BAC library construction of total human genomic DNA was performed as described (Shiyuza et al., supra, 1992; Kim et al., *Genomics* 34:213–218, 1996). A BAC library was screened using several YACs spanning the region; a PAC library (Iannou et al., *Nature Genet.* 6:84–89, 1994) was screened using radiolabeled STS PCR products and whole BACs in gap filling initiatives.

The location of these BAC and PAC clones was confirmed by fluorescence in situ hybridization (FISH). Clone to clone Southerns using 24 new STSs (generated from direct sequencing of BAC and PAC ends) along with 35 pre-existing STSs were used to show overlaps between BACs and PACs. The STS density over the intervals covered in BACs and PACs was 1 STS every 60 kb, and 79% of the clones were positive for 2 or more STSs. Approximately 3.5 Mb of the 4–5 Mb D21S55 to MX1 interval is covered in 85 BACs and 25 PACs representing 4-fold coverage within the contigs (Hubert et al., *Genomics* 41:218–226, 1997). The minimal contig sizes as determined by counting only non-overlapping clones are: 1100 kb, 900 kb, 510 kb, 380 kb and 270 kb. Insert size of BAC clones was measured by running pulse-field gel electrophoresis after digesting DNA with NotI.

EXAMPLE 2

Direct cDNA Selection

A modified direct cDNA selection technique (Yamakawa et al., *Hum. Mol. Genet.* 4:709–716, 1995; Yamakawa et al., *Cytogenet. Cell Genet.* 74:140–145, 1996) was applied to BAC-423A5, BAC-430F1, BAC-628H2, BAC-371H8 and PAC-31P10 (FIG. 1) by using cDNA from trisomy 21 human fetal brain, and the selected fragments were then subcloned into a plasmid vector.

Total RNA was isolated from 14 week trisomy 21 fetal brain using TRI region™ (Molecular Research Center, Inc.). Poly (A)$^+$ RNA was isolated using Poly (A) Quick® mRNA isolation kit (STRATAGENE). Double stranded cDNA was synthesized using SuperScript™ Choice System (GIBCO BRL) from 5 μg trisomy 21 fetal brain poly (A)+ RNA using 1 μg oligo (dT)$_{15}$ or 0.1 μg random hexamer. The entire synthesis reaction was purified by Gene Clean® II kit (BIO101, Inc.) and then kinased. Sau3AI linker was attached to the cDNA which was subsequently digested with Sau3AI. The reaction was purified using Gene Clean. MboI linker was attached to the cDNA and the reaction purified by Gene Clean (Morgan et al., supra, 1992). The synthesized product was amplified by PCR using one strand of MboI linker (5'CCTGATGCTCGAGTGAATTC3') (SEQ ID NO:4) as a primer. PCR cycling conditions were 40 cycles of 94° C./15 seconds, 60° C./23 seconds, 72° C./2 minutes in a 100 μl of 1×PCR buffer (Promega), 3 mM MgCl$_2$, 5.0 units of Taq polymerase (Promega), 2 μM primer and 0.2 mM dNTPs.

Nineteen BAC DNAs (total 2.5 μg) and 2 PAC DNAs between the region ETS2 and MX1 were prepared using QIAGEN plasmid kit and were biotinylated using Nick Translation Kit and biotin-16-dUTP (Boehringer Manneheim). 3 μg of heat denatured PCR amplified cDNA was annealed with 3 μg of heat denatured COT1 DNA (BRL) in 100 μl hybridization buffer (750 mM NaCl, 50 mM NaPO$_4$(pH7.2), 5 mM EDTA, 5× Denhardt's, 0.05% SDS and 50% formamide) at 42° C. for two hours. After prehybridization, 1.2 μg of heat denatured biotinylated BAC DNA was added and incubated at 42° C. for 16 hours. cDNA-BAC DNA hybrids were precipitated with EtOH and dissolved in 60 μl of 10 mM Tris-HCl (pH 8.0), 1 mM EDTA. After addition of 40 μl 5 M NaCl, the DNA was incubated with magnetic beads (Dynabeads M-280, Dynal) at 25° C. for 1 hour with gentle rotating to allow attachment of the DNA to the magnetic beads. The beads were then washed twice by pipetting in 400 μl of 2×SSC, setting in magnet holder (MPC-E$_{TM}$, Dynal) for 30 seconds and removing the supernatant. Four additional washes were performed in 0.2×SSC at 68° C. for 10 minutes each with transfer of the beads to new tubes at each wash. cDNAs were eluted in 100 μl of distilled water for 10 minutes at 80° C. with occasional mixing. The eluted cDNAs were amplified by PCR as described above. After twice repeating the selection procedure using magnetic beads, amplified cDNAs were digested with EcoRI and subcloned into pBlueScript KS+ (STRATAGENE). Insert DNAs were isolated from the subclones, and were analyzed by Southern hybridization and DNA sequencing.

The direct cDNA selection procedure using 19 BACs and 2 PACs between ETS2 and MX1 generated a total of 145 unique cDNA fragments. Genbank and TIGR homology searches using FASTA revealed matches to ETS2, HMG14, PEP19, a Na K ATPase, Titan ESTs, MX1 region ESTs, and 14 ESTs of unknown function. A cDNA library from a trisomy 21 fetal brain at 14 weeks gestation was screened using one of these unique cDNA fragments labeled "E51" (SEQ ID NO:3).

EXAMPLE 3

Isolation of Human DS-CAM cDNA Using cDNA Library Screening

A trisomy 21 human fetal brain (14 weeks of age) cDNA library was constructed using ZAP-cDNA® synthesis kit (STRATAGENE) which generates a unidirectional cDNA library. Briefly, double-stranded cDNA was synthesized from 5 μg trisomy 21 fetal brain poly(A) RNA using a hybrid oligo(dT)-XhoI linker primer with 5-methyl dCTP. An EcoRI linker was attached to the cDNA which was subsequently digested with EcoRI and XhoI, and then cloned into UNI-ZAP XR vector (STRATAGENE). The library was packaged using Gigapack® II Gold packaging extract. The titer of the original library was 1.1×10$^6$ p.f.u./package. The library was amplified once. A blue-white color assay indicated that 99% of the clones had inserts.

Screening of the trisomy 21 fetal brain cDNA library was performed using one of the 145 unique cDNA fragments labeled "E51" (SEQ ID NO:3) prepared as described above. Phages were plated to an average density of 1×10$^5$ per 175 cm$^2$ plate. Plaque lifts of 20 plates (2×10$^6$ phages) were made using duplicated nylon membranes (Hybond-N+; Amersham). Hybridized membranes were washed to final stringency of 0.2×SSC, 0.1×SDS at 65° C. The filters were exposed overnight onto X-ray film.

Identification of 62 clones were made out of 2×10$^6$ clones in the original library. Eighteen of these positive phage clones were converted to plasmids, and their DNAs were isolated. These cDNAs were independently numbered as separate DS-CAM (Down Syndrome Cell Adhesion Molecule) clones. The length of the inserts of these clones ranged from 2.4 kb to 6.6 kb. Exon trapping (Buckler et al., Proc. Natl. Acad. Sci. USA 88:4005–4009, 1991; Church et al., Nature Genet. 6:98–105, 1994) was also used to isolate cDNAs in the BAC and PAC contig. With this approach, three exons identified from BAC-539E7 and one from BAC-430F1 were found to identify the same sequences as those isolated by cDNA selection.

Sequence analysis of one of the clones, labeled DS-CAM-42, revealed a 6110 bp DNA sequence which contained a large ORF (5687 bp) as well as 3'-UTR sequence (423 bp), but the 5'UTR and start codon were not located in clone DS-CAM-42. To characterize the 5' end, two further clones, DS-CAM-18 of 6.5 kb and DS-CAM-52 of 6.6 kb were characterized. Sequence analyses of these clones close to the 5' end overlap with sequence at the 5' end of DS-CAM-42. However, DS-CAM-18 extends 416 bp farther 5', and DS-CAM-52 extends 494 bp farther 5' than DS-CAM-42. The extra 494 bp sequence extends the ORF by 43 bp at the 5' end and contains a start codon. Two stop codons occur 330 bp and 427 bp upstream of the start codon. The 494 bp of additional 5' sequence found in DS-CAM-52 combined with DS-CAM-42 (6604 bp) yield a consensus cDNA that encodes one isoform of the invention protein labeled DS-CAM1. The DS-CAM1 cDNA contains an open reading frame of 5730 bp (SEQ ID NO:1) coding for a 1910 amino acid protein (SEQ ID NO:2; approximately 211 kilodaltons), flanked by 452 bp of 5'-UTR and 422 bp of 3'-UTR. The 5'-UTR is highly GC rich (81% GC over 452 bp) and contains 13 MspI sites, as well as 72 CG and 93 GC dinucleotide pairs.

Figure 2A:
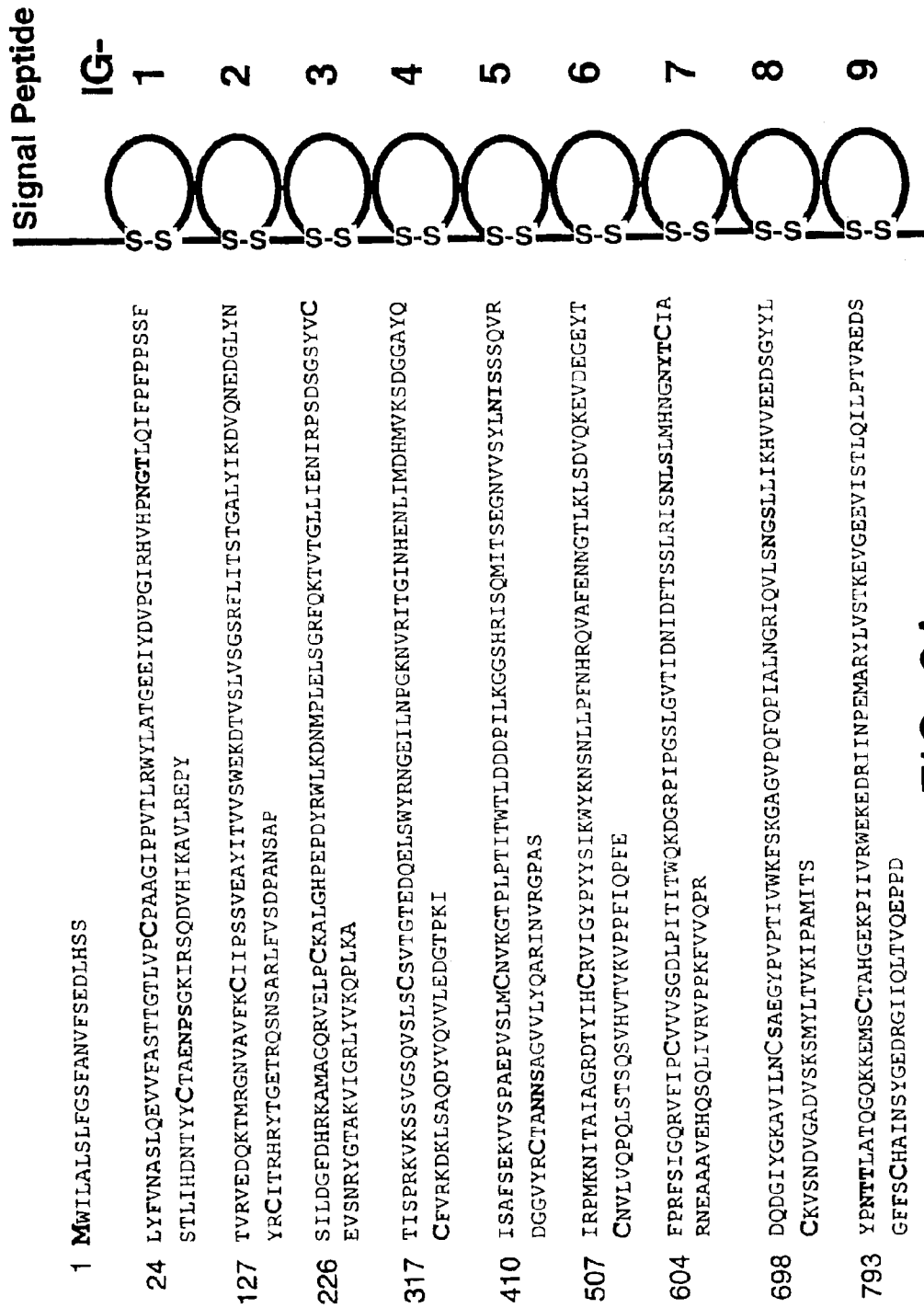
FIGS. 2A–2B show the predicted amino acid sequence of the human DS-CAM1 protein corresponding to SEQ ID NO: 2 and a schematic structure. IG.
Figure 2B:
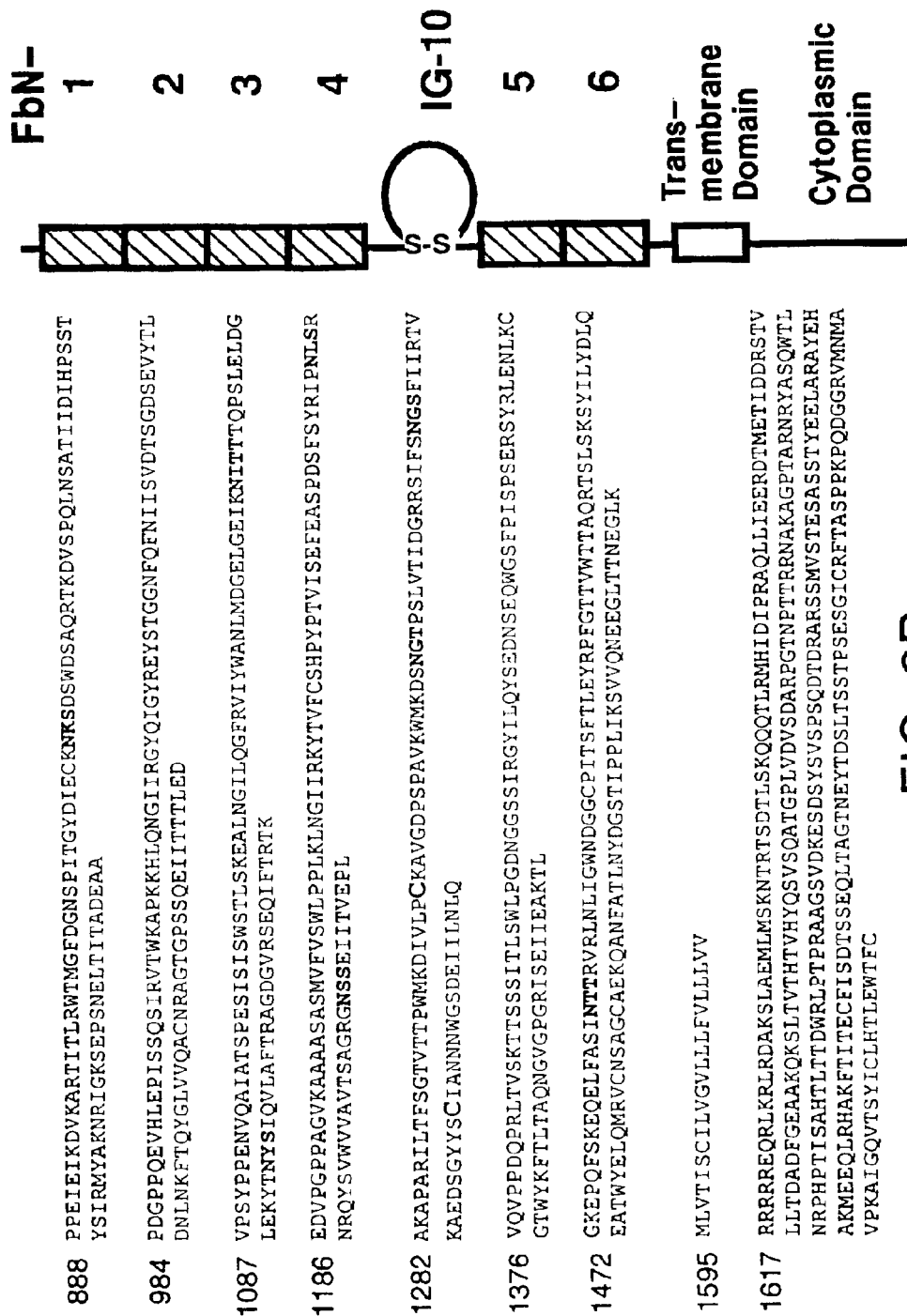

The DS-CAM1 protein contains an extracellular component at the N-terminus consisting of nine tandemly repeated Ig-like C2 type domains and a tenth Ig-like C2 domain located between domains four and five of an array of six repeated fibronectin type III domains (FIG. 2). Each Ig-like C2 domain consists of approximately 100 amino acids with a pair of conserved cysteines separated by 49–56 residues. A single transmembrane domain of 22 amino acids was defined by using the TMBASE program (Hoffmann and Stoffel, Biol. Chem. Hoppe-Seyler 374:166, 1993). The remaining 294 amino acids at the C-terminus corresponding to the cytoplasmic domain have partial homologies to the mouse M-phase inducer phosphatase 2 (Kakizuka et al., Genes Dev. 6:578–590, 1992) in two regions, one with 34% identity and 52% similarity over 46 bp and a second with 38% identity and 52% similarity over 21 bp. The homolog of Drosophila glass gene (O'Neill et al., Proc. Natl. Acad.

Sci. USA 92:6557–6561, 1995) with 30% identity and 52% similarity over 42 bp, and the mouse delta opioid receptor (Evans et al., *Science* 258:1952–1955, 1992) with 43% identity and 60% similarity over 30 bp. The putative protein contains 16 potential N-glycosylation sites.

A homology search of the predicted amino acid sequence of the 5730 bp open reading frame of DS-CAM1 (SEQ ID NO:1) to genes registered in the Genbank and the EMBL databases was conducted by using the BLAST-P program (Altschul et al., *J. Mol. Biol.* 215:403–410, 1990). The predicted amino acid sequence revealed homologies to multiple proteins (FIG. 4) including CAM-L1 (Moos et al., *Nature* 334:701–703, 1988), BIG-1 (brain-derived immunoglobulin (Ig) superfamily molecule-1) (Yoshihara et al., *Neuron* 13:415–426, 1994), DCC (deleted in colon cancer) (Fearon et al., *Science* 247:49–56, 1990), and revealed DS-CAM as defining a novel class of the immunoglobulin (Ig) superfamily. Homology searches with sequences of Ig type-C2 domains and fibronectin type-III domains of the most highly related Ig-superfamily members (CAM-L1, DCC, and axonin-1) were conducted by using the FASTA program (Pearson and Lipman, *Proc. Natl. Acad. Sci. USA* 85:2444–2448, 1988).

In addition, a splice variant cDNA sequence encoding a non-membrane bound isoform of DS-CAM1, referred to herein as DS-CAM2, is provided herein. Two human DS-CAM cDNA clones (DS-CAM-18 and DS-CAM-52) were found to contain identical deletions of 191 bp that occur in neighboring exons and that delete bp 5133 to 5323 of the SEQ ID NO:1 cDNA sequence encoding DS-CAM1 (FIG. 3). The resulting splice variant transcript encoding DS-CAM2 (SEQ ID NO:10) is deleted for the entire transmembrane domain that is encoded by the more 3' of these exons. Further, the deletion changes the reading frame and creates a stop codon 36 bp downstream of the deletion resulting in a soluble extracellular protein of 1571 amino acids (SEQ ID NO:11). The distal border of the resulting deletion contains the canonical AG of the RNA splicing consensus acceptor site. The proximal border contains a variant of the donor splice site consensus sequence (Jackson, *Nucl. Acids Res.* 19:3795–3798, 1991).

To confirm that the DS-CAM cDNA originated from the BACs and PACs in the Down syndrome region and to determine the genomic size of DS-CAM, the longest DS-CAM cDNA clones (DS-CAM-42; 6.1 kb, DS-CAM-18; 6.5 kb, DS-CAM-52; 6.6 kb) were hybridized to Southern blots containing the BAC and PAC clone contig (FIG. 1) DS-CAM-42, 18 and 52 hybridized to BACs 423A5, 430F1, 628H2, 539E7, 371H8, 825E1, 593D1, 261F12, 30E4, 385B7, 388F4, and to PACs 31P10, 58D10. BACs 816F6, 116E8, 720G4, 619H8 were only positive for DS-CAM-18 and DS-CAM-52 but negative for DS-CAM-42. All other BACs shown in FIG. 1 were negative. These results indicate that the DS-CAM gene spans 900 kb–1200 kb genomic DNA and covers a gap in this BAC and PAC contig indicated by an arrowhead as well as in the available YAC contigs (Korenberg et al., *Genome Res.* 5:427–443, 1995; Gardiner et al., *Somat. Cell Mol. Genet.* 21:399–414, 1995). DS-CAM cDNA sequences were confirmed to originate from these BACs and PACs by direct sequencing of the BACs and PACs as templates using cDNA sequence-specific primers.

The map position of DS-CAM on chromosome 21q22.2–22.3 was confirmed by using clone DS-CAM-42 as a probe for fluorescence in-situ hybridization. Two independent experiments were performed and over 100 metaphase cells were evaluated. Signals were clearly seen on two chromatids of at least one chromosome in 85% of cells. There were no other double signal sites seen in greater than 1% of cells.

EXAMPLE 4

Northern Blot Analysis Of Human DS-CAM Expression

Inserts containing DS-CAM cDNA were excised from the base vector by digestion with XhoI and EcoRI. After labeling using the random priming method (RadPrime Labeling System; GIBCO BRL), followed by purification using G-50 Sephadex columns (Quick Spin Column; Boehringer Mannheim), the fragments were used a probes for Northern hybridization using Multiple Tissue Northern Blot (Clontech). A Northern blot assay was conducted using DS-CAM cDNA as a probe in various fetal and adult tissues including heart, brain, placenta, lung, liver, skeletal muscle, kidney, and pancreas. Northern hybridization was performed by following the manufacturer's instructions. The hybridized membrane was washed at a final stringency of 0.1×SSC and 0.1×SDS at 50° C. The filter was exposed to X-ray film (Kodak X-OMAT AR) at −70° C. for 1–5 days.

The results of Northern analysis using human fetal tissues showed that 8.5 kb and 7.6 kb transcripts are expressed only in fetal brain and not expressed in fetal lung, fetal liver and fetal kidney. In adult tissues, three transcripts of 9.7 kb, 8.5 kb, and 7.6 kb are present in the brain. Placenta shows faint bands, and the sizes are similar to those in brain. In skeletal muscle, a faint smaller band (6.5 kb) is detected. In multiple parts of the adult human brain, transcripts of 9.7 kb, 8.5 kb and 7.6 kb are differentially expressed. The 9.7 kb transcript is highly expressed in the substantia nigra, moderately expressed in amygdala and hippocampus, and less expressed in the whole brain. A similar pattern is obtained using a PCR product which spans the 191 bp deletion found in clones DS-CAM-18 and DS-CAM-52 encoding the splice variant sequence corresponding to DS-CAM2. Thus, splice variant cDNA transcripts encoding a DS-CAM family of proteins are clearly contemplated by the present invention.

EXAMPLE 5

RT-PCR Assays Of Human DS-CAM Expression

Reverse-transcriptase polymerase chain reaction (RT-PCR) assays verses cDNA libraries of various human tissues were conducted using primers numbered B9-131F (SEQ ID NO:5) and B9-131R (SEQ ID NO:6). The results demonstrated expression of human DS-CAM mRNA in fetal and adult brain, and fetal kidney. In addition, a breast carcinoma cell line showed expression of human DS-CAM mRNA.

The cDNAs from 13 independent human fetal and adult sources were analyzed by PCR using primer pairs that flanked the alternatively spliced region that results in a 191 base pair deletion of nucleotides 5133–5323 of the DS-CAM1 cDNA set forth in SEQ ID NO:1. The primers were designed to generate products of different sizes for each of the two alternatively spliced transcripts: 536 bp corresponding to the non-deleted DS-CAM-1 transcript and 345 bp corresponding to the deleted DS-CAM2 transcripts. The analyses included adult samples from amygdala (24 years), skeletal muscle (36 years) and three independent lymphoblastoid cell lines. Fetal samples included whole brain of a trisomy 21 fetus (14 weeks), four from whole brain (4.5–13 weeks), one from temporal lobe (28 weeks) and two from heart (4.5 and 13 weeks). The results indicate that all fetal and adult samples produced two bands corresponding to PCR products of the predicted sizes which indicates the expression of two alternatively spliced transcripts.

EXAMPLE 6

Isolation of Mouse DS-CAM cDNA Clones

A mouse brain cDNA library was prepared from 19 week old female C57 Black/6 mice in the Uni-ZAP XR Vector (STRATAGENE). The cDNAs were oligo-dT primed and cloned unidirectionally into the EcoRI and XhoI sites of the vector. The average insert size is 1.0 kb. The library was screened using a human DS-CAM cDNA clone as a probe. Two partial mouse DS-CAM cDNA clones were isolated and sequenced. The combined nucleotide sequences of these clones are set forth in SEQ ID NO:7, SEQ ID NO:8 and SEQ ID NO:9, and were found to represent the 5l, middle and 3' portions, respectively, of cDNA encoding a mouse DS-CAM.

EXAMPLE 7

Hybridization Analysis of DS-CAM cDNA in Mouse Tissues

BALB/c and C57BL/6×DBA/2 embryos, fetuses and postnatal brains were fixed and embedded as described in detail in Lyons et al., (*J. Neurosci.* 15:5727–5738, 1995). Embryos were fixed in 4% paraformaldehyde in phosphate buffered saline (PBS) overnight, dehydrated and infiltrated with paraffin. Five to seven micron serial sections were mounted on gelatinized slides. Two sections were mounted/slide, deparaffinized in xylene, rehydrated and post-fixed. The sections were digested with proteinase K, post-fixed, treated with tri-ethanolamine/acetic anhydride, washed and dehydrated. cRNA probes were prepared from DS-CAM-M-14. The plasmid was linearized with XbaI and T7 polymerase was used to generate the antisense cRNA. The plasmid was linearized with KpnI and T3 polymerase was used to generate the sense control cRNA. The cRNA transcripts were synthesized according to manufacturer's conditions (STRATAGENE) and labeled with $^{35}$S-UTP (>1000 Ci/mmol; Amersham). cRNA transcripts larger than 100 nucleotides were subjected to alkali hydrolysis to give a mean size of 70 bases for efficient hybridization.

Sections were hybridized overnight at 52° C. in 50% deionized formamide, 0.3M NaCl, 20 mM Tris-HCl pH 7.4, 5 mM EDTA, 10 mM NaPO4, 10% dextran sulfate, 1× Denhardt's, 50 µg/ml total yeast RNA, and 50–75,000 cpm/µl $^{35}$S-labeled cRNA probe. The tissue was subjected to stringent washing at 65° C. in 50 formamide, 2×SSC, 10 mM DTT and washed in PBS before treatment with 20 µg/ml RNase A at 37° C. for 30 minutes. Following washes in 2×SSC and 0.1×SSC for 10 minutes at 37° C., the slides were dehydrated and dipped in Kodak NTB-2 nuclear track emulsion and exposed for 2–3 weeks in light-tight boxes with desiccant at 4° C. Photographic development was carried out in Kodak D-19. Slides were counterstained lightly with toluidine blue and analyzed using both light- and darkfield optics of a Zeiss Axiophot microscope. Sense control cRNA probes (identical to the mRNAs) always gave background levels of hybridization signal. Embryonic structures were identified with the help of the following atlases: Rugh (*The Mouse: Its Reproduction and Development.* Oxford Univ. Press, Oxford, UK, 1990), Kaufman (*The Atlas of Mouse Development.* Acad. Press, New York, N.Y., 1992), and Altman and Bayer (supra, 1995).

Tissue in situ hybridization analysis was performed using a mouse cDNA as a probe on sections of normal mouse embryos from days 8.5–17.5 post coitum (pc) as well as in newborn, two weeks and adult brains as described above.

The results indicate that there is no detectable expression of DS-CAM at 8.5 days pc. At 9.5 days pc, expression was detected in the neuroepithelium. Low levels of expression were detected within the branchial arches, suggestive of migrating neural crest cells. At 10.5 days pc, the trigeminal ganglia (neural crest derived) begin to express the transcript and expression within the branchial arches was more evident.

Expression at 11.5 days pc was abundant throughout the brain. The transcript was found within the regions of the nervous system that differentiate earliest during development (Altman and Bayer, supra, 1995). In the brain, this includes the ventral-most regions, such as the thalamus and medulla. Some expression was detected within the olfactory epithelium. Expression within the neural tube begins in two areas: the ventrolateral (corresponding to the areas in which the motor neurons differentiate) and the lateral gray columns (that later form commissural neurons) (Leber et al., *J. Neurosci.* 15:1236–1248, 1990). The dorsal root ganglia (neural crest derived) expressed the transcript at 11.5 days pc. The trigeminal ganglia show higher levels at 11.5 days pc than they did at 10.5 days. Migrating neural crest can be seen within the maxilla, the mandibular arch, and in the developing gut. Signal was observed within the mesenchyme surrounding the umbilical vein and artery.

At 12.5 days pc, expression was more extensive than at 11.5 days pc. More of the nervous system exhibits expression of the transcript, including a larger portion of midbrain, the pontine areas, the basal ganglia and the outermost layer of cortex. Neurons in this layer have undergone mitosis in the subependymal layer of the cortex and migrated into the mantle layer of the cerebral cortex as differentiated cells (Smart et al., *J. Comp. Neurol.* 116:325–347, 1961).

At 13.5 days pc, expression was seen throughout most of the brain. The outermost layer of the gut also appears to be expressing at this stage; these cells are neural crest derived and form the myenteric ganglia. At 15.5 and 16.5 days pc, most of the neural crest derived neural structures have some expression. For example, the regions of the snout that will develop into the sensory structures at the base of the vibrissae, the pancreatic ganglia, the heart ganglion, the enteric nervous system, and the sympathetic trunk all express the transcript.

There is no expression within the umbilicus at this stage. Two non-neuronal structures express this gene, the gonad and the annulus fibrosus of the intervertebral disk. The olfactory bulb exhibits signal both in the granule cells and within the tufted mitral cells. Within the newborn brain, the transcript was expressed most extensively within the differentiating regions such as the septal area, olfactory bulb, inferior colliculus and hippocampus. In the adult brain, the gene was expressed in many areas including amygdala, cortex, hippocampus and thalamus. In the adult cerebellum the transcripts were detected in the Purkinje cell layer and in the deep cerebellar nuclei.

While the invention has been described in detail with reference to certain preferred embodiments thereof, it will be understood that modifications and variations are within the spirit and scope of that which is described and claimed.

Summary of Sequences

SEQ ID NO:1 is the nucleic acid sequence (and the deduced amino acid sequence) of cDNA encoding a novel human DS-CAM1 protein of the present invention.

SEQ ID NO:2 is the deduced amino acid sequence of a human DS-CAM1 protein of the present invention.

SEQ ID NO:3 is the cDNA probe (labeled "E51") used to isolate cDNA encoding human DS-CAM.

SEQ ID NO:4 is an MboI linker sequence.

SEQ ID NO:5 is a primer labeled B9-131F used in the RT-PCR assay described in Example 5.

SEQ ID NO:6 is a primer labeled B9-131R used in the RT-PCR assay described in Example 5.

SEQ ID NO:7 is the 5' region of a partial mouse-derived cDNA clone encoding an invention DS-CAM protein.

SEQ ID NO:8 is the middle region of a partial mouse-derived cDNA clone encoding an invention DS-CAM protein.

SEQ ID NO:9 is the 3' region of a partial mouse-derived cDNA clone encoding an invention DS-CAM protein.

SEQ ID NO:10 is the nucleic acid sequence (and the deduced amino acid sequence) of cDNA encoding a novel human DS-CAM2 protein of the present invention.

SEQ ID NO:11 is the deduced amino acid sequence of a human DS-CAM2 protein of the present invention, which is a splice variant of DS-CAM1 (SEQ ID NO:2).

That which is claimed is:

1. An isolated nucleic acid consisting essentially of (a) the nucleotide sequence of SEQ ID NO:1 or 10; or (b) the complement of the nucleotide sequence of (a).

2. A vector comprising the isolated nucleic acid of claim 1.

3. An isolated cell containing the nucleic acid of claim 1 or the vector of claim 2.

4. An isolated nucleic acid molecule consisting of (a) the nucleotide sequence set forth in SEQ ID NO:1, SEQ ID NO:10, nucleotides 453–6185 of SEQ ID NO:1 or nucleotides 453–5168 of SEQ ID NO:10, or (b) the complement of the nucleotide sequence of (a).

5. A vector comprising the isolated nucleic acid of claim 4.

6. An isolated cell containing the nucleic acid of claim 4 or the vector of claim 5.

7. An oligonucleotide consisting of at least 50 contiguous nucleotides of (a) the nucleotide sequence of SEQ ID NO:1 or 10; or (b) the complement of the nucleotide sequence of (a).

8. A kit for detecting the presence of a nucleic acid in a sample comprising in a package at least one oligonucleotide of claim 7.

9. The isolated nucleic acid of claim 1, which is RNA.

* * * * *